US008356605B2

(12) United States Patent
Makower et al.

(10) Patent No.: US 8,356,605 B2
(45) Date of Patent: Jan. 22, 2013

(54) DEVICES AND METHODS FOR TREATMENT OF OBESITY

(75) Inventors: Joshua Makower, Los Altos, CA (US); Theodore M. Bender, Oakland, CA (US); Brian K. Shiu, Sunnyvale, CA (US); Pablo G. Acosta, Newark, CA (US); Shuji Uemura, San Francisco, CA (US); Josef L. Friedmann, Boulder Creek, CA (US); Crystine Lee, Vallejo, CA (US)

(73) Assignee: Vibrynt, Inc., Redwood City, CA (US)

( * ) Notice: Subject to any disclaimer, the term of this patent is extended or adjusted under 35 U.S.C. 154(b) by 1202 days.

(21) Appl. No.: 12/214,518

(22) Filed: Jun. 18, 2008

(65) Prior Publication Data

US 2008/0262521 A1 Oct. 23, 2008

Related U.S. Application Data

(63) Continuation of application No. 11/716,985, filed on Mar. 10, 2007, and a continuation-in-part of application No. 11/407,701, filed on Apr. 19, 2006, now Pat. No. 8,070,768.

(60) Provisional application No. 60/877,595, filed on Dec. 28, 2006.

(51) Int. Cl.
*A61B 19/00* (2006.01)
*A61F 2/00* (2006.01)
*A61F 13/00* (2006.01)
*A61M 29/00* (2006.01)

(52) U.S. Cl. .......... 128/898; 600/37; 606/192; 606/198

(58) Field of Classification Search .......... 606/191–194, 606/198; 128/898; 600/37
See application file for complete search history.

(56) References Cited

U.S. PATENT DOCUMENTS

| 233,475 A | 10/1880 | Cook et al. |
| 659,422 A | 10/1900 | Shidler |
| 780,392 A | 1/1905 | Wanamaker et al. |
| 789,467 A | 5/1905 | West |

(Continued)

FOREIGN PATENT DOCUMENTS

EP  1 016 377 A2  7/2000

(Continued)

OTHER PUBLICATIONS

McMillan, et al., Arthroscopic Knot-tying techniques. pp. 81-95, 2003.

(Continued)

*Primary Examiner* — Gary Jackson
*Assistant Examiner* — Michael Mendoza
(74) *Attorney, Agent, or Firm* — Law Offices of Alan W. Cannon

(57) ABSTRACT

Methods, devices, tools, instruments and systems for treating a patient to induce weight loss. In one method embodiment, a device, including an expandable member in a collapsed configuration, is passed through an opening in the skin of the patient, and into the abdominal cavity of the patient. At least a portion of the expandable member is anchored relative to at least one structure in the abdominal cavity, without piercing the stomach. The expandable member is expanded to an expanded configuration in a space in the abdominal cavity to perform at least one of: prevention of expansion of the stomach of the patient into the space; and compression of a portion of the stomach.

6 Claims, 39 Drawing Sheets

U.S. PATENT DOCUMENTS

| | | |
|---|---|---|
| 1,461,524 A | 7/1923 | Goddard |
| 2,579,192 A | 12/1951 | Kohl et al. |
| 2,646,298 A | 7/1953 | Leary |
| 2,607,624 A | 12/1954 | Thomas et al. |
| 2,734,299 A | 2/1956 | Masson |
| 2,825,592 A | 3/1958 | Sempie |
| 3,326,586 A | 6/1967 | Frost et al. |
| 3,470,834 A | 10/1969 | Bone |
| 3,521,918 A | 7/1970 | Hammond |
| 3,571,864 A | 3/1971 | Oger |
| 3,664,435 A | 5/1972 | Klessig |
| 3,675,639 A | 7/1972 | Cimber |
| 3,713,680 A | 1/1973 | Pagano |
| 3,756,638 A | 9/1973 | Stockberger |
| 3,873,140 A | 3/1975 | Bloch |
| 3,931,667 A | 1/1976 | Merser et al. |
| 3,976,079 A | 8/1976 | Samuels et al. |
| 4,006,747 A | 2/1977 | Kronenthal et al. |
| 4,060,089 A | 11/1977 | Noiles |
| 4,133,315 A | 1/1979 | Berman et al. |
| 4,210,148 A | 7/1980 | Stivala |
| 4,246,893 A | 1/1981 | Berson |
| 4,291,698 A | 9/1981 | Fuchs et al. |
| 4,328,805 A | 5/1982 | Akopov et al. |
| 4,416,267 A | 11/1983 | Garren et al. |
| 4,458,681 A | 7/1984 | Hophins |
| 4,472,226 A | 9/1984 | Redinger et al. |
| 4,485,805 A | 12/1984 | Foster, Jr. et al. |
| 4,493,323 A | 1/1985 | Albright et al. |
| 4,558,699 A | 12/1985 | Bashour |
| 4,592,339 A | 6/1986 | Kuzmak et al. |
| 4,592,342 A | 6/1986 | Salmasian |
| 4,621,640 A | 11/1986 | Mulhollan et al. |
| 4,669,473 A | 6/1987 | Richards et al. |
| 4,694,827 A | 9/1987 | Weiner et al. |
| 4,696,288 A | 9/1987 | Kuzmak et al. |
| 4,705,040 A | 11/1987 | Mueller et al. |
| 4,714,281 A | 12/1987 | Peck |
| 4,723,547 A | 2/1988 | Kullas et al. |
| 4,738,255 A | 4/1988 | Goble et al. |
| 4,739,758 A | 4/1988 | Lai et al. |
| 4,744,364 A | 5/1988 | Kensey |
| 4,750,492 A | 6/1988 | Jacobs |
| 4,803,985 A | 2/1989 | Hill |
| 4,823,794 A | 4/1989 | Pierce |
| 4,899,747 A | 2/1990 | Garren et al. |
| 4,955,913 A | 9/1990 | Robinson |
| 5,002,550 A | 3/1991 | Li |
| 5,033,481 A | 7/1991 | Heyler, III |
| 5,041,129 A | 8/1991 | Hayhurst et al. |
| 5,084,061 A | 1/1992 | Gau et al. |
| 5,100,421 A | 3/1992 | Christoudias |
| 5,112,310 A | 5/1992 | Grobe |
| 5,123,914 A | 6/1992 | Cope |
| 5,129,912 A | 7/1992 | Noda et al. |
| RE34,021 E | 8/1992 | Mueller et al. |
| 5,151,086 A | 9/1992 | Duh et al. |
| 5,188,104 A | 2/1993 | Wernicke et al. |
| 5,217,470 A | 6/1993 | Weston |
| 5,234,454 A | 8/1993 | Bangs |
| 5,246,456 A | 9/1993 | Wilkinson |
| 5,258,015 A | 11/1993 | Li et al. |
| 5,259,399 A | 11/1993 | Brown |
| 5,269,809 A | 12/1993 | Hayhurst et al. |
| 5,292,344 A | 3/1994 | Douglas |
| 5,334,200 A | 8/1994 | Johnson |
| 5,354,271 A | 10/1994 | Voda |
| 5,364,408 A | 11/1994 | Gordon |
| 5,391,182 A | 2/1995 | Chin |
| 5,405,352 A | 4/1995 | Weston |
| 5,423,872 A | 6/1995 | Cigaina |
| 5,428,123 A | 6/1995 | Ward et al. |
| 5,433,723 A | 7/1995 | Lindenberg et al. |
| 5,445,608 A | 8/1995 | Chen et al. |
| 5,470,337 A | 11/1995 | Moss |
| 5,472,446 A | 12/1995 | Torre |
| 5,480,406 A | 1/1996 | Nolan et al. |
| 5,496,311 A | 3/1996 | Abele et al. |
| 5,507,754 A | 4/1996 | Green et al. |
| 5,545,171 A | 8/1996 | Sharkey et al. |
| 5,545,178 A | 8/1996 | Kensey et al. |
| 5,549,621 A | 8/1996 | Bessler et al. |
| 5,554,162 A | 9/1996 | DeLange |
| 5,573,540 A | 11/1996 | Yoon |
| 5,591,177 A | 1/1997 | Lehrer |
| 5,601,604 A | 2/1997 | Vincent |
| 5,626,614 A | 5/1997 | Hart |
| 5,634,936 A | 6/1997 | Linden et al. |
| 5,647,836 A | 7/1997 | Blake, III et al. |
| 5,690,691 A | 11/1997 | Chen et al. |
| 5,716,368 A | 2/1998 | Torre et al. |
| 5,725,557 A | 3/1998 | Gatturna et al. |
| 5,846,254 A | 12/1998 | Schulze et al. |
| 5,888,196 A | 3/1999 | Bonutti |
| 5,931,788 A | 8/1999 | Keen et al. |
| 5,938,669 A | 8/1999 | Klaiber et al. |
| 5,951,590 A | 9/1999 | Goldfarb |
| 5,961,440 A | 10/1999 | Schweich, Jr. et al. |
| 5,971,447 A | 10/1999 | Steck, III |
| 5,993,473 A | 11/1999 | Chan et al. |
| 6,013,053 A | 1/2000 | Bower et al. |
| 6,067,991 A | 5/2000 | Forsell |
| 6,080,160 A | 6/2000 | Chen et al. |
| 6,097,984 A | 8/2000 | Douglas |
| 6,102,922 A | 8/2000 | Jakobsson et al. |
| 6,113,609 A | 9/2000 | Adams |
| 6,143,006 A | 11/2000 | Chan |
| 6,162,234 A | 12/2000 | Freedland et al. |
| 6,186,149 B1 | 2/2001 | Pacella et al. |
| 6,270,530 B1 | 8/2001 | Eldridge et al. |
| 6,420,452 B1 | 7/2002 | Gunatillake et al. |
| 6,437,073 B1 | 8/2002 | Gunatillake et al. |
| 6,447,533 B1 | 9/2002 | Adams |
| 6,454,785 B2 | 9/2002 | De Hoyos Garza |
| 6,475,136 B1 | 11/2002 | Forsell |
| 6,488,691 B1 | 12/2002 | Carroll et al. |
| 6,491,707 B2 | 12/2002 | Makower et al. |
| 6,494,888 B1 | 12/2002 | Laufer et al. |
| 6,500,148 B1 | 12/2002 | Pinchuk et al. |
| 6,506,196 B1 | 1/2003 | Laufer |
| 6,511,490 B2 | 1/2003 | Robert et al. |
| 6,535,764 B2 | 3/2003 | Imran et al. |
| 6,558,400 B2 | 5/2003 | Deem et al. |
| 6,656,182 B1 | 12/2003 | Hayhurst |
| 6,663,639 B1 | 12/2003 | Laufer et al. |
| 6,669,713 B2 | 12/2003 | Adams |
| 6,675,809 B2 | 1/2004 | Stack et al. |
| 6,736,793 B2 | 5/2004 | Meyer et al. |
| 6,746,460 B2 | 6/2004 | Gannoe et al. |
| 6,755,869 B2 | 6/2004 | Geitz |
| 6,773,441 B1 | 8/2004 | Laufer et al. |
| 6,790,213 B2 | 9/2004 | Cherok et al. |
| 6,821,285 B2 | 11/2004 | Laufer et al. |
| 6,835,200 B2 | 12/2004 | Laufer et al. |
| 6,869,395 B2 | 3/2005 | Page et al. |
| 6,900,055 B1 | 5/2005 | Fuller |
| 6,908,487 B2 | 6/2005 | Cigaina |
| 6,981,978 B2 | 1/2006 | Gannoe |
| 6,994,715 B2 | 2/2006 | Gannoe et al. |
| 7,033,373 B2 | 4/2006 | De la Torre et al. |
| 7,037,344 B2 | 5/2006 | Kagan et al. |
| 7,153,314 B2 | 12/2006 | Laufer et al. |
| 7,167,750 B2 | 1/2007 | Knudson et al. |
| 7,223,277 B2 | 5/2007 | DeLegge |
| 7,255,675 B2 | 8/2007 | Gertner et al. |
| 7,310,557 B2 | 12/2007 | Maschino et al. |
| 7,334,822 B1 | 2/2008 | Hines, Jr. |
| 7,338,433 B2 | 3/2008 | Coe |
| 7,354,454 B2 | 4/2008 | Stack et al. |
| 7,374,565 B2 | 5/2008 | Hassler et al. |
| 7,402,166 B2 | 7/2008 | Feigl |
| 7,416,554 B2 | 8/2008 | Lam et al. |
| 7,534,248 B2 | 5/2009 | Mikkaichi et al. |
| 7,618,426 B2 | 11/2009 | Ewers et al. |
| 7,666,195 B2 | 2/2010 | Kelleher et al. |
| 7,670,279 B2 * | 3/2010 | Gertner .......... 600/37 |
| 7,775,967 B2 | 8/2010 | Gertner |

| | | |
|---|---|---|
| 7,841,978 B2 | 11/2010 | Gertner |
| 7,850,660 B2 | 12/2010 | Uth et al. |
| 7,862,546 B2 | 1/2011 | Conlon et al. |
| 7,988,617 B2 * | 8/2011 | Gertner .......................... 600/37 |
| 2001/0010005 A1 | 7/2001 | Kammerer et al. |
| 2001/0011543 A1 | 8/2001 | Forsell |
| 2001/0044639 A1 | 11/2001 | Levinson |
| 2002/0055757 A1 | 5/2002 | Torre et al. |
| 2002/0128684 A1 | 9/2002 | Foerster |
| 2002/0161382 A1 | 10/2002 | Neisz et al. |
| 2002/0161414 A1 | 10/2002 | Flesler et al. |
| 2002/0188354 A1 | 12/2002 | Peghini et al. |
| 2003/0021822 A1 | 1/2003 | Lloyd |
| 2003/0055463 A1 | 3/2003 | Gordon et al. |
| 2003/0055465 A1 | 3/2003 | Ben-Haim et al. |
| 2003/0093117 A1 | 5/2003 | Saadat |
| 2003/0208212 A1 | 11/2003 | Cigaina |
| 2004/0006351 A1 | 1/2004 | Gannoe et al. |
| 2004/0024386 A1 | 2/2004 | Deem et al. |
| 2004/0030347 A1 | 2/2004 | Gannoe et al. |
| 2004/0044353 A1 | 3/2004 | Gannoe |
| 2004/0044357 A1 | 3/2004 | Gannoe |
| 2004/0054352 A1 | 3/2004 | Adams et al. |
| 2004/0059289 A1 | 3/2004 | Garza Alvarez |
| 2004/0068224 A1 | 4/2004 | Couvillon et al. |
| 2004/0092892 A1 | 5/2004 | Kagan et al. |
| 2004/0097986 A1 | 5/2004 | Adams |
| 2004/0098060 A1 | 5/2004 | Ternes |
| 2004/0116949 A1 | 6/2004 | Ewers et al. |
| 2004/0122456 A1 | 6/2004 | Saadat et al. |
| 2004/0122473 A1 | 6/2004 | Ewers et al. |
| 2004/0148034 A1 | 7/2004 | Kagal et al. |
| 2004/0186503 A1 | 9/2004 | Delegge |
| 2004/0193194 A1 | 9/2004 | Laufer et al. |
| 2004/0194790 A1 | 10/2004 | Laufer et al. |
| 2004/0243178 A1 | 12/2004 | Haut et al. |
| 2004/0243179 A1 | 12/2004 | Foerster |
| 2004/0243180 A1 | 12/2004 | Donnelly et al. |
| 2004/0260345 A1 | 12/2004 | Foerster |
| 2004/0267378 A1 | 12/2004 | Gazi et al. |
| 2005/0022827 A1 | 2/2005 | Woo et al. |
| 2005/0049718 A1 | 3/2005 | Dann et al. |
| 2005/0096638 A1 | 5/2005 | Starkebaum et al. |
| 2005/0159769 A1 | 7/2005 | Alverdy |
| 2005/0197687 A1 | 9/2005 | Molaei et al. |
| 2005/0203344 A1 | 9/2005 | Orban, III et al. |
| 2005/0216040 A1 | 9/2005 | Gertner et al. |
| 2005/0216042 A1 | 9/2005 | Gertner |
| 2005/0222638 A1 | 10/2005 | Foley et al. |
| 2005/0228415 A1 | 10/2005 | Gertner et al. |
| 2005/0261712 A1 | 11/2005 | Balbierz |
| 2005/0267405 A1 | 12/2005 | Shah |
| 2005/0267406 A1 | 12/2005 | Hassler et al. |
| 2005/0267533 A1 | 12/2005 | Gertner |
| 2005/0267595 A1 | 12/2005 | Chen et al. |
| 2005/0267596 A1 | 12/2005 | Chen et al. |
| 2005/0277960 A1 | 12/2005 | Hassler, Jr. et al. |
| 2005/0277974 A1 | 12/2005 | Hassler, Jr. et al. |
| 2006/0009789 A1 | 1/2006 | Gambale et al. |
| 2006/0025789 A1 | 2/2006 | Laufer et al. |
| 2006/0025819 A1 | 2/2006 | Nobis et al. |
| 2006/0030884 A1 | 2/2006 | Yeung et al. |
| 2006/0058829 A1 | 3/2006 | Sampson et al. |
| 2006/0089571 A1 | 4/2006 | Gertner |
| 2006/0089646 A1 | 4/2006 | Bonutti |
| 2006/0106288 A1 | 5/2006 | Roth et al. |
| 2006/0161186 A1 | 7/2006 | Hassler, Jr. et al. |
| 2006/0161256 A1 | 7/2006 | Ziegler et al. |
| 2006/0195139 A1 | 8/2006 | Gertner |
| 2006/0212053 A1 | 9/2006 | Gertner |
| 2006/0253131 A1 | 11/2006 | Wolniewicz |
| 2006/0264699 A1 | 11/2006 | Gertner |
| 2006/0265042 A1 | 11/2006 | Catanese, III et al. |
| 2006/0276871 A1 | 12/2006 | Lamson et al. |
| 2006/0282081 A1 | 12/2006 | Fanton et al. |
| 2007/0027358 A1 | 2/2007 | Gertner et al. |
| 2007/0049970 A1 | 3/2007 | Belef et al. |
| 2007/0060940 A1 | 3/2007 | Brazzini et al. |
| 2007/0073318 A1 | 3/2007 | Carter et al. |
| 2007/0073323 A1 | 3/2007 | Carter et al. |
| 2007/0088373 A1 | 4/2007 | Baker et al. |
| 2007/0112363 A1 | 5/2007 | Adams et al. |
| 2007/0112385 A1 | 5/2007 | Conlon |
| 2007/0129738 A1 | 6/2007 | Kraemer et al. |
| 2007/0167982 A1 | 7/2007 | Gertner et al. |
| 2007/0173869 A1 | 7/2007 | Gannoe et al. |
| 2007/0173888 A1 | 7/2007 | Gertner et al. |
| 2007/0179335 A1 | 8/2007 | Gertner et al. |
| 2007/0203517 A1 | 8/2007 | Williams et al. |
| 2007/0233170 A1 | 10/2007 | Gertner et al. |
| 2007/0235083 A1 | 10/2007 | Dlugos |
| 2007/0239284 A1 | 10/2007 | Skerven et al. |
| 2007/0250103 A1 | 10/2007 | Makower |
| 2007/0255308 A1 | 11/2007 | Williams et al. |
| 2007/0260259 A1 | 11/2007 | Fanton et al. |
| 2007/0270892 A1 | 11/2007 | Makower |
| 2007/0276293 A1 | 11/2007 | Gertner |
| 2007/0276432 A1 | 11/2007 | Stock |
| 2008/0015501 A1 | 1/2008 | Gertner |
| 2008/0033488 A1 | 2/2008 | Catanese, III et al. |
| 2008/0039894 A1 | 2/2008 | Catanese, III et al. |
| 2008/0051823 A1 | 2/2008 | Makower et al. |
| 2008/0051824 A1 | 2/2008 | Gertner |
| 2008/0051850 A1 | 2/2008 | Sparks et al. |
| 2008/0058710 A1 | 3/2008 | Wilk |
| 2008/0071306 A1 | 3/2008 | Gertner |
| 2008/0086082 A1 | 4/2008 | Brooks |
| 2008/0091237 A1 | 4/2008 | Schwartz et al. |
| 2008/0109027 A1 | 5/2008 | Chen et al. |
| 2008/0147002 A1 | 6/2008 | Gertner |
| 2008/0161717 A1 | 7/2008 | Gertner |
| 2008/0167519 A1 | 7/2008 | St-Germain |
| 2008/0167647 A1 | 7/2008 | Gertner |
| 2008/0167648 A1 | 7/2008 | Gertner |
| 2008/0172074 A1 | 7/2008 | Baker et al. |
| 2008/0172079 A1 | 7/2008 | Birk |
| 2008/0208240 A1 | 8/2008 | Paz |

FOREIGN PATENT DOCUMENTS

| | | |
|---|---|---|
| EP | 1 520 563 | 4/2005 |
| EP | 1 602 392 A1 | 7/2005 |
| EP | 1 591 140 A1 | 11/2005 |
| EP | 1 547 642 B1 | 8/2007 |
| EP | 1 607 071 B1 | 8/2007 |
| EP | 1 670 361 B1 | 4/2008 |
| FR | 2 907 665 | 5/2008 |
| WO | WO 87/00034 | 1/1987 |
| WO | WO 99/25418 | 5/1999 |
| WO | WO 9925418 | 5/1999 |
| WO | WO 00/09049 | 2/2000 |
| WO | WO 00/18330 | 4/2000 |
| WO | WO 00/74573 A1 | 12/2000 |
| WO | WO 01/47435 | 7/2001 |
| WO | WO 02/35980 | 5/2002 |
| WO | WO 02071951 | 9/2002 |
| WO | WO 03/055420 | 7/2003 |
| WO | WO 03095015 | 11/2003 |
| WO | WO 2004004542 | 1/2004 |
| WO | WO 2004014237 | 2/2004 |
| WO | WO 2004019765 | 3/2004 |
| WO | WO 2004021894 | 3/2004 |
| WO | WO 2004/037064 | 5/2004 |
| WO | WO 2005007232 | 1/2005 |
| WO | WO 2005/009288 | 2/2005 |
| WO | WO 2005/018417 A2 | 3/2005 |
| WO | WO 2005/018417 A3 | 3/2005 |
| WO | WO 2005018417 | 3/2005 |
| WO | WO 2005020802 | 3/2005 |
| WO | WO 2005/094447 A2 | 10/2005 |
| WO | WO 2006/020370 | 2/2006 |
| WO | WO 2006/049725 A2 | 5/2006 |
| WO | WO 2006/063593 A2 | 6/2006 |
| WO | WO 2006/108203 | 10/2006 |
| WO | WO 2006127431 | 11/2006 |
| WO | WO 2006134106 A1 | 12/2006 |
| WO | WO 2007/017880 A2 | 2/2007 |
| WO | WO 2007/067206 A2 | 6/2007 |
| WO | WO 2007064906 A2 | 6/2007 |

| | | |
|---|---|---|
| WO | WO 2007/110866 A2 | 10/2007 |
| WO | WO 2008013814 | 1/2008 |
| WO | WO 2008/006084 A2 | 9/2008 |

OTHER PUBLICATIONS

Buckwald—Overview of Bariatric Surgery. Journal of the American College of Surgeons. pp. 367-375, Mar. 2002.
Sharp, et al., The 4-S Modification of the Roeder Knot: How to Tie It. pp. 1004-1006, vol. 90, No. 6, Dec. 1997.
Buchwald et al., "Bariatric Surgery: A Systematic Review and Meta-analysis", JAMA 2004, vol. 292, No. 14, pp. 1724-1737.
Buchwald et al., "Evolution of Operative Procedures for the Management of Morbid Obesity 1950-2000", Obesity Surgery 2002, 12:705-717.
Camerini et al., "Thirteen Years of Follow-up in Patients with Adjustable Silicone Gastric Banding for Obesity: Weight Loss and Constant Rate of Late Specific Complications" Obesity Surgery 2004, 14:1343-1348.
Cope et al., "Percutaneous Transgastric Technique for Creating Gastroenteric Anastomoses in Swine", Journal of Vascular and Interventional Radiology, 2004, 15:177-181.
Cummings et al., "Genetics and Pathophysiology of Human Obesity", An Annual Review of Medicine, 2003, 54:453-417/.
Johnston et al., "The Magenstrasse and Mill Operation for Morbid Obesity", Obesity Surgery 2003, 13:10-16.
Morino et al., "Laparoscopic Adjustable Silicone Gastric Banding Versus Vertical Banded Gastroplasty in Morbidly Obese Patients" Analysis Obesity Surgery vol. 238, No. 6, 2003, pp. 835-842.
Roman et al., "Intragastric Balloon of Non-Morbid Obesity: A Retrospective Evaluation of Tolerance and Efficacy", Obesity Surgery, 2004, 14:539-544.
Sallet et al., Brazillian Multicenter Study of the Intragastric Ballon; Obesity Surgery, 2004, 14, pp. 991-998.
Sjostrom et al., Lifestyle, Diabeters, and Cardavascular Risk Factors 10 years after Bariatric Surgery, New England Journal of Medicine, 2004, 351, (6) 2683-2693.
Smith at al., "Modification of the Gastric Partitioning Operation for Morbid Obesity", Am. J Surgery 142, Dec. 1981 pp. 725-730.
Smith et al., "Results and Complications of Gastric Partition: Four Years Follow-Up of 300 Morbidy Obese Patients", The American Journal of Surgery, 1983, (146) pp. 815-819.
Trumble et al., "Method for measuring long-term function of muscle-powered implants via radiotelemetry" J. Appl. Physiol. 2001,90: pp. 1977-1985.
About the Vertical Sleeve Gastrectomy. Mar. 24, 2006, pp. 1-1. http://obesityhelp.com/forums/VSG/about.html.
Akira., JP63277063, Japanese and English Abstract, Nov. 15, 1988, pp. 1-4.
Abhyankar et al, Use of a tissue expander and a polyglactic acid (Vicryl) mesh to reduce radiation enteritis: case report and literature view, 21: pp. 755-757, Aug. 2005.
Buchwald, Overview of Bariatric Surgery, vol. 194, No. 3, Mar. 2002, pp. 367-375.
Burnett, et al., The Use of a Pelvic Displacement Prosthesis to Exclude the Small Intestine from the Radiation Field Following Radical Hysterectomy, 79, pp. 438-443, 2000. http://www.idealibrary.com.
Brolin, Robert E., Gastric Bypass. vol. 81, No. 5, Oct. 2001, pp. 1077-1095.
Cheng, Splenic Epidermoid Cyst, pp. 1-3, 1997.

DeMaria, Eric J., Laparoscopic Adjustable Silicone Gastric Banding. vol. 81, No. 5, Oct. 2001, pp. 1129-1143.
Deitel,Mervyn., Overview of Operations for Morbid Obesity. vol. 22, No. 9, Sep. 1998, pp. 913-918.
Doherty, Cornelius., Technique of Vertical Banded Gastroplasty. vol. 81, No. 5, Oct. 2001, pp. 1097-1111.
Fried et al., Physical Principles of Available Adjustable Gastric Bands: How they Work. Obesity Surgery, 14, 2004, pp. 1118-1121.
Foglia et al., Management of giant omphalocele with rapid creation of abdominal domain, 41, pp. 704-709, 2006.
Geliebter et al; Extra-abdominal pressure alters food intake, intragastric pressure, and gastric emptying rate. 1986, pp. R549-R552.
Gertner MD, Stomach Restriction with an Extragastric Balloon, pp. 1, Abstract for 2007.
Hainaux et al,, Laparoscopic adjustable silicone gastric banding: radiological appearances of a new surgical treatment for morbid obesity. 1999. Abdom Imaging 24: 533-537.
Hoffman et al., Morbidity after Intraperitoneal Insertion of Saline-Filled Tissue Expanders for Small Bowel Exclusion from Radiotherapy Treatment Fields: A Prospective Four Year Experience with 34 Patients, pp. 473-483, No. 7, vol. 60, Jul. 1994.
Konturek et al., Neuro-Hormonal Control of Food Intake; Basic Mechanisms and Clinical Implications, 2005, 56, Supp 6, 5-25. www.jpp.krakow.pl.
Lam et al., Huge Splenic Epidemoid Cyst: A Case Report, 1997; 60:113-6.
Laparoscopic Duodenal Switch, Mar. 24, 2006, http://wo-pub2.med.cornell.edu/chi.bin/WebObjects/PublicA.woa/5/w . . . p. 1-1.
Lee et al., Laparoscopic Vertical Sleeve Gastrectomy: A Novel Bariatric Procedure-superior to Estabilished.
Operations? pp. 1-27. 90th Annual Clinical Congress, New Orleans, LA, Oct. 10, 2004. Med-4840, Product Profile , Mar. 30, 2007, pp. 1-2.
Malassagne, et al., Intra-abdonimal Sengstaken-Blakemore tube Placement for acute venous outflow obstruction in reduced-size Liver, Nov. 1996, 83, pp. 1086.
Marceau, et al., Malabsorptive Obesity Surgery. vol. 81, Oct. 2001, No. 5, pp. 1113-1127.
Mera, et al., Use of the Breast Implant for Liver Graft Malposition. vol. 5, No. 6, Nov. 1999, pp. 534-535.
Obesity Surgery Including Laparoscopy and Allied Care. vol. 16, No. 1, Jan. 2006, pp. 1-2. www.obesitysurgey.com.
Pomerri et al., Adjustable Silicone Gastric Banding of Obesity. , 1992, Gastrointest Radiol 17: pp. 207-210.
Schauer, et al., New applications for endoscopy: the emerging field of endoluminal and transgastric bariatric surgery, DOI:10.1007/s00464-006-9008-8, 2006.
The Sleeve Gastrectomy (or 2-Stage Procedure). 2006, pp. 1-2. http://surgicallyslim.com/sleeve.htm.
Tucker, Diana, Medical Device Daily. vol. 10, No. 102, pp. 1-10, May 26, 2006.
Walker, et al. Bladder Augmentation in Dogs Using the Tissue Capsule Formed Around a Perivesical tissue Expander, vol. 168, pp. 1534-1536, 2002.
Zwart et al., Gastric Motility: Comparison of Assessement with Real-Time MR Imaging or Barostat Experience1., 224: pp. 592-597, Aug. 2002.

* cited by examiner

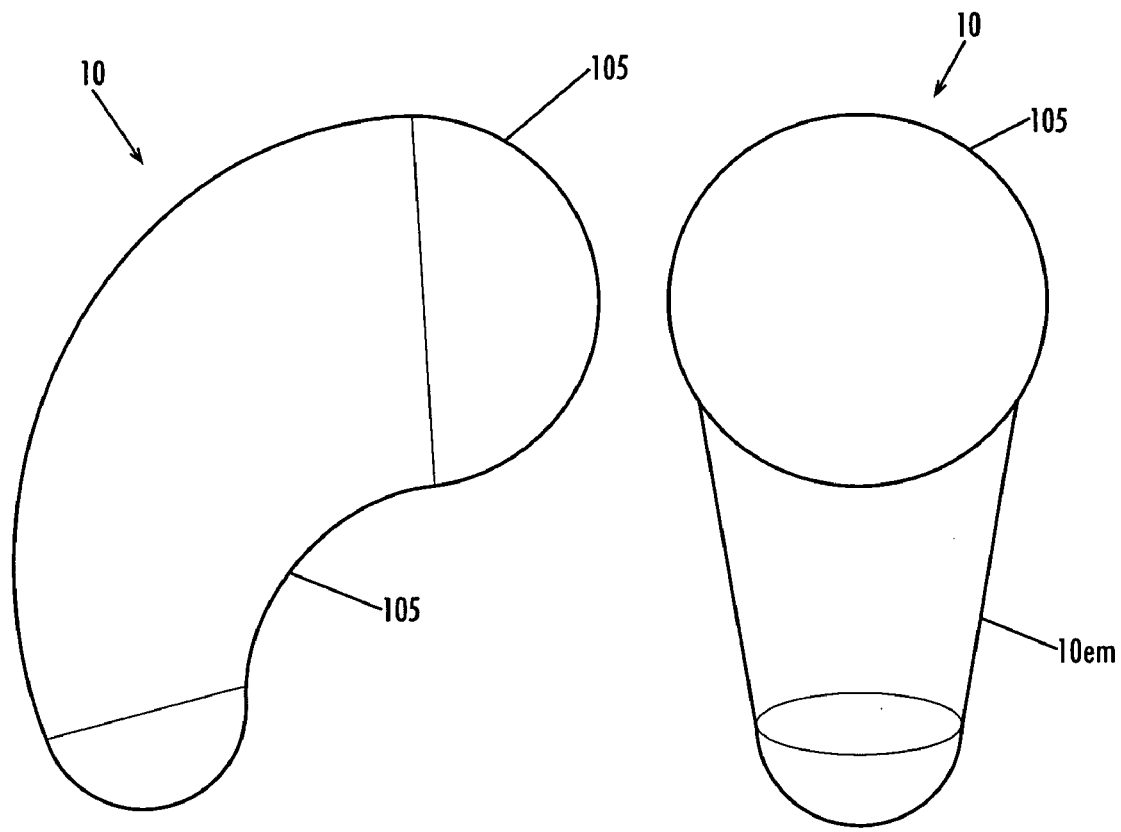
Fig. 3A  Fig. 3B
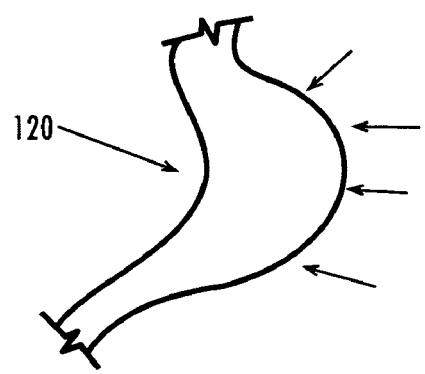
Fig. 4

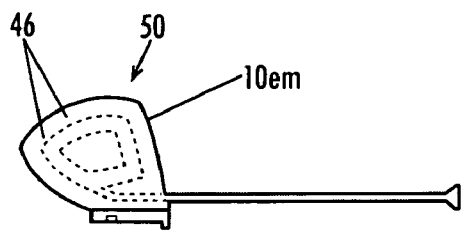
Fig. 10B
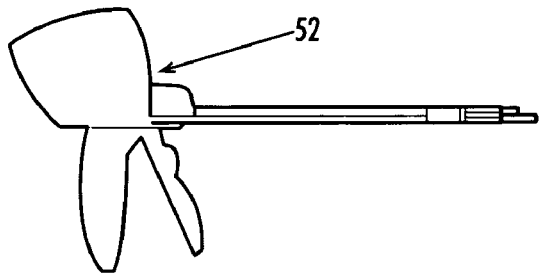
Fig. 10C
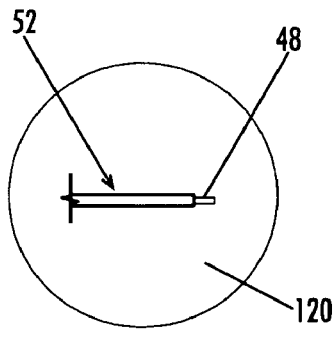 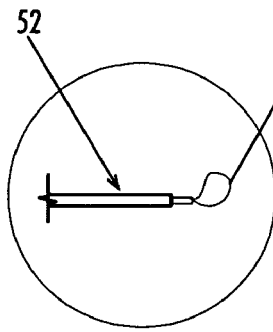 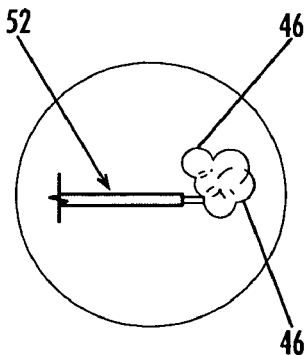
Fig. 10D   Fig. 10E   Fig. 10F

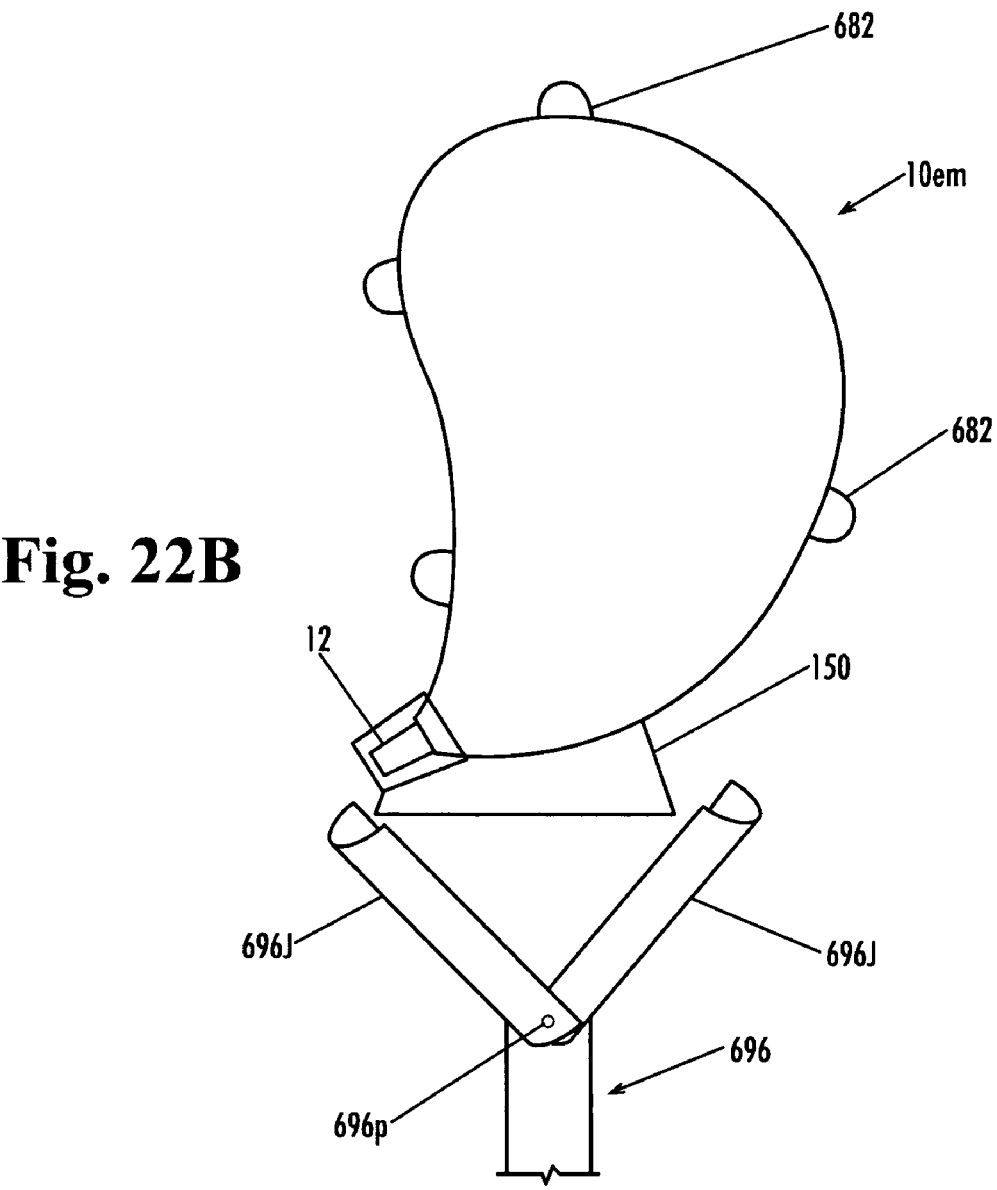
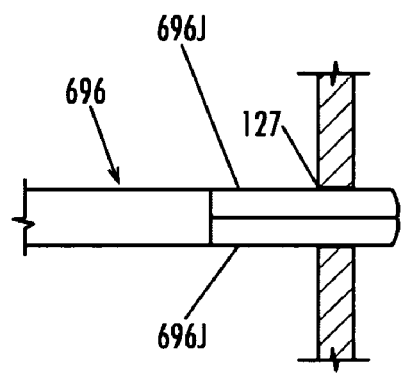
Fig. 22B
Fig. 22C

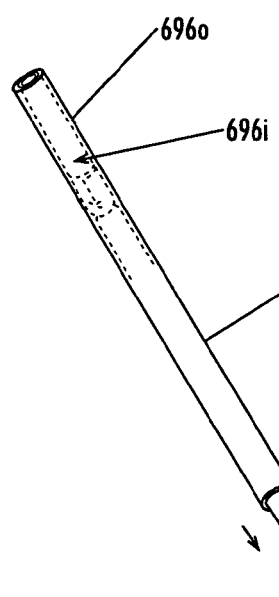 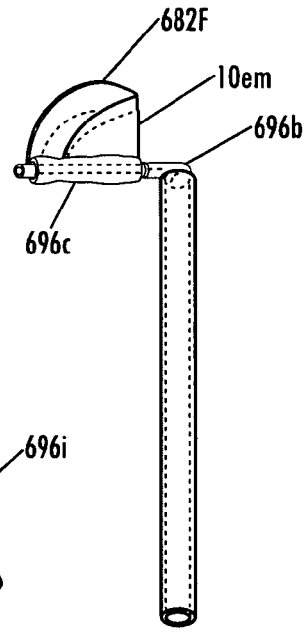 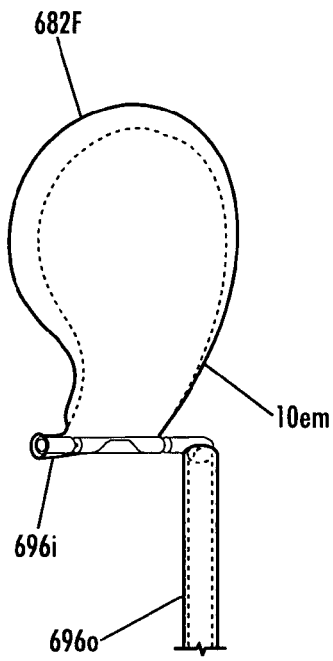
Fig. 22F   Fig. 22G   Fig. 22H
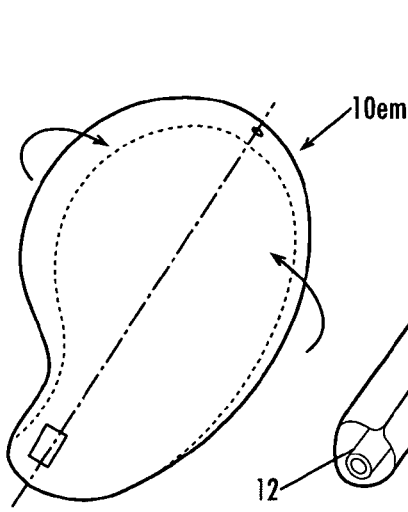 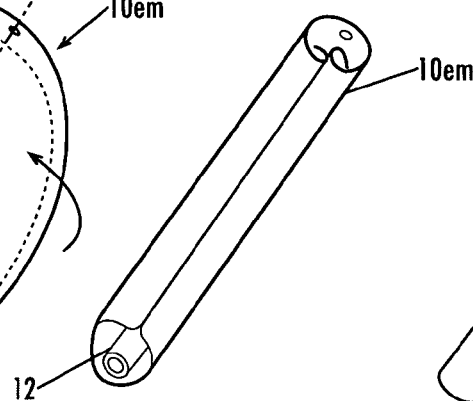 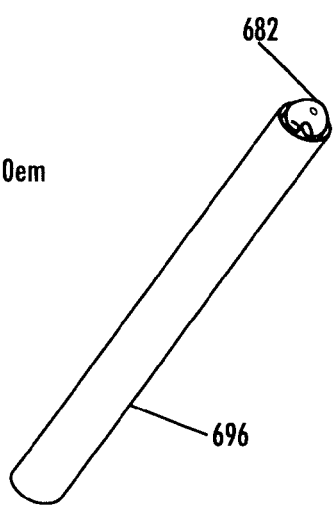
Fig. 22I   Fig. 22J   Fig. 22K

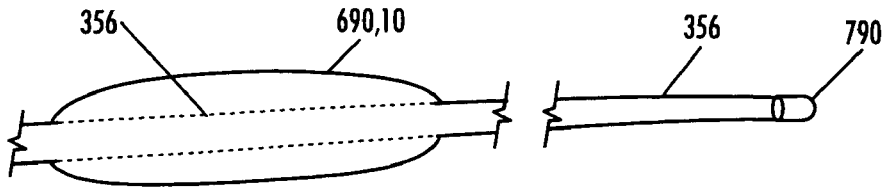
Fig. 22O
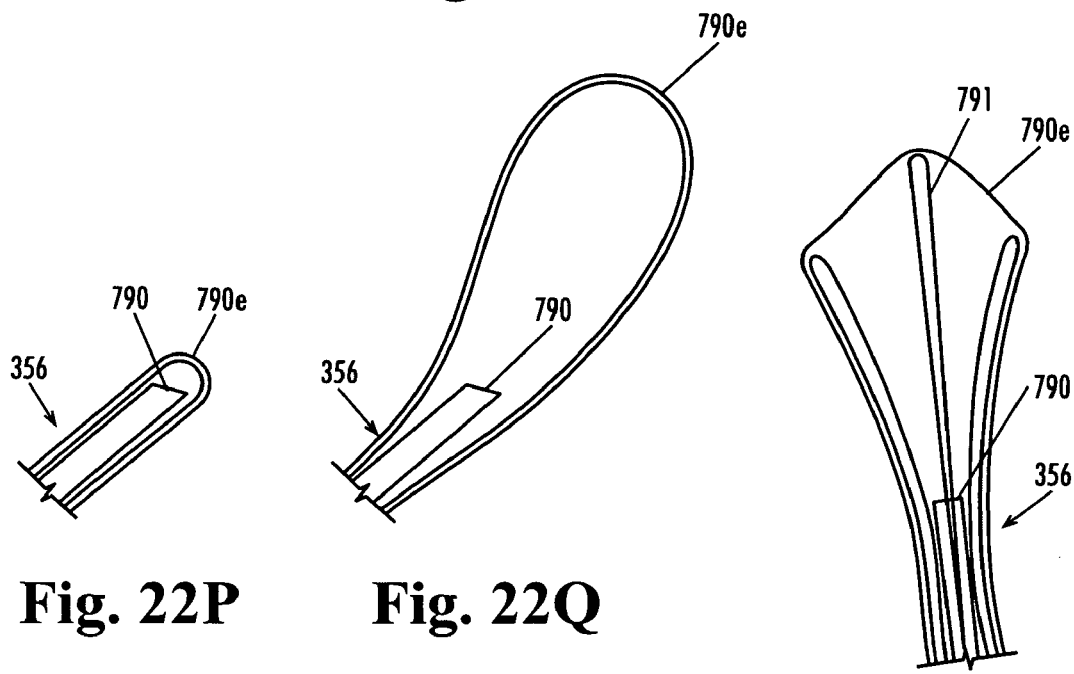
Fig. 22P  Fig. 22Q
Fig. 22R
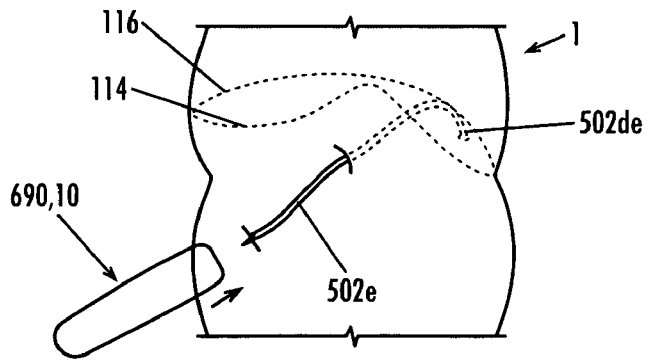
Fig. 22S

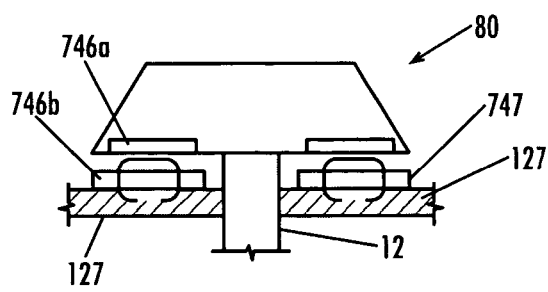
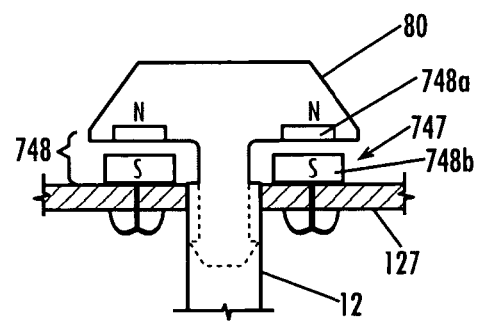
Fig. 25A        Fig. 25B
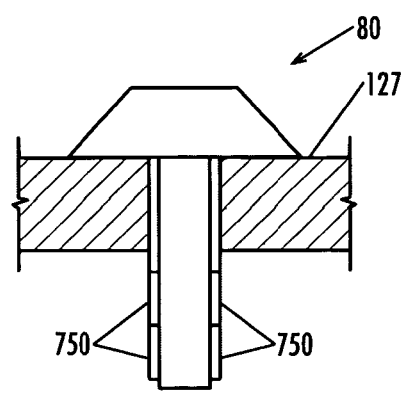
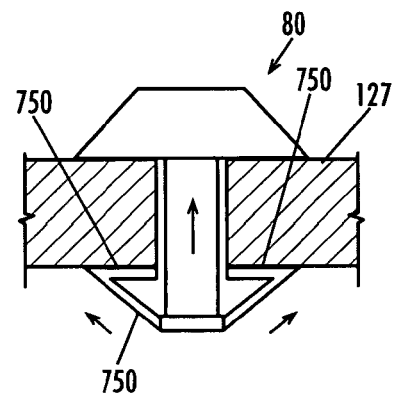
Fig. 25C        Fig. 25D
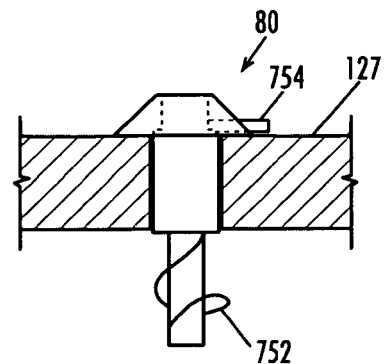
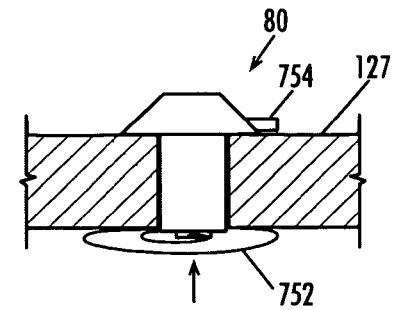
Fig. 25E        Fig. 25F

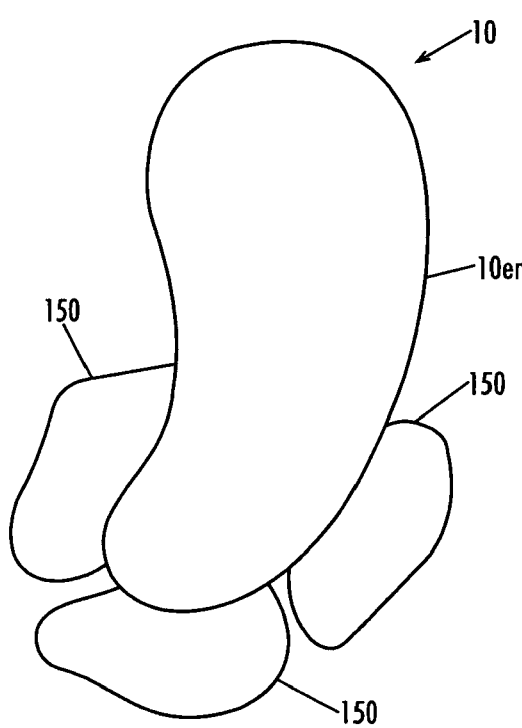
Fig. 27A
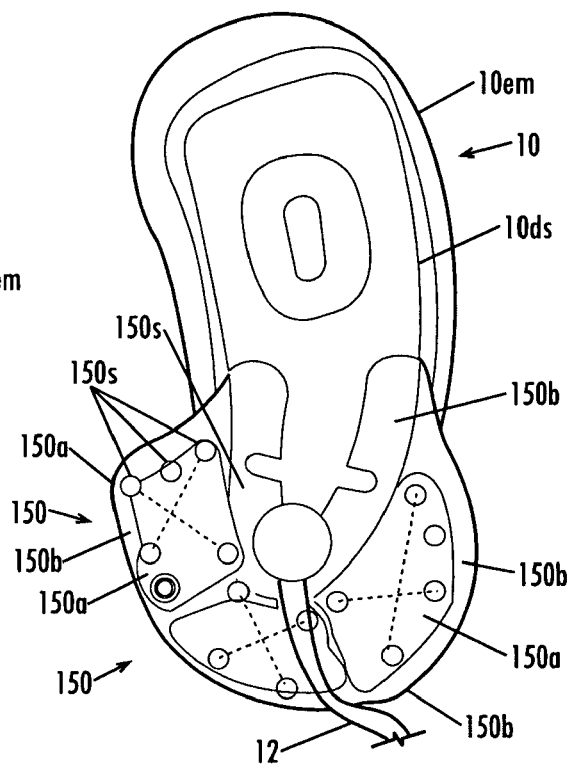
Fig. 27B
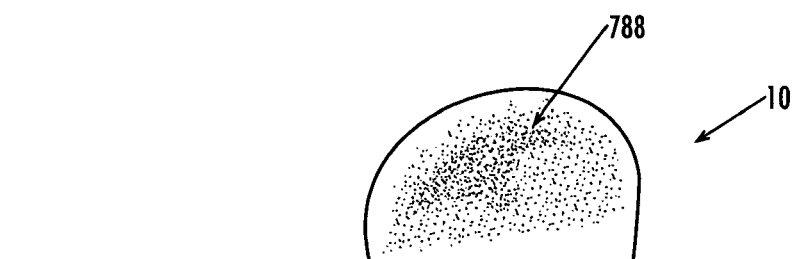
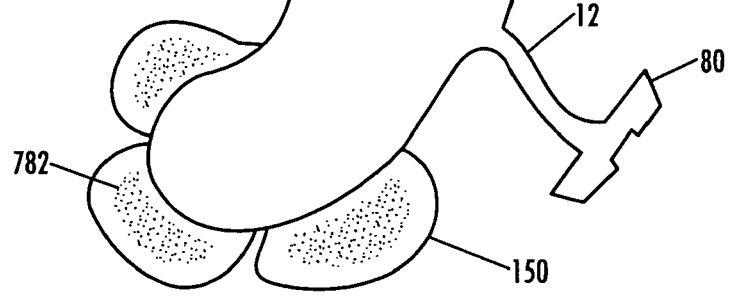
Fig. 27C

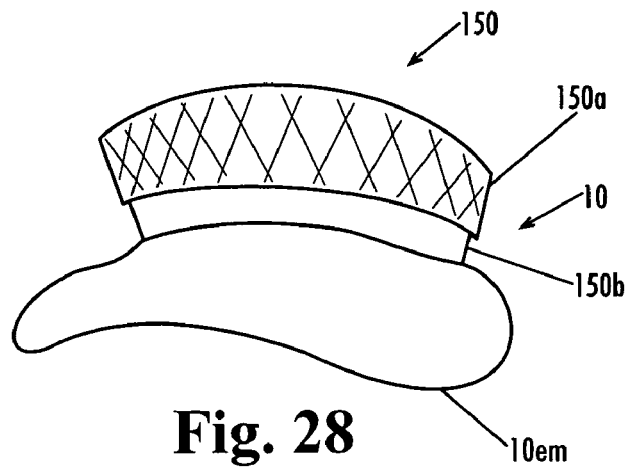
Fig. 28
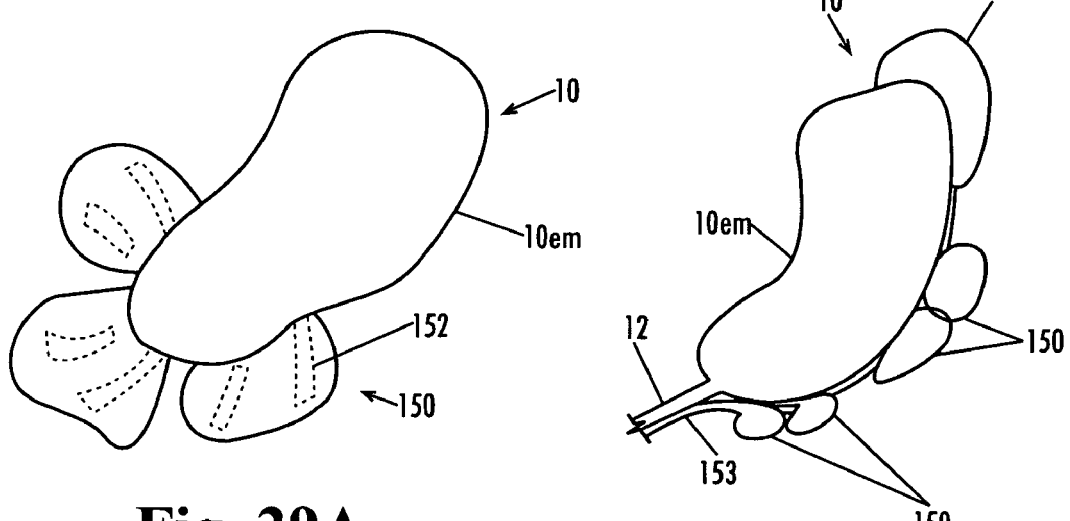
Fig. 29A
Fig. 29B
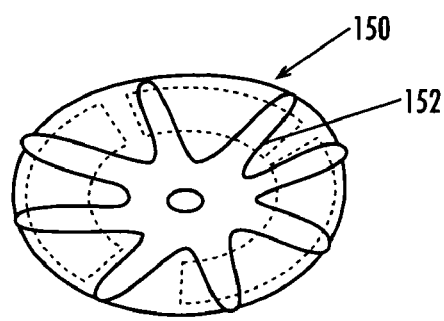
Fig. 29C
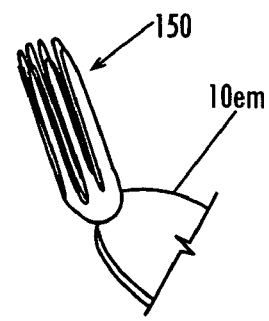
Fig. 29D

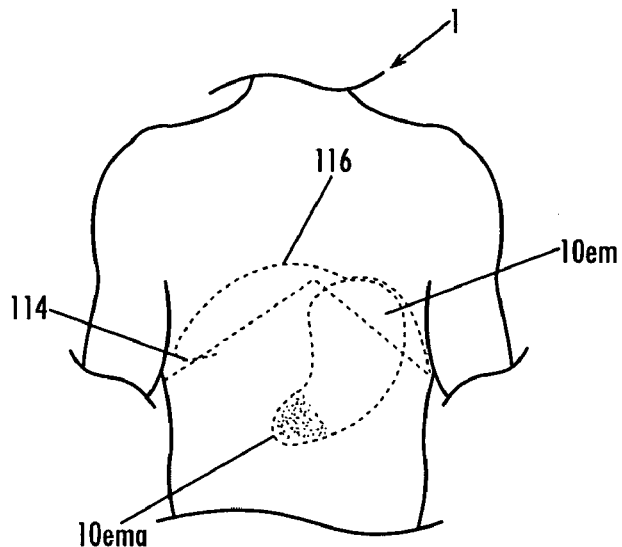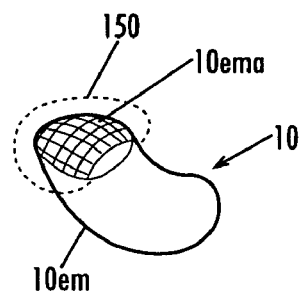
Fig. 30A  Fig. 30B
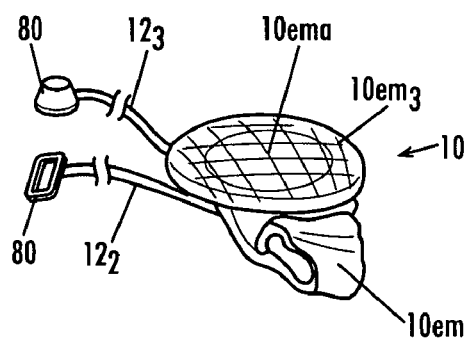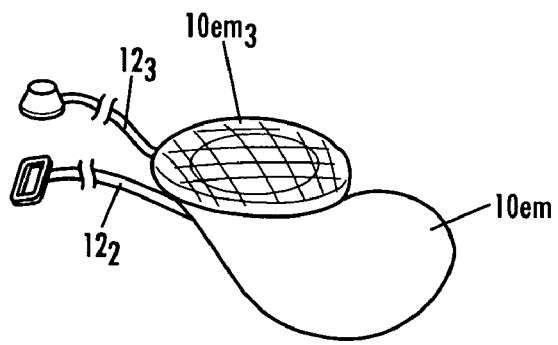
Fig. 31A  Fig. 31B
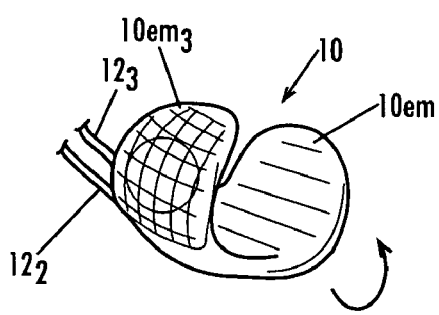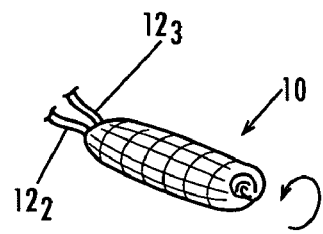
Fig. 31C  Fig. 31D

DEVICES AND METHODS FOR TREATMENT OF OBESITY

CROSS-REFERENCE

This application is a continuation of co-pending application Ser. No. 11/716,985, filed Mar. 10, 2007, which claims the benefit of U.S. Provisional Application No. 60/877,595, filed Dec. 28, 2006, and this application is a continuation-in-part application of co-pending application Ser. No. 11/407,701, filed Apr. 19, 2006, each of which are incorporated herein by reference thereto, in their entireties, and to which applications we claim priority under 35 USC §120, and 35 USC §119, respectively.

This application also hereby incorporates herein by reference thereto, in its entirety, co-pending application Ser. No. 11/716,986 filed on Mar. 10, 2007, and titled "Devices and Methods for Treatment of Obesity".

FIELD OF THE INVENTION

The present invention relates to treatment of obesity, more particularly to implantable devices and methods of implanting the devices in the abdominal cavity to treat an obese patient.

BACKGROUND OF THE INVENTION

Obesity has become a major health concern, both nationally and internationally. The National Center for Health Statistics (NCHS) estimates that over 120 million Americans are overweight, including about 56% of the adult population. Of these, about 52 million are considered obese, as measured by a body mass index (BMI) of 30% or greater. In Europe, an estimated 77 million people are obese, as measured by the same standard. This problem is not limited to western nations, as many developing countries are reported to have obesity rates over 75% of the adult population.

Co-morbidities that are associated with obesity include, but are not limited to type II Diabetes, high blood pressure, sleep apnea, stroke and arthritis, the symptoms of which often tend to be lessened or alleviated upon loss of weight by a person so affected.

In the U.S., options for treatment of obesity are currently quite limited. Current treatment methodologies typically rely upon surgically introducing a "malabsorptive" environment in the gastro-intestinal tract, a restrictive environment, or a combination of these. One available treatment method is gastric bypass surgery and another is referred to as gastric banding (one of these techniques is referred to as the LAP-BAND™ procedure). These procedures are limited to only those patients with a BMI over 40 (or over 35, with co-morbidities present).

Gastric bypass procedures incur a great deal of morbidity and create a malabsorptive state in the patient by bypassing a large portion of the intestines. Serious side effects, such as liver failure have been associated with this procedure, as well as chronic diarrhea. Another surgical procedure that has a high degree of morbidity associated with it is known as the "Gastric Bypass Roux-en-Y" procedure. This procedure reduces the capacity of the stomach by creating a smaller stomach pouch. The small space holds only about one ounce of fluid. A tiny stomach outlet is also surgically created to slow the speed at which food leaves the stomach. Staples are used to create a small (15 to 20 cc) stomach pouch, with the rest of the stomach being stapled completely shut and divided from the stomach pouch. The small intestine is divided just beyond the duodenum, brought up, and connected to the newly formed stomach pouch. In addition to the considerable morbidity associated with this procedure, other disadvantages include "dumping syndrome", where stomach contents are literally "dumped" rapidly into the small intestine which may lead to nausea, weakness, sweating, faintness, and diarrhea; hernias resulting from the surgery; gallstones; leakage of the connection between the pouch and the intestine; stretching of the pouch that was formed; nutritional deficiencies; and possible dehiscence of the staples.

The LAPBAND™ is a band that, when placed, encircles the fundus-cardia junction and is inflatable to constrict the same. It does not reduce the volume of the stomach, but rather restricts passage of food into the stomach, the theory being that the patient will feel satiety with a much smaller volume of food than previously. Although the LAPBAND™ procedure is less invasive than a gastric bypass procedure, it also typically achieves less weight loss. Further, it is not a simple procedure and requires a substantial amount of training by a surgeon to become proficient in performing the procedure. Also, a substantial amount of dissecting and suturing is required because the pathway by which the band is introduced is not an existing pathway, and must be established by dissection. Great care is required to avoid blood vessels and nerves that may be in the intended pathway to be created by the dissection. After placing the band around the fundus-cardia junction, the ends of the band must be connected together and then it must be cinched down into place. Additionally, complications such as erosion at the fundus-cardia junction, slippage of the band from its intended location, nausea/vomiting, gastroesophageal reflux, dysphagia and lack of effectiveness in causing weight loss have been reported.

Intragastric balloons have also been placed, in an attempt to fill a portion of the volume in the stomach, with the theory being that it will then require less food than previously, to give the patient a sensation of fullness or satiety. This procedure involves delivery of a balloon (typically, transorally) to the interior of the stomach and inflation of the balloon to take up a portion of the volume inside the stomach. However, intragastric balloons may also lead to complications such as obstruction, vomiting and/or mucosal erosion of the inner lining of the stomach. The balloon can break down over extended exposure to the stomach's acids, and in some cases, after breaking down, the balloon translated through the intestines and caused a bowel obstruction.

Gastrointestinal sleeves have been implanted to line the stomach and/or a portion of the small intestines to reduce the absorptive capabilities of the small intestine and/or to reduce the volume in the stomach, by reducing the available volume to the tubular structure of the graft running therethrough. Although weight loss may be effective while these types of devices are properly functioning, there are complications with anchoring the device within the stomach/GI tract, as the stomach and GI tract function to break down things that enter into them and to move/transport them through. Accordingly, the integrity of the anchoring of the device, as well as the device itself may be compromised over time by the acids and actions of the stomach and GI tract.

A sleeve gastrectomy is an operation in which the left side of the stomach is surgically removed. This results in a much reduced stomach which is substantially tubular and may take on the shape of a banana. This procedure is associated with a high degree of morbidity, as a large portion of the stomach is surgically removed. Additionally, there are risks of complications such as dehiscence of the staple line where the staples are installed to close the surgical incisions where the portion of the stomach was removed. Further, the procedure is not reversible.

In the laparoscopic duodenal switch, the size of the stomach is reduced in similar manner to that performed in a sleeve gastrectomy. Additionally, approximately half of the small intestine is bypassed and the stomach is reconnected to the shortened small intestine. This procedure suffers from the same complications as the sleeve gastrectomy, and even greater morbidity is associated with this procedure due to the additional intestinal bypass that needs to be performed. Still further, complications associated with malabsorption may also present themselves.

An inflatable gastric device is disclosed in U.S. Pat. No. 4,246,893, in which a balloon is inserted anteriorly of the stomach and posteriorly of the left lobe of the liver. The balloon is then inflated to compress the stomach so that it fills with less food that would ordinarily be possible. Not only does this device compress the stomach, but it also compresses the liver, as seen in FIG. 5 of the patent, which may cause complications with the liver function. Additionally, the balloon is simply placed into this location, and there is no assurance that it will not migrate and lose its effectiveness in compressing the stomach to the degree intended. Still further, the balloon is of a simple spherical design, and, as such, extends pressure outwardly in all directions, 360 degrees, in all planes. Accordingly, the liver is compressed just as much as the stomach is. Also, the compression forces against the stomach are not ideal, as the spherical balloon conformation does not match the conformation of the expanding stomach. The stomach is not spherical when expanded, or concave with a constant radius of curvature, but expands into a designated space that allows the fundus to expand preferentially more than other parts of the stomach.

Brazzini et al. in WO2005/18417 discloses at least two or more expandable devices used to treat obesity, in which the devices are inserted through the abdominal wall and anchored against the external surface of the stomach wall by an anchoring mechanism that extends through the stomach wall and fixes to the internal surface of the stomach wall.

U.S. Patent Publication No. 2005/0261712 to Balbierz et al. describes capturing a device against the outer surface of the stomach wall to form a restriction that appears to function similarly to the restriction imposed by the LAPBAND™. The anchoring of the devices disclosed relies upon placement of features against the internal wall of the stomach to form an interlock with the device which is placed against the external wall of the stomach.

U.S. Patent Publication Nos. 2005/0267533 and 2006/0212053 to Gertner disclose devices for treatment of obesity that use one or more anchoring mechanisms that are passed through the wall of the stomach to establish an anchor.

U.S. Pat. No. 6,981,978 to Gannoe discloses devices for reducing the internal cavity of the stomach to a much smaller volume, which may be used to carry out a bypass procedure. Stapling is employed to isolate the smaller volume in the stomach, and thus the same potential disadvantages are present as with other stapling procedures described herein.

U.S. Pat. No. 6,186,149 to Pacella et al. describes an occluder device that can be used as a dietary control device (see FIG. 8C). The occluder device is placed against the wall of the stomach and inflated to press inwardly on the stomach wall. A frame is wrapped around the stomach wall and is inflated to press against the stomach wall. However, there is no disclosure of how the frame might be adjusted to maintain a position relative to the stomach wall as the size of the stomach varies.

Gastric reduction techniques have been attempted, such as by inserting instruments trans-orally and reducing the volume of the stomach by stapling portions of it together. However, this technique is prone to failure due to the staples pulling through the tissues that they are meant to bind.

Techniques referred to as gastric pacing endeavor to use electrical stimulation to simulate the normal feedback mechanisms of a patient that signal the brain that the patient is full, or satiated. While these techniques are less invasive than some of the other existing treatments, statistics to date have shown that the amount of weight lost by using such techniques is less than satisfactory.

Currently marketed drugs for weight loss, such as XENICAL®, MERIDIA® and Phen fen have largely failed, due to unacceptable side effects and complications, and sometimes to an ineffective amount of weight loss. Other drugs that are on the horizon include ACCOMPLIA® and SYMLIN®, but these are, as yet, unproven.

The risk and invasiveness factors of currently available surgeries are often too great for a patient to accept to undergo surgical treatment for his/her obesity. Accordingly, there is a need for less invasive, yet effective surgical treatment procedures for morbidly obese patients (patients having a BMI of 35 or greater). Also, since the current surgical procedures are currently indicated only for those patients having a BMI of 40 or greater, or 35 or greater when co-morbidities are present, it would be desirable to provide a surgical procedure that would be available for slightly less obese patients, e.g., patients having a BMI of 30 to 35 who are not indicated for the currently available surgical procedures. It would further be desirable to provide a surgical procedure that would be indicated for obese patients having a BMI in the range of 30-35, as well as for more obese patients.

SUMMARY OF THE INVENTION

The present invention provides methods, devices, tools, instruments and systems for treating a patient to induce weight loss.

At least one method embodiment comprises the steps of: passing a device, including an expandable member in a collapsed configuration, through an opening in the skin of the patient, and into the abdominal cavity of the patient; anchoring at least a portion of the expandable member, relative to at least one structure in the abdominal cavity, without piercing the stomach; and expanding the expandable member to an expanded configuration in a space in the abdominal cavity to perform at least one of: prevention of expansion of the stomach of the patient into the space; and compression of a portion of the stomach.

A method of implanting a weight-loss treatment device by connecting the device to an anchoring frame is provided, including the steps of: passing the anchoring frame into the abdominal cavity of the patient; anchoring the anchoring frame to at least one structure in the abdominal cavity, without piercing the stomach; passing the device, including an expandable member in a compressed configuration, into the abdominal cavity of the patient; and passing the device over the anchoring frame to anchor the device to the anchoring frame.

A method of implanting a weight-loss treatment device by connecting the device to an anchoring frame is provided, including: passing the anchoring frame into the abdominal cavity of the patient; passing the device, including an expandable member in a collapsed configuration, into the abdominal cavity of the patient; and passing the device over the anchoring frame to mechanically lock the device to the anchoring frame and to anchor the anchoring frame to at least one structure in the abdominal cavity, without piercing the stomach.

An implantable device for inducing weight loss is provided, including: an expandable main body member configured to be positioned adjacent a portion of a stomach of a patient, within the abdominal cavity of the patient; the expandable member being inflatable with pressurized fluid, wherein the expandable body member comprises a wall surrounding an internal chamber, the wall being substantially impervious to the pressurized fluid; wherein the expandable main body member further comprises a safety valve configured to open when a pressure inside the expandable main body exceeds a predetermined maximum pressure; and a reserve chamber in fluid communication with the safety valve to receive at least a portion of the pressurized fluid in the internal chamber of the expandable main body member when the safety valve opens.

An anchoring frame for anchoring a device to an internal structure in a patient's body is provided, including: an elongated main body having proximal and distal ends; at least one channel running substantially over a length of the main body; a contact surface adapted to contact the internal structure in the patient's body; anchors positioned in the anchoring frame for being driven through the contact surface and into the internal structure; and a deployment driver slidable through at least one of the at least one channels, wherein sliding the deployment driver through the at least one channel drives the anchors through the contact surface.

A combination of an implantable device engaged with an anchoring frame is provided, wherein the implantable device include an expandable member having at least one key extending therefrom or groove formed therein; the anchoring frame includes an elongated main body having proximal and distal ends, and at least one channel or rail running substantially over a length of the main body; and wherein the rail is receivable in the groove and the at least one key is receivable in the channel to mechanically connect the device with the anchoring frame.

An anchoring frame for anchoring a device to an internal structure in a patient's body is provided, including: an elongated main body having proximal and distal ends; at least one channel running substantially over a length of the main body; a contact surface adapted to contact the internal structure in the patient's body; anchors positioned in the anchoring frame for being driven through the contact surface and into the internal structure; and a deployment driver slidable through at least one of the at least one channels, wherein sliding the deployment driver in a first direction through the at least one channel contacts the driver with first portions of the anchors and drives the anchors through the contact surface, and wherein subsequently sliding the deployment driver in a second direction through the at least one channel contact the driver with second portion s of the anchors and retracts the anchors from extending through the contact surface.

An anchoring frame deployment tool configured to deliver an anchoring frame percutaneously to a surgical target area in a patient is provided, the tool including: a handle for manual operation by a user; an elongated shaft extending distally from the handle; and an engagement feature provided on a distal end portion of the shaft, configured to engage a channel or a rail of the anchoring frame.

An anchoring frame deployment tool is provided, including: an elongated shaft having a proximal portion and a distal portions rotatably linked to the proximal portion; an actuator mechanically linked to the distal portion and operable by a user to rotate the distal portion in first and second opposite directions relative to the proximal portion; and a recess or cavity formed in the distal portion shaped and dimensioned to receive the anchoring frame therein.

An anchoring frame unlocking tool is provided, including: a handle for manipulation by a user; an elongated shaft extending distally from the handle; and a lock depressor extending radially from a distal end portion of the elongated shaft, the lock depressor configured to be mounted on and to slide over a rail of an anchoring frame, and to depress automatic locking structures as the lock depressor passes over the automatic locking structures.

An implantable device for treatment of obesity is provided, including: an expandable main body member configured to be positioned adjacent a portion of a stomach of a patient, within the abdominal cavity of the patient; the expandable member being inflatable with pressurized fluid; two sets of looped tabs extending substantially along two lines in a longitudinal direction of the expandable main body member, wherein, in an un-expanded configuration in which the main body member lies substantially flat, the two lines are offset, and wherein the main body member is configured to be rolled up, in the unexpanded configuration, into a compact configuration wherein the two lines align and set two sets of looped tabs align so that a shaft, rod or wire can be inserted through the looped tabs to maintain the expandable main body member in the compact configuration.

An introducer configured to deliver an implantable device into an abdominal cavity of a patient via a percutaneous, laparoscopic or mini-laparoscopic procedure is provided, including: a proximal shaft portion; a splittable introducer housing forming a distal portion of the introducer, the splittable introducer including a plurality of jaws pivotally mounted to the proximal shaft portion and pivotable between an open configuration and a closed configuration, wherein in the closed configuration, the jaws define an internal space configured and dimensioned for receiving the implantable device therein; and an actuator extending proximally of the jaws and operable by a user to open and close the jaws.

An introducer configured to deliver an implantable device into an abdominal cavity of a patient via a percutaneous, laparoscopic or mini-laparoscopic procedure, the introducer comprising: an inner sheath, the inner sheath comprising a distal end portion configured to receive the device wrapped there around in a compact configuration; and an outer sheath dimensioned to slide over the inner sheath and the device in the compact configuration, to maintain the device in the compact configuration while delivering the device; wherein the outer sheath is retractable from the distal end portion of the inner sheath and the device, to expose the device to be extracted for implantation at a surgical target site, and wherein the distal end portion of the inner sheath is bendable at an angled to a longitudinal axis of the introducer, when the outer sheath is retracted, to reorient the device to facilitate extraction thereof.

An access member attachment system is provided, including: a tool having a handle at a proximal end portion thereof; a working end at a distal end portion thereof, the working end including a socket shaped and dimensioned to receive an access member therein and to maintain an orientation of the access member relative to the working end during attachment of the access member to a patient; and an anvil configured to slide over a conduit to which the access member is to be attached.

A method of attaching an access member to a conduit in fluid connection with an expandable member implanted in an abdominal cavity of a patient is provided, wherein the method includes: sliding an anvil over the conduit at a location external of the abdominal cavity; inserting the anvil through an opening in the abdominal wall while continuing to slide the anvil over the conduit; orienting an anvil surface of the anvil against an inner surface of the abdominal wall; while holding the anvil surface pressed against the inner surface of the abdominal wall, driving the access member against an outer surface of the abdominal wall, thereby driving attachment members of the access member through the abdominal wall and against the anvil surface, whereby the attachment members are deformed against the anvil surface, thereby anchoring the access member to the abdominal wall.

An access member having undeployed and deployed configurations is provided, including: at least one port adapted to be placed in fluid communication with a conduit, the access member having a first outside diameter at a distal portion thereof, in the undeployed configuration, that is less than a second outside diameter of the access member at a distal portion thereof when in the deployed configuration.

A quick connect access member for attachment to a patient in fluid communication with a conduit in fluid communication with an expandable member implanted in an abdominal cavity of a patient is provided, wherein the access member includes: a base having a contact surface adapted to abut an inner surface of an abdominal wall of the patient; a tubular spacer having a length adapted to span a thickness of the abdominal wall, a proximal end portion of the spacer being provided with a lip; and an external portion connectable to the tubular spacer with a snap fit and configured to press against an external surface of the abdominal wall.

A quick connect access member for attachment to a patient in fluid communication with a conduit in fluid communication with an expandable member implanted in an abdominal cavity of a patient is provided, wherein the access member includes: a base having a contact surface adapted to abut an inner surface of an abdominal wall of the patient, the base including a socket portion having one or more sets of spring-loaded bearings or detents and a tubular spacer having a length adapted to span a thickness of the abdominal wall; and an external portion connectable to the base portion, the external portion have a distally extending tubular portion have at least one annular recess circumscribing an external surface thereof, configured to mate with the one or more sets of spring loaded bearings or detents.

A method of treating a patient is provided, including: passing a device including an expandable member through the skin of the patient, through the abdominal wall of the patient and into the abdominal cavity of the patient; expanding the expandable member in a space in the abdominal cavity to perform at least one of: prevention of expansion of the stomach of the patient into the space; and compression of a portion of the stomach; and anchoring the expanded expandable member against the abdominal wall of the patient.

A method of treating a patient is provided, including: passing a device including an expandable member through a minimally invasive opening through the skin of the patient and the abdominal wall of the patient, and into the abdominal cavity of the patient; accessing a tether looped through a positioning member on the expandable member from a second minimally invasive opening; and drawing the tether through the second minimally invasive opening and drawing on the position member to reorient the expandable member.

An implantable device for treatment of obesity is provided, including: an expandable main body member configured to be positioned adjacent a portion of a stomach of a patient, within the abdominal cavity of the patient; the expandable member being inflatable with pressurized fluid; and an attachment tab extending from the expandable main body member.

In at least one embodiment, the attachment tab comprises at least one structural member therein, the at least one structural member being deformable to facilitate passage through a small opening in a patient, and wherein the at least one structural member returns to an undeformed configuration upon entering the abdominal cavity to orient the attachment tab toward a structure in the abdominal cavity to attach the attachment tab to.

A method of f treating a patient is provided, with the method including: passing a flexible endoscope through an opening in the skin of the patient, and into the abdominal cavity of the patient; passing a device including an expandable member in a collapsed configuration over the flexible endoscope and into the abdominal cavity of the patient; anchoring at least a portion of the expandable member, relative to at least one structure in the abdominal cavity; and removing the flexible endoscope from the patient.

A method of treating a patient is provided, including: passing a flexible wire through an opening in the skin of the patient, and into the abdominal cavity of the patient; viewing through a distal end portion of the flexible wire; passing a device including an expandable member in a collapsed configuration over the flexible wire and into the abdominal cavity of the patient; and anchoring at least a portion of the expandable member, relative to at least one structure in the abdominal cavity.

These and other advantages and features of the invention will become apparent to those persons skilled in the art upon reading the details of the methods, devices, tools, instruments and systems as more fully described below.

BRIEF DESCRIPTION OF THE DRAWINGS

FIGS. 3A and 3B show views of a main body of a device with a shape and size approximating the shape and size of a full (post-prandial) stomach.

FIG. 4 illustrates (by arrows) potential locations on the stomach wall that can be displaced or compressed by one or more expandable devices as described herein.

FIGS. 10A-10F illustrate an expandable member that is formed from a linear string of multiple expandable cells (or, alternatively fixed size hollow balls), that can be inserted into the patient one at a time, thereby minimizing the inside diameter requirement of an introducer used to deliver the expandable cells.

FIG. 22B illustrates an expandable member being deployed via an introducer having a splittable introducer housing at a distal end portion thereof.

FIG. 22C illustrates the compacted device (including expandable member) having been received in the introducer, with the splittable jaws having been closed around the compacted expandable member to maintain it in a compact configuration.

FIG. 22F illustrates an introducer having an outer sheath that slides freely over an inner sheath.

FIG. 22G illustrates an expandable member that has been folded over and then rolled up around a distal end portion of the inner sheath of the introducer of FIG. 22F.

FIG. 22H illustrates extraction of the expandable member from the inner sheath of FIG. 22G.

FIGS. 22I-22J illustrate tongue-rolling of an expandable member.

FIG. 22K illustrates a tongue-rolled expandable member having bee inserted into an introducer that comprises a rigid, closed-ended (at the proximal end) sheath or tube.

FIG. 22O shows a further alternative arrangement, in which the sheath and device after rolling and compressing according to the techniques described above with regard to FIGS. 22L-22M, is back-loaded on an endoscope.

FIGS. 22P-22Q illustrate an embodiment of an endoscope provided with an expandable distal tip/lens.

FIG. 22R shows a variant of the tip/lens of FIGS. 22P-22Q.

FIG. 22S illustrates an alternative to use of a flexible, steerable endoscope, wherein a wire, that is viewable therethrough, is used.

FIG. 25A shows use of hook and loop type fasteners or other interlocking mechanism used for a quick connect mechanism to attach an access member to the abdominal muscle.

FIG. 25B illustrates a quick-connect access member having a ring provided with one or more magnets having polarity on the surface facing access member that is opposite the polarity of the surfaces of magnets facing the ring.

FIGS. 25C and 25D illustrate undeployed and deployed configurations, respectively, of an access member having deployable anchors.

FIGS. 25E and 25F illustrate undeployed and deployed configurations, respectively, of an access member having a spring member that functions to anchor the access member to a patient.

FIG. 27A illustrates an example of a device with multiple attachment tabs.

FIG. 27B illustrates an example of a device having three attachment tabs 150 extending from the inferior portion of expandable member, where the tabs are interjoined by margin portions at the sides of the main bodies of the tabs.

FIG. 27C schematically illustrates various features that may be provided for attachment of a device within the abdominal cavity, any of which may be used individually, or in any combination with any of the other features disclosed.

FIG. 28 illustrates one configuration of attachment tab, wherein the main body portion includes a tissue ingrowth-enhancing material.

FIG. 29A illustrates a device having attachment tabs provided with multiple structural members.

FIG. 29B illustrates a device with inflatable attachment tabs.

FIGS. 29C-29E illustrate another variation of a self-expanding attachment tab.

FIG. 30A illustrates the orientation of an expandable member of a device when implanted in a patient according to one embodiment of the present invention.

FIG. 30B illustrates a more flattened surface conformation of a portion of an expandable member, relative to the curvature of the remainder of the expandable member.

FIGS. 31A-31D illustrate an expandable member having an inflatable portion that provides a surface for conforming to the abdominal structure to be anchored to, wherein this portion is expandable independently of the expandable member.

DETAILED DESCRIPTION OF THE INVENTION

Figure 1:
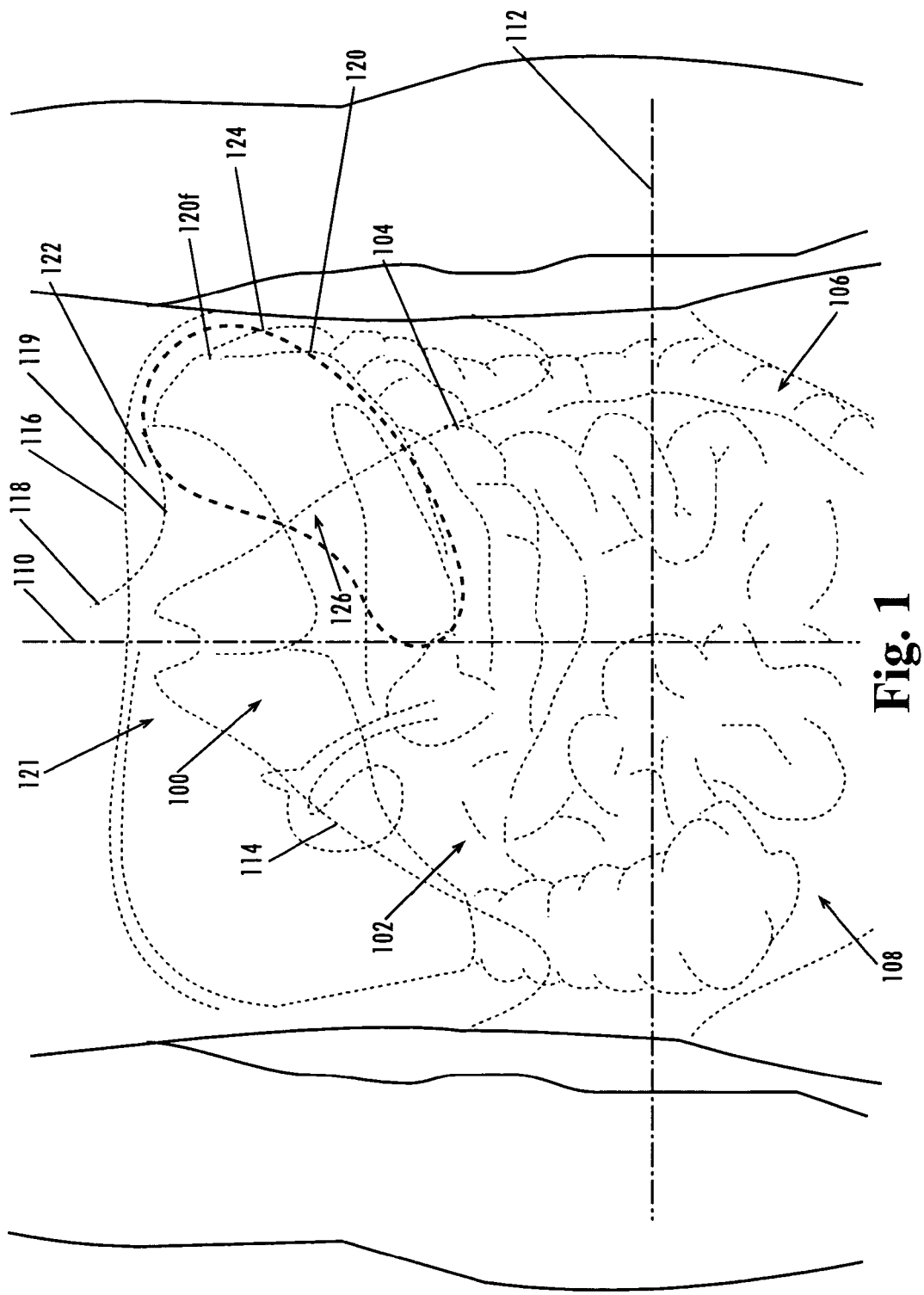
FIG. 1 illustrates the anatomy of the abdominal cavity and its contents, and surrounding features.

Before the present devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a tube" includes a plurality of such tubes and reference to "the incision" includes reference to one or more incisions and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

A "compliant" material refers to a material that is stretchable or expandable. This expansibility allows the material to increase in dimension substantially more than a noncompliant or semi-compliant material, prior to failure. For example, when formed as a balloon structure, a compliant material comprises an expansibility property of being able to increase its radius, beyond its formed radius, under pressure applied into the balloon, by 100 percent or more, without rupturing.

A "noncompliant" material refers to a material that, when formed as a balloon structure, can increase its radius beyond its formed radius, under pressure applied into the balloon, only up to about 10 percent or less prior to rupturing.

A "semi-compliant" material refers to a material that, when formed as a balloon structure, can increase its radius beyond its formed radius, under pressure applied into the balloon, by an amount between about 10 percent and about 100 percent, prior to rupturing.

The "wall" of the stomach refers to all of the layers that make up the stomach wall, including the mucosa, submucosa, muscular layers and serosa. A "layer", "layer of the stomach wall" or "stomach wall layer" refers to a mucosal layer, submucosal layer, muscular layer or serosal layer.

A "proximal" end of an instrument is the end that is nearer the surgeon when the surgeon is using the instrument for its intended surgical application.

A "distal" end of an instrument is the end that is further from the surgeon when the surgeon is using the instrument for its intended surgical application.

An "internal body structure" when referred to as a structure to which a device is to be anchored, refers to a structure internal to the skin of a patient, and which can be within the abdominal cavity of the patient, or just outside of it, such as including the outer surface of a wall that partially defines the abdominal cavity. Structures to which a device can be anchored include, but are not limited to: one or more ribs, the intercostal muscles, the abdominal surface of the diaphragm, the stomach (but where the anchor does not pass through the wall of the stomach), the anterior abdominal wall, the posterior abdominal wall and the lateral abdominal wall, the esophagus, the angle of his in the stomach, the gastro-intestinal junction, the gastro-esophageal junction, the columnar ligaments of the diaphragm near the gastro-esophageal junction, the superior aspect of the omentum, peritoneum, liver, connective tissues, ligaments, and blood vessels.

A "body floss wire" is a wire that enters and exits the body in two locations and passes inside the body between the two locations. This arrangement allows excellent control of the tension on the wire, as forces can be applied at both end portions of the wire that enter and exit the body. Additionally, this arrangement provides good control of devices being passed along the wire.

The preferred embodiments of the present invention prevent the possible issue of erosion caused by an expandable member, by not requiring anchoring to the stomach, and further, by not requiring a compression force to be applied when the stomach is not full of food. By allowing the stomach to move freely in the constrained spaced provided by the expandable member, the stomach's possible expansion size will be decreased, but there will be less opportunity for the formation of pressure necrosis since no one region will be subjected to concentrated forces. With the device in place, there is substantially no distensibility of the stomach as normal exists with an unconstrained stomach. With distensibility restricted and gastric volume reduced, as the patient ingests food, the intra-gastric pressure will rise to a level sufficient to produce satiety without distension or volume expansion of one or more regions of the stomach. The device occupies so much volume in the abdominal cavity that the stomach does not substantially depart from the shape set by the device even when filled with food. Another physiological benefit of the device is that the stomach's ability to relax in response to ingestion of food is reduced or eliminated, through producing earlier satiety. One additional physiological benefit of the expandable member may further be to substantially reduce the actual volume of the stomach itself, remodeling the organ as the muscle contracts into its new shape over the period of weeks or months (just as the heart remodels when constrained from over-expansion). Remodeling the stomach allows the expandable member to be implanted temporarily. The preferred embodiments also are positioned in a location to completely or mostly fill the space normally occupied by the fundus, thus moving the stomach medially and wedging the stomach between the expandable member and the medial and anterior aspects of the liver, and the spine posteriorly. This position also ensures that the expandable member is almost entirely maintained underneath the diaphragmatic umbrella beneath the ribs on the left side, thus concealing the expandable member, and preventing it from producing an unsatisfactory cosmetic result. Further, the preferred embodiments can have elements for anchoring on one or more locations along the abdominal cavity wall to prevent migration. Further, the preferred embodiments are provided with an outer surface that is very atraumatic. Embodiments described at least one expandable member, preferably an inflatable member, made of a material or material composite that is impermeable to gas, as well as embodiments having at least two expandable members, with one expandable member being inflated with a gas and another expandable member being inflated with a liquid.

The device embodiments of the present invention can be placed with a number of minimally invasive techniques, such as those often referred to as percutaneous, laparoscopic, mini-laparoscopic, or key-hole. Particularly important in at least one embodiment, the procedure requires no general anesthesia and typically only a single, small opening in a patient is required to deliver an implantable device. In particular, in at least one embodiment the procedure can be performed outside of an operating room setting with local anesthesia or conscious sedation and generally without pressurized insufflation.

Abdominal Cavity Anatomy

Figure 1A:
FIG. 1A is an illustration of a diaphragm in an isolated view, illustrating the conformation of the diaphragm as it exists in the body.
Figure 2:
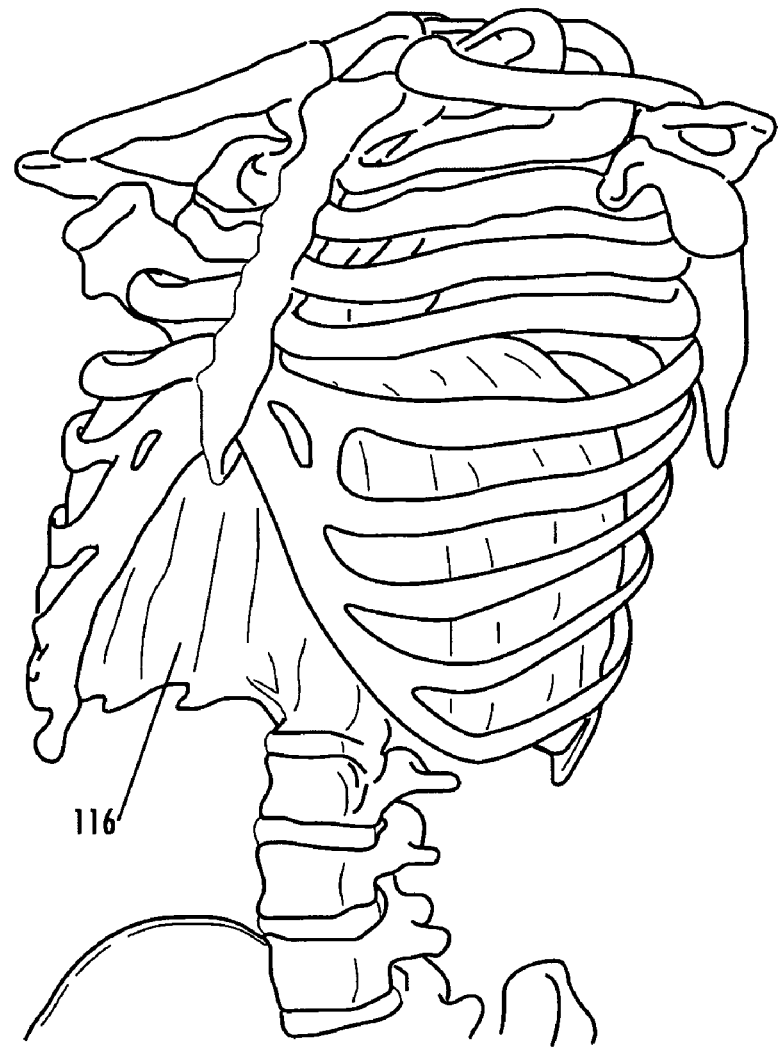
FIG. 2 illustrates the diaphragm in position relative to the rib cage.

FIG. 1 illustrates the anatomy of the abdominal cavity and its contents, and surrounding features. The abdominal cavity 100 is shown divided among four quadrants, the upper right quadrant 102, upper left quadrant 104, lower left quadrant 106 and lower right quadrant 108, as divided by the median axis 110 and transverse axis 112. The lower edge of the ribcage is illustrated by the dotted line 114 and the diaphragm is shown at 116. As seen in FIGS. 1A and 1B, the diaphragm 116 is shaped like a parachute and sits within the ribs. The esophagus 118 passes through the diaphragm 116 and joins with the stomach 120. The left lobe 122 of the liver 121 lies anteriorly of the esophagus 118 and the fundus-cardia junction 119. In one aspect of the invention, an expandable device is implanted in an extra-gastric location (i.e., outside of the stomach) generally indicated at 124, and then expanded to occupy a space that the fundus of the stomach would ordinarily expand into when the stomach is filled with food. The expanded device prevents this expansion by the fundus, thereby limiting the volume of the cavity in the stomach to a much smaller volume than if the fundus had been allowed to expand into the space. Alternatively, the device is expanded to apply pressure to the fundus of the stomach in a downward direction (e.g., in a direction toward the transverse axis 112 shown, with some transverse movement toward the median axis 110 shown), and optionally, additionally to the main body of the stomach, to reduce the volume inside the stomach to effect satiety in the patient with relatively less food ingested, relative to what the patient would require for satiety without the implant in place.

Devices

At least some embodiments of devices described herein can be implanted percutaneously, with a relatively quick and simple procedure that requires no general anesthesia and wherein only a single, small opening in a patient is required to deliver the device, which typically has a single expandable member that is self anchoring or can be easily anchored to maintain the simplicity and minimal invasiveness of the procedure.

In other embodiments, more complex configurations of expandable members are provided, where a device can contain one or more expandable members and implantation and anchoring can be performed laparoscopically. Any of the devices described herein can, of course, be implanted using open surgical procedures. Devices that can be implanted percutaneously can alternatively be implanted using laparoscopic procedures.

Devices described herein can be implanted permanently, but are also configured for reversibility, to facilitate relatively simple removal procedures, should it be desired to remove a device. Alternatively, devices according to the present invention can be implanted temporarily, such as over a period of months, and then removed or disabled when further treatment is no longer required, or to allow an alternative treatment to be applied.

Device Body Configurations

FIGS. 3A and 3B show views of a device 10 having a main body 10m,10em with a shape and size approximating the shape and size of the full (post-prandial) stomach 120b. Although main body 10m need not be expandable/collapsible to perform restriction of stomach expansion, main body 10m is typically formed from one or more expandable members 10em as will be described in further detail below, for better performance of intended functions and to allow less invasive procedures for implanting the same.

Main body 10m,10em includes curved left and right sides 10l and 10r, respectively (FIG. 3A shows the posterior surface of main body 10m,10em), wherein the left side 10l is convex and the right side 10r is concave such that the main body 10m, 10em takes on a somewhat kidney-shaped configuration. However, the superior portion 10s is substantially larger and more bulbous than the inferior portion 10i, since the fundus portion of the stomach 120 expands much more than the antrum upon receiving food. Thus, as seen in the right side view of FIG. 3B, the superior portion 10s is very bulbous and almost spherical, with a larger cross section than the inferior portion 10i, while the inferior portion is more nearly hemispherical, with the center portion of the main body tapering from the superior portion 10s to the inferior portion 10i. Configured as such, the main body 10m,10em, when implanted properly, will occupy the space that naturally exists from the stomach 120 to expand into when expanding from a pre-prandial configuration to a post-prandial configuration. By severely limiting this expansion capability, the patient is thereby able to consume only a significantly smaller volume of food than possible if the implant were not present.

Figure 3C:
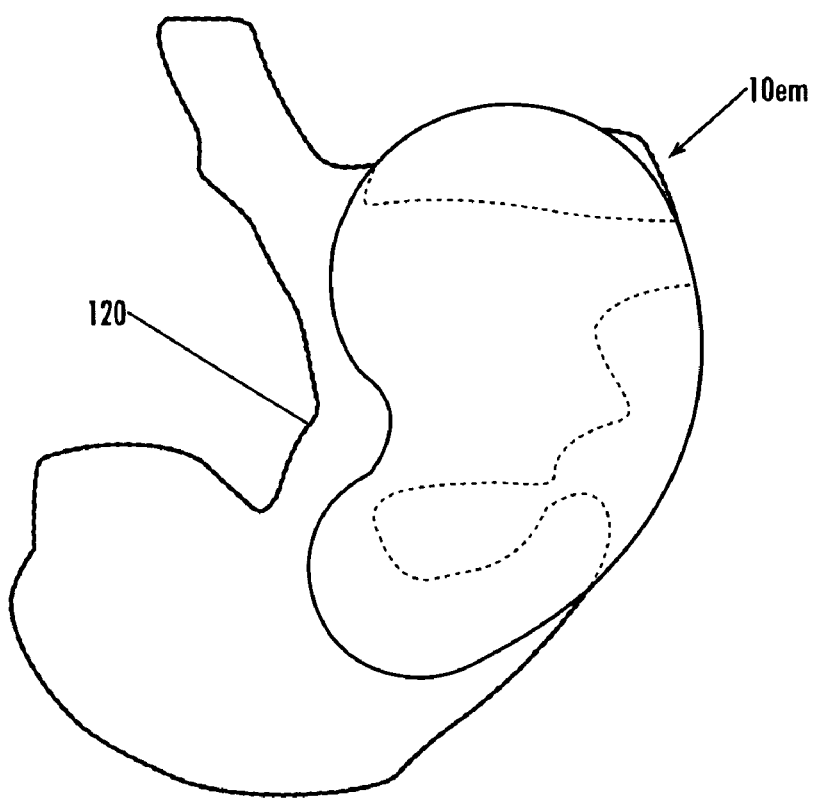
FIGS. 3C and 3D illustrate two variations of a device, wherein the inferior portion of the expandable member in FIG. 3D is longer and thus extends further inferiorly and medially than the inferior portion of the expandable member shown in FIG. 3C.
Figure 3D:
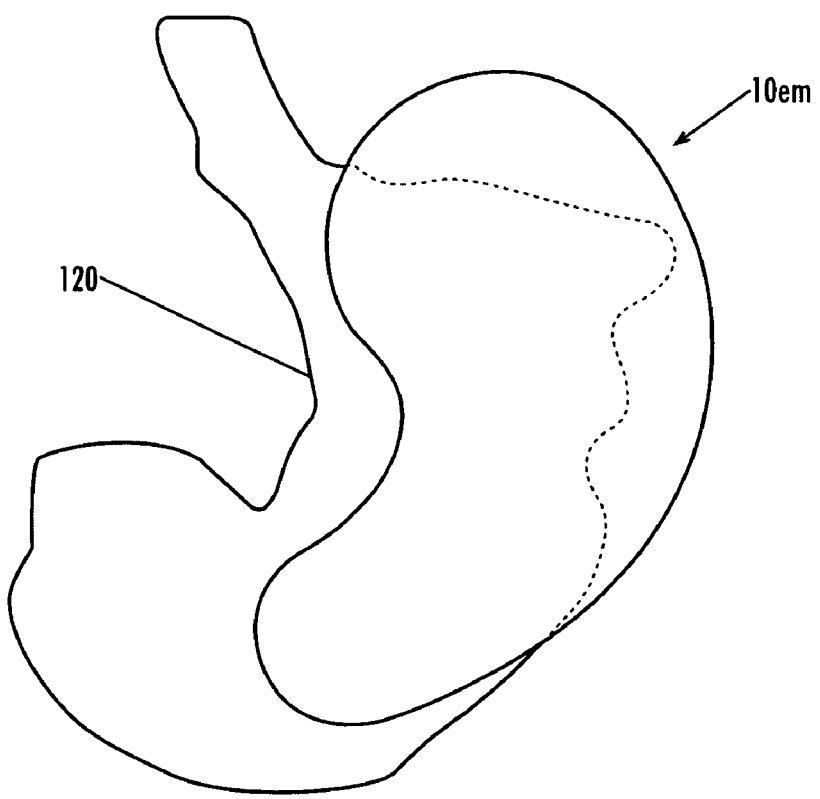

Device 10 sizes will likely vary depending on the size of the skeletal system of the patient into which device 10 is to be implanted, particularly the size of the rib cage. Further variations may be made to tweak or adjust the amount of restriction along any desired location of the stomach that interfaces with device 10. One typical variation is in the length and/or size (diameter or expandability capacitance) of the inferior portion 10i. FIGS. 3C and 3D illustrate two variations of device 10 in which the inferior portion of the expandable member 10 in FIG. 3D is longer and thus extends further inferiorly and medially than the inferior portion of the expandable member shown in FIG. 3C. In both cases, expandable member is shown in an expanded configuration, and a full, unrestricted stomach 120 is illustrated behind the expandable member 10em to illustrate the relative amount of restriction that each expandable member shown would impose on the stomach 120.

At least a portion of main body member 10m may be expandable. The entire main body 10m may be made of an expandable member 10em. When in an expanded configuration, expandable member 10em can optionally only abut or lie adjacent to the pre-prandial stomach wall, without imparting any significant deformation forces thereto. However, when the patient eats and the stomach begins to fill, expandable member 10em in this case prevents the stomach 120 from expanding into the volume occupied by expandable member 10em. In such a case, the stomach 120 becomes "deformed" as it attempts to expand and can only expand in a limited fashion, if at all, around a portion of the perimeter of expandable member 10em. Thus, upon expanding the device 10, the device 10 expands in the space(s) normally occupied by the stomach 120 as the stomach 120 expands when receiving food. Thus device 10 exerts pressure on, or at least prevents expansion of the fundus and optionally, the antrum. In embodiments where the expandable device 10 is not attached to the stomach, the stomach is free to perform its normal function of mixing food in the stomach for digesting and pushing food out of the stomach. During all of this movement the stomach may slip behind, beside or on top of the expandable device, but the internal volume of the stomach will be held to its smaller volume as the expandable device 10em is occupying the space into which the stomach would normally expand. Further details of methods for treatment of obesity, including procedures for implanting devices described herein are described below.

As noted above, an expandable device 10 can be implanted adjacent a surface of the stomach wall, either in contact therewith or at a predetermined distance therefrom, to prevent expansion of the stomach 120 into a volume occupied by the expandable device 10. Alternatively, some embodiments of the devices described herein can be configured and placed to exert an external compression on one or more locations of the stomach to deform the stomach wall, thereby decreasing the internal volume of the cavity within the stomach that accepts food and liquid intake. FIG. 4 illustrates (by arrows) potential locations on the stomach 120 wall that can be compressed (or restricted from expanding) by one or more devices 10 as described herein.

In one embodiment, expandable member 10em shown in FIGS. 3A-3B is composed of an inflatable member 10em. Inflatable members described herein can be inflated with gas or liquid or both. Examples of gases or liquids that can be used to inflate inflatable members/devices 10 include, but are not limited to: carbon dioxide, helium, isotonic dextrose solution, iostonic saline solution, air.

It may be preferable to inflate at least a portion of the expandable member 10em shown in FIGS. 3A-3B with one or more gases, to minimize the weight of the implanted device 10, as an expandable member of the configuration shown can have an internal volume approaching a liter, when filled, and a heavier, fluid-filled device of this type may be more noticeable to the patient. Alternatively, devices 10 can be inflated with a porous gel that is porous or microporous to encapsulate air or other gas bubbles, thereby reducing the weight of the gel while still permitting it to apply volumetric pressure to expand an inflatable member. Such gels may be settable, such as ultra-violet (uv) curable or otherwise chemically curable, or, alternatively, can remain in the gel state, so that they can be readily removed or added to, to increase or decrease the amount of inflation/expansion of the expandable member. Gels can be made from a flowable viscoelastic substance made of a polymer mixture, such as silicone oil, boric acid, hyaluronic acid, polyacrylic acid or combinations thereof, for example. The gel, as delivered into the expandable member 10em (e.g., such as by injection or the like) can be aerated or infused with carbon dioxide or an inert gas to create a deformable or non-deformable cellular structure that encapsulates the gas in cells, and thus has relatively low mass but still has significant resistance to compression or deformation.

When inflating an inflatable member with a pressurized gas, some materials, especially the compliant materials such as silicone, polyurethane and the like, may have an inherent porosity as it is stretched during the expansion, such that it may not adequately maintain a desired pressure within the membrane or wall of the inflatable member over an extended period of time. This seepage or slow leakage of gas from the inflatable member may require a patient to have the implant checked more frequently then required for other physiological concerns, to ensure that it is maintaining adequate pressure and thus is expanded to the extent desired to perform the desired amount of deformation of the stomach. Materials such as silicone and polyurethane have a good history of long term biocompatibility when used as implants and are two of the preferred materials for use in making devices 10.

The inflatable members of the inflatable devices described herein can include compliant, noncompliant or semi-compliant materials, or any combination of these. Examples of compliant materials suitable for use in an inflatable member as described herein include, but are not limited to: silicone, latex rubber, and polyurethane. Examples of useable semi-compliant materials include, but are not limited to: nylon, polyethylene, polyester, polyamide and polyurethane, see for example, U.S. Pat. No. 6,500,148, which is hereby incorporated herein, in its entirety, by reference thereto. Polyurethane, nylon, polyethylene and polyester can be compliant or semi-compliant materials, depending upon the specific formulation and hardness or durometer of the material as produced. Examples of noncompliant materials that can be used in the construction of inflatable members described herein include, but are not limited to: polyethylene terephthalate (PET) and urethane. Urethane can be a compliant, semi-compliant or non-compliant material depending upon its specific formulation and hardness or durometer. Compliant, semi-compliant and noncompliant categories are not solely material limited, but are better defined by their expansion characteristics, as noted above. Some materials are best suited for use in one of these categories (e.g., silicone and latex work well to make compliant structures), but other materials can be formulated and/or constructed to provide compliant, semi-compliant or noncompliant properties.

Figure 5:
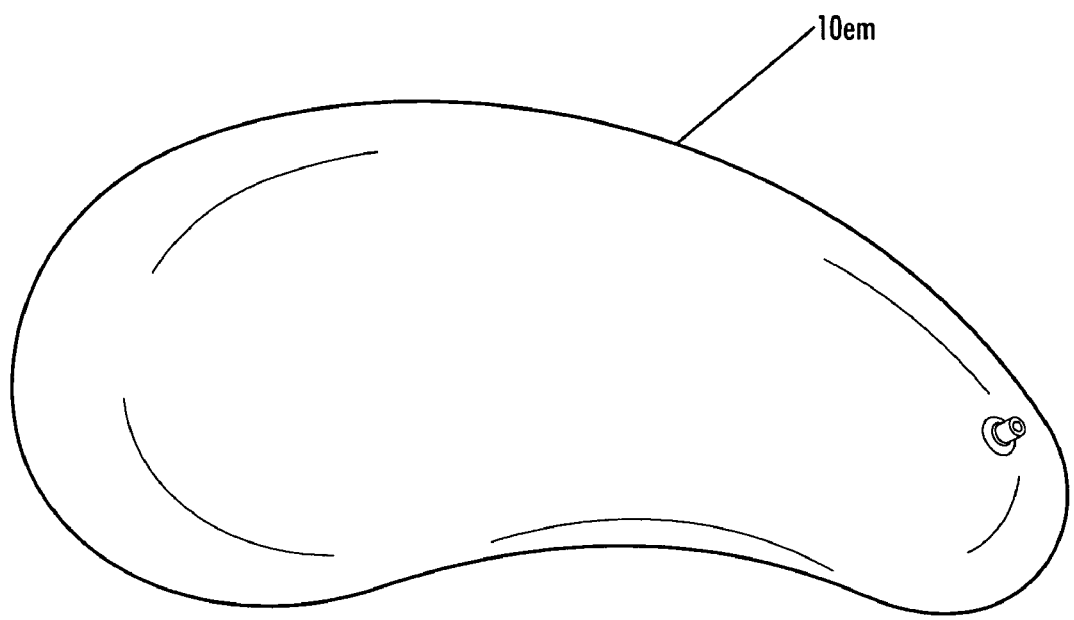
FIG. 5 is a photograph of an expandable member formed by sputtering a layer of titanium over a polyurethane expandable member formed in a shape as described with regard to FIGS. 3A-3B above.

One way of eliminating or substantially reducing seepage, such as when an expandable member comprises a compliant material that is stretched to a degree that would normally exhibit such seepage, is to provide a very thin metallic coating over the compliant material using a biocompatible metal to form the coating, as the metal layer is substantially nonporous when the integrity of such layer is maintained. FIG. 5 is a photograph of an expandable member 10em formed by sputtering a layer of titanium over a polyurethane expandable member formed in a shape as described with regard to FIGS. 3A-3B above. FIG. 5 shows the expandable member 10em in an expanded configuration. In order to avoid wrinkles in the metallized layer of the expandable member 10em, the compliant material (e.g., polyurethane in this case) was stretched over a mold configured in an expanded shape of the expandable member and welded in this three dimensional configuration, while inverting the seams, so that the smooth, seamless configuration shown resulted. Other biocompatible metals (e.g., silver, gold, tantalum, palladium, platinum or some other biocompatible metal) may be substituted for titanium, and compliant materials other than polyurethane (e.g., silicone, latex rubber, etc.) can be substituted for the substrate of such an expandable member 10em.

Another approach to reducing seepage is by co-extrusion, e.g., co-extruding EVOH (ethylene-vinyl alcohol copolymer) and polyurethane to form the expandable member 10em, with or without a metallic coating as described above.

Further descriptions of methods and materials for making a metallic coated expandable member can be found in provisional application Ser. No. 60/877,595 which was incorporated by reference above.

Figure 6:
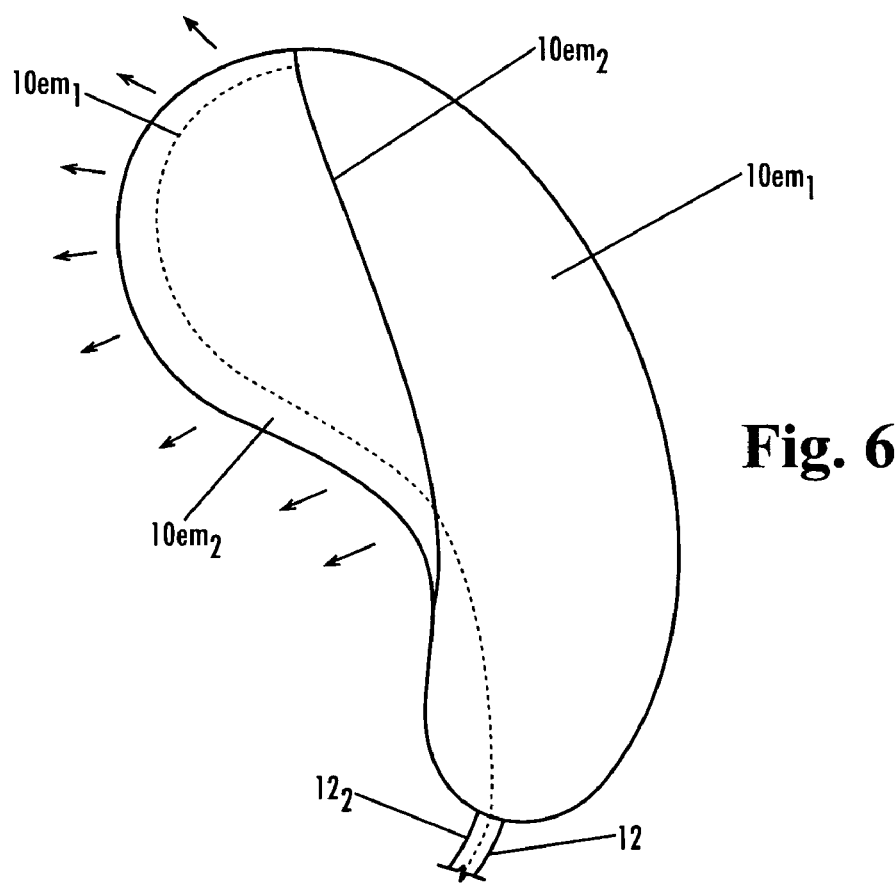
FIG. 6 illustrates an embodiment of a device that employs two expandable members.

FIG. 6 illustrates an embodiment of a device that employs two expandable members $10em_1$ and $10em_2$. The two expandable members in this case are separately and independently expandable, and may be expanded both by the same expansion medium (or by mechanical expansion methods/features described herein), or may be expanded by different expansion media or techniques or mechanical features, to provide what is termed herein as a hybrid device. In the example shown in FIG. 6, both expandable members $10em_1$ and $10em_2$ are designed to be inflated by gas, liquid, combination of gas and liquid, foams or any of the other inflation media described above. In one particular hybrid embodiment, expandable member $10em_1$ is inflated by one or more gases and expandable member $10em_2$ is inflated by a liquid such as isotonic saline or isotonic dextrose solution, for example. Since expandable member $10em_1$ contains a large volume, as noted above, this expandable member is inflated with a gas so as to be less noticeable by the recipient patient when implanted. In use of this hybrid configuration, expandable member $10em_1$ is fully inflated to occupy the space into which the stomach would normally expand when taking in food. Accordingly, expandable member $10em_1$ may be designed as a "fixed volume" expandable member, such that this expandable member will be expanded to a predetermined pressure so as to occupy a known volume. Expandable member $10em_2$, having a much smaller expanded volume than expandable member $10em_1$ (for example, the volume of $10em_1$ can be about 75 to about 80 percent of the total volume of the implant, i.e., about 75 to 80 percent of the combined volumes of $10em_1+10em_2$) uses a liquid medium for expansion thereof, as noted above. Expandable member $10em_2$ may be designed as a variable volume expandable member, so that expansion thereof can be varied to add to the fixed volume of expandable member $10em_1$ in the amount desired. In use, this liquid medium can be used to adjust the degree of expansion of expandable $10em_2$, once the expansion of expandable member $10em_1$ has already been established to further compress into the stomach 120 or to better interface with the surface of the stomach, as the liquid in a less than fully expanded expandable member $10em_2$ is able to conform well to the surface shape of the stomach.

One particular location that many surgeons are interested in restricting and/or compressing is the Angle of His, and expandable member $10em_2$ is placed to provide further compression capability at this location of the stomach 120 when device 10 is implanted as described. Also, since liquid is relatively incompressible, expandable member $10em_2$ exhibits less give, causing the stomach to be deformed at the interface between the stomach and expandable member $10em_2$, rather than compression of expandable member $10em_2$. Further, the liquid-filled chamber $10em_2$ provides a softer surface to interface with the stomach then would the surface of a pressurized, fully expanded gas-filled chamber. Still further, because liquid is relatively incompressible, a user knows how much additional volume the expandable member $10em_2$ is being expanded by (and thus also the relative degree of additional compression provided) when a specific volume of liquid is inputted through lumen $12_2$. Thus, for example, if a physician adds 60 cc of liquid through lumen $12_2$, the physician will know that the volume of expandable member $10em_2$ has expanded by 60 cc. Further, the use of liquid in the expandable member (such as expandable member $10em_2$) may provide relatively more pressure in preventing expansion of the stomach due to the density of the device, relative to one that is filled with gas. Further, the liquid may feel more "organ-like", since organs are primarily liquid, and therefore be generally better tolerated by the stomach and other organs in the abdominal cavity. Still further, expandable member $10em_1$ can be expanded to a state where the properties of this expandable chamber do not exhibit significant seepage, so that this pressure can be maintained for an extended period of time. Expandable member $10em_2$ on the other hand, can be expanded to a much greater percentage without concern about seepage, since materials used are much less porous to liquid. For example, expandable member $10em_1$ may be made of one or more plies of titanium-coated polyurethane, as described above, and expandable member $10em_2$ may be formed of silicone. For example, the silicone expandable member $10em_2$ can expand up to at least 800 percent of its normal volume.

In the example shown in FIG. 6, expandable member $10em_2$ is shown partially inflated. When fully deflated, the external surface of expandable member $10em_2$ can be compressed to contact and conform to the adjacent wall of expandable member $10em_1$ that it overlies. Further infusion of fluid into expandable member $10em_2$ causes it to expand outwardly in the directions indicated by the arrows in FIG. 6. Thus, as can be seen, expandable member $10em_2$ in this example has been placed to primarily effect compression of the fundus (or further reduction of the space provided for the fundus to normally expand into). However, the invention is not limited to this design, as expandable member $10em_2$ could be lengthened to also provide further expandability in the region of the antrum of the stomach, or could be provided to expand only against the antrum. Further, other placements of such a secondary expandable member $10em_2$ can be designed to tailor the directionality of additional compression forces (and/or space filling) to be applied.

In FIG. 6, a dual lumen conduit 12 is provided for inputting expansion media into the two expandable members $10em_1$ and $10em_2$. Thus lumen $12_1$ leads to expandable member $10em_1$ and lumen $12_2$ extends into expandable member $10em_1$ and leads into expandable member $10em_2$. Alternatively, lumen $12_2$ can extend externally over expandable member $10em_1$ and then enter into expandable member $10em_2$.

Further variations and embodiments of devices having expandable members $10em_1$ and $10em_2$ are described in provisional application Ser. No. 60/877,595 which was incorporated by reference above.

The reduction in volume of the "full" stomach that can be achieved by filling the space that the stomach normally expands into and/or compression of the stomach that is achievable by any of the devices described is in the range of about 700 cc to about 1,200 cc. The adjustable range of device 10 can be about zero cc to about 650 cc or about 50 to 600 ml, typically about 100 to 500 ml or 100 to 400 ml, wherein variations in these ranges can be achieved by varying the degree of expansion of one or more expandable members $10em$. With a hybrid device described above the expandable member $10em_1$ is expanded to occlude most, if not all of the space into which the fundus (and optionally antrum) would normally expand when taking in food, with any medial space remaining between expandable member $10em_1$ and the empty stomach being fillable by adjusting the degree of expansion of expandable member $10em_2$. Thus, for example, if the full volume capacity of a stomach 120 (with no implant impeding its expansion) is about 1,000 cc, then device 10 can be configured to initially displace about 400 to 600 cc of volume, so that the stomach's remaining capacitance is about 400 to 600 cc. Over time, device 10 can be expanded to occupy 800 to 900 cc of space, so that the stomach's capacity is reduced to about 100 to 200 cc. This adjustment can be done incrementally over time, for example. A hybrid device 10 such as the one described with regard to FIG. 6 can be implanted and the initial volume displacement referred to can be achieved by inflating expandable member $10em_1$ with gas, for example. Further subsequent reductions in the stomach's capacity can be achieved by adding fluid to expandable member $10em_2$ to expand this member as desired.

As noted above, the expandable members described herein may be expanded by an expansion medium (such as liquid, gas, gas and liquid, foam, etc.) or by mechanical expansion methods and/or features. It should be further noted here that a single expandable member can be expanded (and/or maintained at a desired degree of expansion) by a combination of one or more expansion media and one or more mechanical expansion methods and/or features. We refer to these as complex expandable members and examples of such are described below. Thus, for example, an expandable member that is inflated by gas pressure may be further supported by some other expansion means, such as a mechanical expansion member. This mechanical expansion member can alleviate some of the pressure that would otherwise be required to maintain the expandable member at a predetermined size (volume). Further, if seepage occurs, the secondary (mechanical) expansion member can maintain the expandable member at the desired volume. It is further noted here that a complex expandable member can be used in a device 10 having a single expandable member, such as like that shown in FIG. 5, or may be combined with one or more additional expandable members, e.g., like the example shown in FIG. 6, wherein the one or more additional expandable members may be expandable by expansion medium or expansion method and/or features, or may also be a complex expandable member. In at least one embodiment, device 10 is provided with a complex expandable member having the shape of expandable member $10em_1$ in FIG. 6 above, and a second expandable member $10em_2$, like that described in FIG. 6 above is provided as a fluid expandable member. Further examples and embodiments of devices employing at least one complex expandable member are provided in provisional application Ser. No. 60/877,595.

Figure 7A:
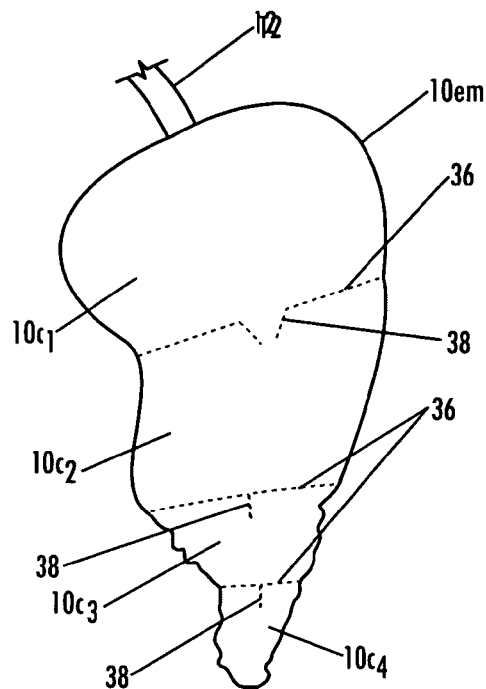
FIGS. 7A-7C illustrate a "nested chamber" configuration of an expandable member, at various stages of inflation.
Figure 7B:
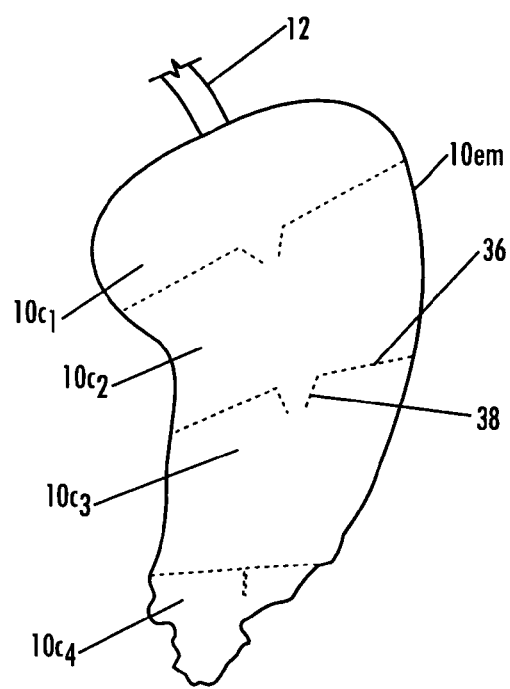
Figure 7C:
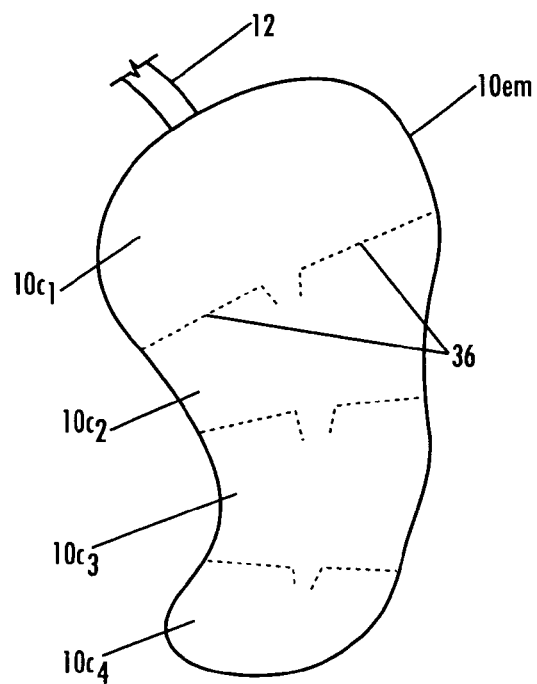

FIGS. 7A-7C illustrate a "nested chamber" configuration of an expandable member 10em, in which chambers 10c1-10c4 (although different numbers of chambers can be provided, which number may be two, three, or more than four) can be sequentially expanded, to vary the size of the expandable member and thus the amount of restriction and/or compression of the stomach to be applied by device 10. Adjacent chambers are separated by a baffle or membrane 36 that may be formed of the same material as the wall of expandable member 10em, with each baffle or membrane 36 containing at least one one-way valve 38 therein. Valves 38 are configured to open at progressively greater pressures, so that the chambers can be opened sequentially and only to the extent desired, based on the amount of pressure applied through conduit 12. Reduction in the overall volume of expandable member 10em can be achieved by passing a guide wire through conduit 12 and through all valves 38. Valves 38 open when the guidewire is extended therethrough, allowing the contents of each chamber to funnel out through conduit 12, thereby deflating the expandable member. After this, the chambers can again be sequentially inflated as described to achieve the desired volume.

More specifically, in the example shown, the valve 38 in the membrane 36 separating chambers 10c1 and 10c2 opens at a lower pressure than the valve 38 in membrane 36 separating chambers 10c2 and 10c3. Similarly, the valve 38 in membrane 26 separating chambers 10c2 and 10c3 opens at a lower pressure than the valve 38 in membrane 36 separating chambers 10c3 and 10c4. The relative locations of the chambers are not limited to those shown, but can be altered to utilize the effects of the pressure-controlled sequential expansion to first occupy primary spaces desired to be filled to block expansion of the stomach, or to apply pressure to the stomach, with subsequently expanding chambers expanding to provide supplemental space filling/pressure in adjacent areas. An operator could choose only to inflate chamber 10c1 by inflating to a pressure less than that at which the valve 38 between chambers 10c1 and 10c2 opens at. In FIG. 7A, expandable member has been inflated to a pressure greater than the pressure at which valve 38 separating chambers 10c1 and 10c2 opens at. Therefore, both chambers 10c1 and 10c2 have been inflated. This may provide sufficient restriction/compression for some patients, or for initial treatment of a patient. In some cases, even inflation of only chamber 10c1 may be sufficient for early treatment or for patient's having a relatively small rib cage, for example. After progress in losing weight has been made over time, or for patients with a larger rib cage, for example, the operator may want to increase the size and/or length of expandable member 10em (in the example shown, both are accomplished). By inputting more gas through conduit 12 to establish a higher pressure to meet or exceed the pressure at which valve 38 (positioned between chambers 10c2 and 10c3) opens, valve 38 is force open, thereby inflating chamber 10c3, as illustrated in FIG. 7B. Chamber 10c4 can be inflated by increasing the pressure still further to open the valve 38 between chambers 10c3 and 10c4, as illustrated in FIG. 7C.

Figure 8A:
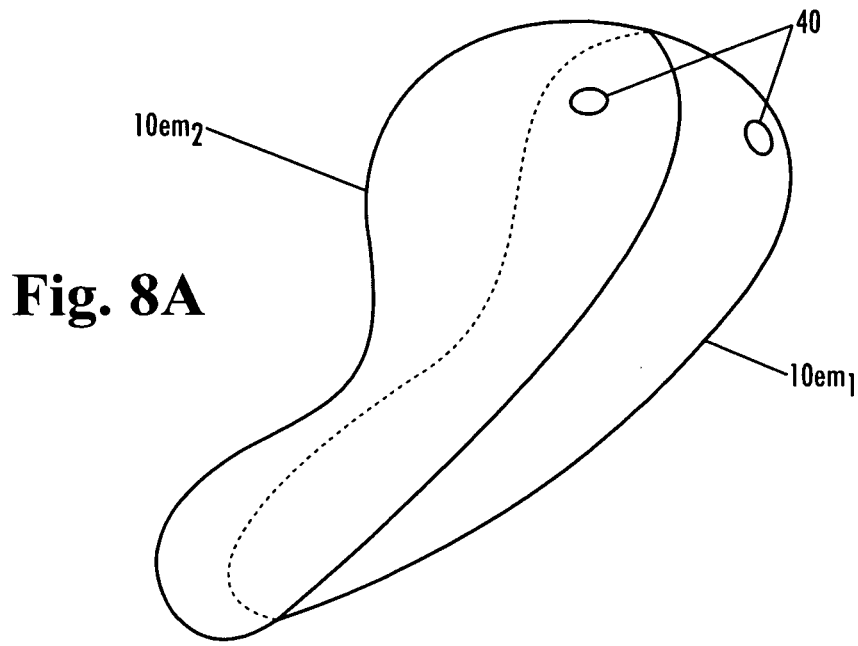
FIG. 8A illustrates safety valves installed in both expandable members.

Any inflatable expandable member 10em described herein, whether inflatable by gas, liquid or some combination thereof may be provided with a safety valve. Thus, for example, FIG. 8A illustrates each of expandable members $10em_1$ and $10em_2$ being provided with a safety valve 40. Safety valve 40 may be a flapper valve or other type of pressure release valve that opens when a predetermined pressure has been exceeded. Thus, safety valve 40 prevents overpressurization/overfilling of the expandable member that it is installed in. Safety valve 40 can be particularly valuable if the patient that the expandable member is implanted in is subjected to trauma (e.g., automobile accident, fall or other sudden impact that would spike the pressure in the expandable member and possibly cause catastrophic failure), or, in the case of an expandable member inflated with gas, in situations such as cabin depressurization in an aircraft, etc. When pressure within the expandable member has returned below the predetermined pressure (through escape of gas and or fluid from the safety valve 40) safety valve closes again, thereby retaining the remaining gas and/or fluid.

Figure 8B:
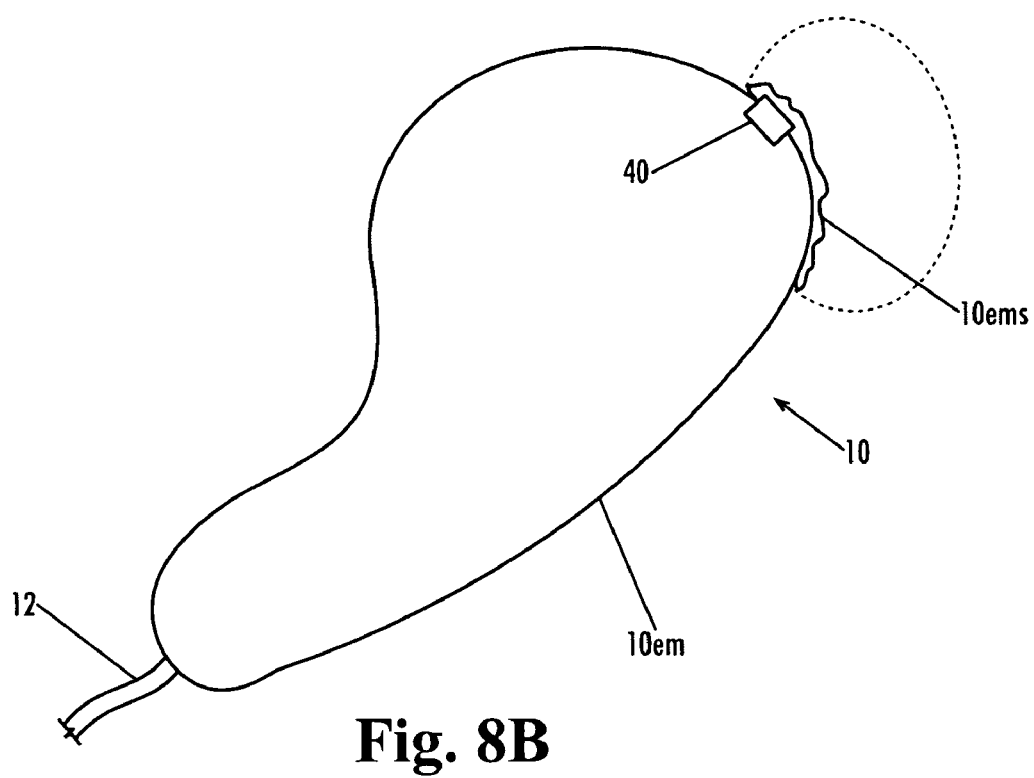
FIG. 8B illustrates an alternative embodiment, in which a safety valve is in fluid communication with a reserve expandable member.
Figure 10A:
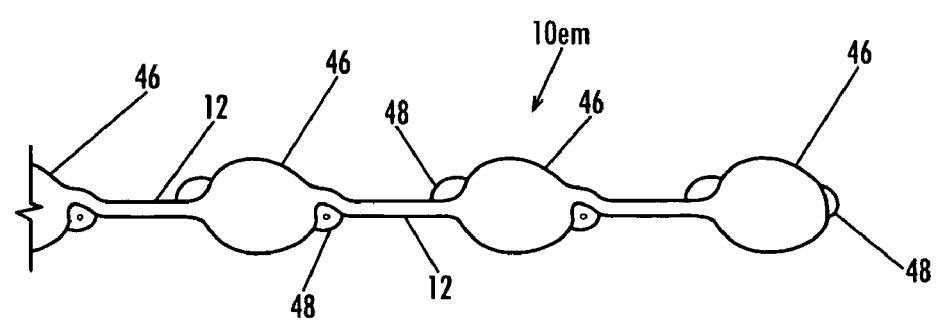

FIG. 8B illustrates an alternative embodiment, in which safety valve 40 is in fluid communication with a reserve expandable member 10emr. In this case, if the patient is exposed to any of the conditions described above (which may also include simply moving from a low altitude location, e.g., sea level, to a location high in the mountains, for example) or any condition that would cause expandable member 10em to significantly expand, thereby causing the compliant material that it is made of to become more porous resulting in leakage of gas therethrough, the rise in relative pressure that would ordinarily cause such an expansion instead opens safety valve 40 and gas passes therethrough and into reserve expandable member 10emr that is formed of a noncompliant material. Reserve expandable member 10emr is shown in an expanded configuration in phantom lines in FIG. 8B. The noncompliant material of reserve expandable member 10emr prevent gas loss, and the gas in reserve expandable member 10emr can then be recaptured into expandable member 10em when the patient has returned to the "normal" altitude from where he started, or once the traumatic event has ended.

Figure 9A:
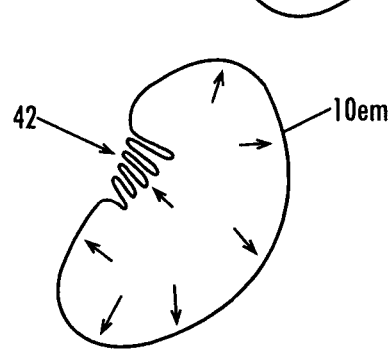
FIGS. 9A-9C illustrate an expandable member that includes excess material for additional expansion capacitance, and operation thereof.
Figure 9B:
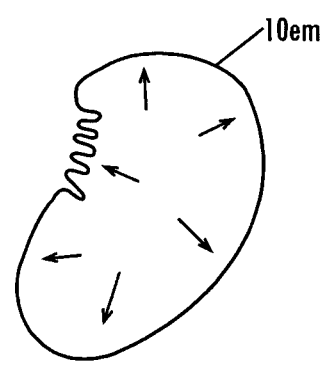
Figure 9C:
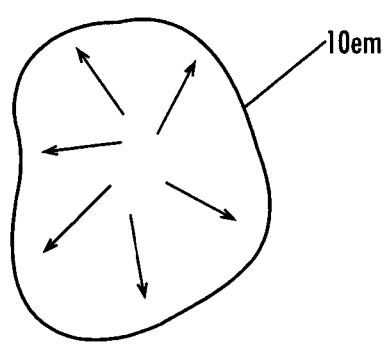

FIGS. 9A-9C illustrate an expandable member 10em that includes excess material for additional expansion capacitance, whether inflated by gas or liquid or some combination thereof. Expandable member 10em can be made from any of the materials and by any of the techniques described previously. In this embodiment, excess material 42 is provided, such as in the form of pleats, folds, corrugations, or the like, and this portion of the expandable member does not expand upon initial expansion of the expandable member. That is, at a first pressure P1, at which the expandable member 10em is inflated (see FIG. 9A), the excess material 42 remains in its compact configuration. At a somewhat higher pressure P2>P1, the excess material begins expanding, see FIG. 9B. The amount of this expansion can be varied by varying the inflation pressure, so as to control the amount of additional expansion of expandable member 10em via expansion of excess material 42. FIG. 9C shows expansion member 10em fully expanded, such as when a pressure P3>P2 or pressure higher than P3 has been inputted to expandable member to cause a complete expansion of the excess material. The folds of the excess material 42 may be thicker and/or less compliant than the material that makes up the rest of the expandable member 10em in order to provide the additional resistance to expansion. Alternatively, or additionally, the folds of the excess material may be partially and temporarily fixed together, such as by partial thermal bonding or other mechanism of adhesion, for example.

FIGS. 10A-10F illustrate an expandable member 10em that is formed from a linear string of multiple expandable cells 46, that can be inserted into the patient one at a time, thereby minimizing the inside diameter requirement of an introducer used to deliver the expandable cells 46. Cells 46 may all be inflated together, substantially simultaneously. Alternatively, valves may be provided between the cells so that they can be sequentially, individually inflated. Further alternatively, the valves may allow sequential inflation, all at the same time with a single inflation step, but prevent loss of inflation media once it has entered the cells. Accordingly, if one cell fails and deflates, the remainder of the cells 46 remain fully inflated. Accordingly, this embodiment lends itself very well to percutaneous implantation procedures. Of course this embodiment could also be implanted using laparoscopic procedures or open surgical procedures, but it provides a particular advantage for use in percutaneous delivery, as noted. Typically the cells 46 are inflated after delivery into the abdominal cavity. However, the cells 46 may alternatively be inflated while outside of the patient's body and then inserted into the abdominal cavity.

Cells 46 of expandable member 10em are connected in fluid communication with one another via conduits 12 that connect adjacent cells 46. Conduits 12 are flexible, so that the string or chain of cells 46 can be readily deformed and manipulated to assume a variety of shapes. One or more anchoring tabs 48 are provided extending from each cell 46, but not in fluid communication with the cell 48, so that these tabs 48 can be sutured through, tacked or stapled without losing pressure from the cell 46.

FIG. 10B illustrates a cartridge 50 that expandable member 10em can be delivered from during a percutaneous implantation, to deliver cells 46 into a patient's abdominal cavity. The cells 46 and interconnecting conduits 12 that form the long string of the expandable member are rolled or bunched up inside of cartridge 50 for subsequent one at a time delivery of cells 46 into the patient's anatomy. FIG. 10C shows an introducer 52 that is configured to receive cartridge 50 and advance the string of cells 46 one at a time therefrom for delivery thereof, as described below. After insertion of cartridge 50 into introducer 52, as indicated by the arrow between FIGS. 10B and 10C, and formation of a small percutaneous opening into a patient's abdominal cavity (e.g., less than about 7 cm or less than about 6 cm or less than about 5 cm or less than about 4 cm or less than about 3 cm), the distal end of introducer 50 is inserted into the abdominal cavity and located adjacent a target surgical site where it is desired to fill space to restrict the expansion capacity of the stomach and/or to apply compression to the stomach, as schematically illustrated in FIG. 10D. Note that expandable member 10em has been arranged in the introducer so that the distal most tab 48 extends distally of the distal end of introducer 52.

Upon positioning the distal end of introducer 52 at the target location, the distal most tab 48 can then be fixed to anchor the distal most cell in a desired location. Anchoring can be performed by stapling, tacking or suturing, for example, and can be to any structure adjacent the stomach 120, but typically not to the stomach 120 itself. Typically, cells 46 will be stapled via tabs 48 to at least one of the diaphragm 116 and anterior abdominal wall 127. With this initial fixation, the first (i.e., distal-most) cell 46 can be driven out of introducer 50, such as by actuation of actuator 54, for example. Alternatively, actuator 54 may be configured to install staples, tacks or sutures through tabs 48, and cells 46 may be removed from introducer, by retracting the introducer proximally to draw the fixed cell 46 out of the distal end of the introducer, see FIG. 20E. Cells 46 can be inflated individually after stapling or other fixation, or may all be inflated after finishing of the installation of all cells 46 to be used, or may be inflated prior to installing. The introducer can then be advanced distally again to the target location to anchor the next in line cell 46. This process can be repeated until as many cells 46 have been anchored as necessary to fill the desired volume of space, as illustrated at FIG. 10F. The cartridge of cells 46 does not have to be used entirely, as the surgeon can sever a link between adjacent cells 46 so as to tailor the number of cells 46 used in a particular procedure. The severed proximal end can then be caped or sewn shut (after any further inflation performed, if necessary), or connected in fluid communication with an access port 80. When cells are provided with valves, as described above, no further inflation should be necessary after severing. Introducer 52 is then removed from the port and the port is closed, leaving a custom designed, custom-shaped expandable member 10em in place, with the shape and volume being determined by the placement of the cells 46 and the number of cells 46 placed.

Implantation

As noted above, device 10 can be implanted so that, when expandable member 10em is expanded to an expanded configuration, expandable member 10em can apply compression to the stomach 120 wall, or optionally only abut or lie adjacent to the pre-prandial stomach 120 wall, without imparting any significant deformation forces thereto. However, when the patient eats and the stomach begins to fill, expandable member 10em in either case prevents the stomach 120 from expanding into the volume occupied by expandable member 10em. Thus, either the stomach is initially "deformed" by device 10, or the stomach 120 becomes "deformed" as it attempts to expand and can only expand in a limited fashion, if at all, around a portion of the perimeter of expandable member 10em. In either case, the stomach 120 is prevented from expanding to the extent that was possible prior to implantation of device 10.

Thus, upon expanding the one or more expandable members, the device 10 expands in the space(s) normally occupied by the stomach 120 as the stomach 120 expands when receiving food. Thus device 10 exerts pressure on, or at least prevents expansion of the fundus and optionally, the antrum and/or portions of the stomach intermediate the fundus and antrum.

As noted above, an expandable device 10 can be implanted adjacent a surface of the stomach wall, either in contact therewith or at a predetermined distance therefrom, to prevent expansion of the stomach 120 into a volume occupied by the expandable device 10. Device 10 can be inserted, in a contracted or compressed configuration, so as to minimize the cross-sectional area of the device as it passes, through the skin of a patient, through the abdominal wall of the patient and into the abdominal cavity. This delivery may be accomplished percutaneously or laparoscopically, for example. Once in the abdominal cavity, device 10 is positioned in a space adjacent the stomach 120, so as to fill the space and not compress the pre-prandial stomach, or alternatively to additionally provide some compression of the pre-prandial stomach, when expandable member(s) is/are expanded. As mentioned previously this positioning is to orient the device to generally follow the contours of the stomach 120 and surrounding organs, as the shape of device 10 is designed for the same.

Figure 11:
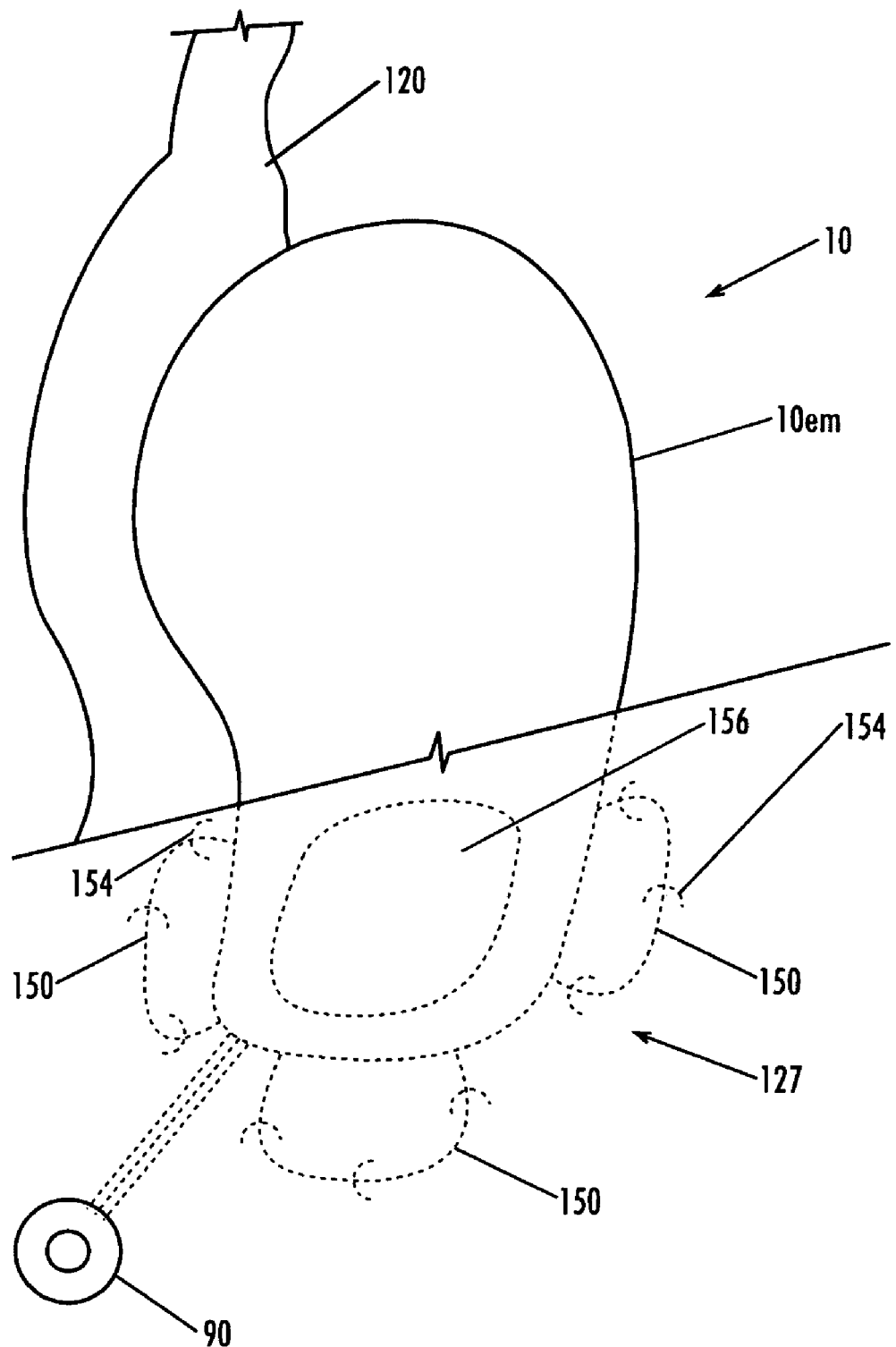
FIG. 11 illustrates a device having been inserted into the abdominal cavity in a manner as described, expandable member having been inflated and the device having been anchored.

Once properly positioned, expandable member 10em is expanded, either by inflation or mechanical means, or both, to occupy the desired space in the abdominal cavity. FIGS. 3C and 3D illustrate examples of devices 10 as properly positioned and in expanded configurations. Thus, expansion of at least one expandable member accomplishes at least one of: prevention of expansion of the stomach 120 of the patient into the space occupied by expanded device 10; and compression of a portion of the stomach 120 by expanded device 10. Device 10 may be anchored to one or more structures in the abdominal cavity. For example, FIG. 11 illustrates a device 10 having been inserted into the abdominal cavity in a manner as described, and expandable member 10em having been inflated. Any of the devices 10/expandable members 10em described herein may be provided with one or more anchoring tabs 150 attached thereto. In the example shown in FIG. 11, anchoring tabs 150 have been bonded to the surface of expandable member 10em, such as with a silicone room temperature vulcanizing (RTV) adhesive, for example. Tabs 150 may also have material thereon that encourages tissue ingrowth to provide permanent fixation of tabs 150 to the anterior abdominal wall 127 or other interior abdominal structure, to fortify the fixation provided by staples, sutures, tacks or the like. Alternatively, a single tab 150 can be placed around expandable member 10em to extend from and cover all of the areas covered by the three tabs 150 shown in FIG. 11. It would be readily apparent to those of ordinary skill in the art that other combinations of number of and shapes of tabs 150 could be substituted.

Tabs 150 are anchored to a structure (other than the stomach) in the abdominal cavity to maintain the desired positioning and orientation of device 10 relative to the stomach 120. In FIG. 11, tabs 150 have been attached to the abdominal wall 127 via sutures, staples, tacks or the like 154 to fix tabs 150 with respect to the abdominal wall 127. Port 90 is shown anchored to the opposite (external) side of the abdominal wall 127.

Further, additionally or alternatively, a portion 156 of the surface of expandable member 10em that does not come into contact with stomach 120 can be roughened or provided with some porosity (wherein the porosity does not extend all the way through the wall of the expandable member 10em) to promote adhesion and/or tissue ingrowth for anchoring device 10.

FIGS. 12A-12K illustrate steps that may be carried out during a procedure for percutaneously implanting an expandable extra-gastric device 10 according to an embodiment of the present invention. Prior to making an incision, the local area (the area of the skin in and surrounding the location where the incision is to be made) may be prepared by disinfecting with alcohol and or betadine. Additionally, the patient may be given a mild sedative or may be on conscious sedation. Though not preferred, the procedure can also be carried out under general anesthesia.

Figure 12A:
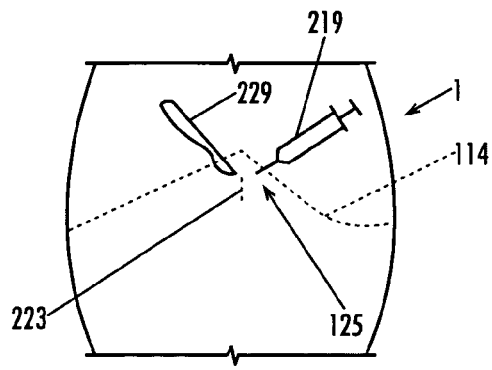
FIGS. 12A-12K illustrate steps that may be carried out during a procedure for percutaneously implanting an expandable extra-gastric device 10 according to an embodiment of the present invention.

Next a powerful local anesthetic such as marcaine (bupivicaine) or other powerful anesthetic, optionally mixed with an epinephrine or other vasoconstrictor to reduce any bleeding that might result from mild trauma can be injected into the local area through the skin 125 of the patient 1 down to the muscular layer and to infiltrate the fat layer and entire local area (the anesthetic portion of the mixture may not be needed if the procedure is performed under general anesthesia). Injection may be performed using a syringe 219, as illustrated in FIG. 12A, or other injection tool. After allowing time for the injected anesthesia to take effect, a small incision 223 is made in the skin 125 of the patient 1, with a scalpel 229 or other surgical cutting tool, in the local area over the surgical target area where device 10 is to be implanted. Optionally, in the example shown, the incision 223 is made slightly inferior to the lower rib line 114 (FIG. 12A shows a frontal schematic view of the abdominal portion of the patient 1). Alternatively, a needle (e.g., veress needle 501) can be inserted, without the need to make the incision 223, as illustrated in FIG. 12L. A conventional veress needle does not have a lumen for a guidewire. By adding a small sheath outside the shaft of the veress needle apparatus, a modified veress needle is created such that a guidewire 502 can be easily introduced through the sheath. FIG. 12L further illustrate that the location of insertion in well below the xiphoid, to the left of midline, near the palpated edge of the costal cartilages. It is noted that in the alternative method illustrated in FIG. 12A, that incision 223 can also be made in this location.

Figure 12B:
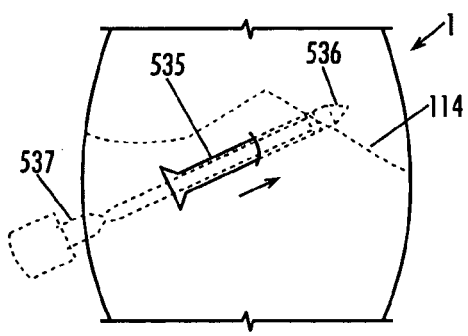

FIG. 12B shows an access sheath or cannula 535 being inserted to guide delivery and placement of device 10 and anchoring during later steps of the procedure described below. A trocar 536 (shown in phantom lines in FIG. 12B) may optionally be inserted along with insertion of sheath/cannula 535 in order to facilitate formation of a pathway into which sheath/cannula 535 is inserted, and then removed from the sheath prior to insertion of any other objects such as device 10, instruments, etc. Insertion of the sheath/cannula 535 can be performed without any additional visualization provided (i.e., just by eyesight), or may be guided by use of an endoscope 537 (shown in phantom lines) and/or with fluoroscopic visualization. If endoscope 537 is used, trocar 536 is removed after partial insertion of sheath/cannula 535 and then endoscope is inserted through sheath/cannula 535 to guide the remaining insertion to be performed, and particularly, the final placement of sheath/cannula 535.

Once sheath/cannula 535 has been properly placed to the satisfaction of the surgeon (e.g., in one example, sheath/cannula 535 is inserted into a region about three to four inches below the level of the inferior border of the liver 121 at or immediately to the right of midline) the same anesthetic or mixture of anesthetics used to numb the incision site prior to making the initial incision 223 can be injected into the abdomen through cannula/sheath 535 to numb the site interiorly of the abdominal wall.

Figure 12C:
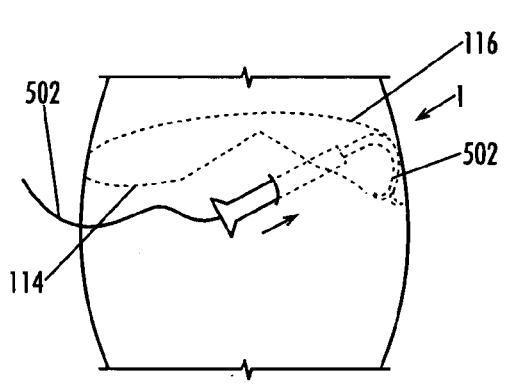
Figure 12D:
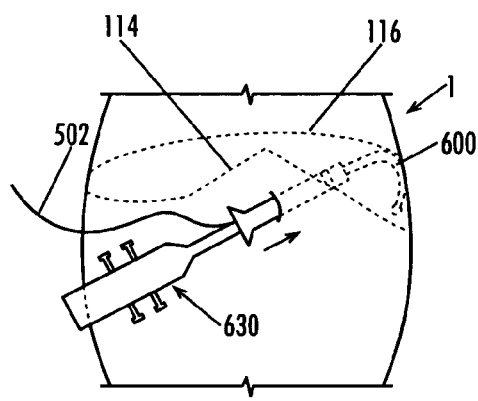

Next, as shown in FIG. 12C, a guidewire 502 is inserted through cannula/sheath 535. Guidewire 502 may be inserted under fluoroscopic visualization, 3-D RF or electromagnetic visualization (e.g., using preexisting or real-time data sets from MRI, cat scan, three-dimensional ultrasound, or other three-dimensional data set, etc.) or blindly to pass around the stomach 120 so that it rides against the diaphragm 116 and is thereby guided along the diaphragm 116 until reaching or closely approaching the spleen 128. Alternatively, a rod may be inserted instead of guidewire 502, wherein the rod is stiffer than guidewire 502 and/or have variable regions of stiffness or flexibility greater than those of guidewire 502. Additionally, the rod may have a lager cross-sectional area than guidewire 502 and optionally may have one or more lumens therethrough for delivery of suction, irrigation, injection of other fluids, injection of medicaments, etc. The rod may be inserted in similar manner to guidewire 502 by may be less likely to kink. The rod may be pre-shaped to more rigidly define a course of travel of device 10 that it guides, relative to use of the guidewire 502, which is typically flexible. Optionally, a flexible endoscope can be inserted through cannula/sheath 535 to visualize guidewire or rod 502 and confirm that it has been properly placed.

Figure 12E:
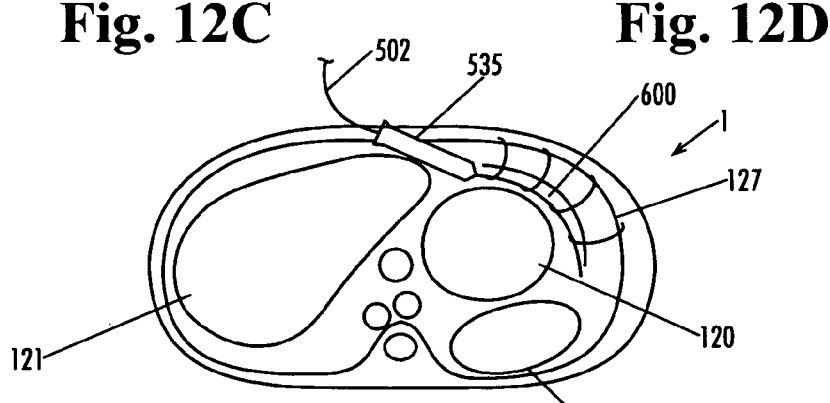
Figure 12F:
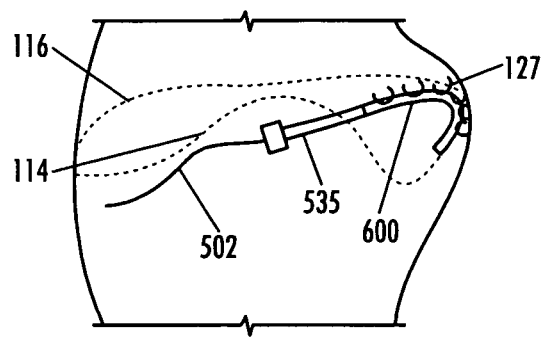

Once properly placed, an anchoring frame 600 and an anchoring frame delivery tool 630 on which anchoring frame 600 is mounted (in a manner as described in greater detail below) are advanced over guidewire 502 and into sheath/cannula 535 (see FIG. 12D) after which anchoring frame delivery tool 630 is operated to deliver anchoring frame 600 into the target position along the abdominal wall, where it is anchored there. Prior to anchoring, the surgeon will check to ensure that no bowel, omentum or other tissue is located between the anchoring frame 600/tool 630 and the abdominal wall 127. After anchoring the anchoring frame 600 to the abdominal wall 127, anchoring frame delivery tool is then removed from sheath/cannula 535 and off guidewire 502. FIG. 12E illustrates a sectional view of the patient 1 (viewed from the feet of the patient) that shows the anchoring of anchoring frame 600 to the abdominal wall 127, with the anchoring frame delivery tool 630 having been removed. FIG. 12F is a schematic illustration from a frontal view perspective, like those of FIGS. 12A-12D, showing the anchoring frame 600 anchored in place against the abdominal wall 127, as also shown in the sectional view of FIG. 12E.

Figure 12G:
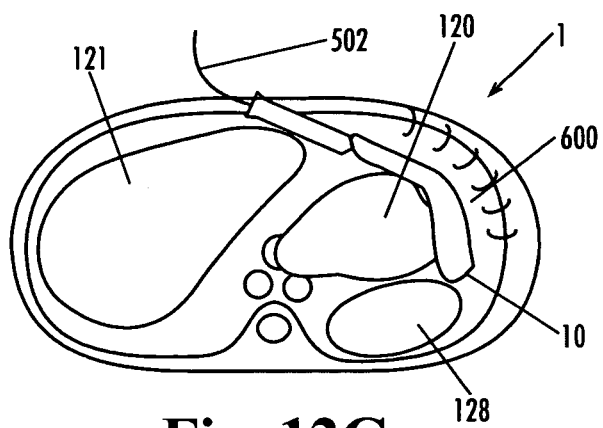

Once anchoring frame has been anchored to the target location, as illustrated in FIGS. 12E and 12F, a device deployment tool 660 having already been preloaded with a device 10 in a collapsed or compressed configuration, is next advanced over the guidewire 502 and over anchoring frame 600 in a manner described in greater detail below. Positioning of the device 10 can be monitored during this delivery using fluoroscopy, X-ray, CT or MRI visualization guidance, for example, or simply via direct visualization with an endoscope, such as a flexible endoscope inserted through sheath/cannula 535, for example. Alternatively an endoscope may be inserted into device deployment tool 660 or other tool to perform such viewing, or an endoscope can be inserted through an additional opening through the patient accessing the abdominal cavity. Device 10 is advanced to the end of anchoring frame where it automatically locks into position there. FIG. 12G shows a sectional illustration of device 10 having been locked into position on anchoring frame 600, with device delivery tool 660 having been removed.

At this stage, when the surgeon is satisfied that device 10 has been properly positioned and locked to anchoring frame 600, cannula/sheath 535 and guidewire 502 are both removed. For devices 10 that include one or more inflatable expandable members 10em, at least one conduit 12 will remain extending from device 10, proximally out through the incision 223 having been made in the patient. The one or more conduits 12 can then be used to inflate the one or more expandable members. For devices that do not include an inflatable expandable member 10em, a conduit 12 is not necessarily required, although there may be one present, depending upon the type of mechanically expandable member(s) that is/are used. For example, a conduit may be provided to insert a wire therethrough to mechanically expand the expandable member 10em. Otherwise, if a conduit 12 is not included, then the one or more expandable members are expanded in a manner as has already been described.

Getting back to devices 10 having at least one inflatable expandable member, one or more expandable members 10em may be inflated at this stage to test the amount of displacement and positioning of the device when in an expanded configuration, which may help to determine whether device 10 will perform as intended. One method of testing in this manner is with the use of an intra-gastric sizing device 310 (e.g. an intra-gastric balloon catheter) in a manner as described in application Ser. No. 11/407,701. Additionally, or alternatively, testing may be performed by visually observing the effects of expansion, such as by inputting radiopaque fluid into the stomach 120, and/or by observing the expansion of the device when it is provided with one or more radiopaque indicators, as has already been described previously. Visualization, in such instances may be performed fluoroscopically or with other X-ray visualization, for example.

Figure 12H:
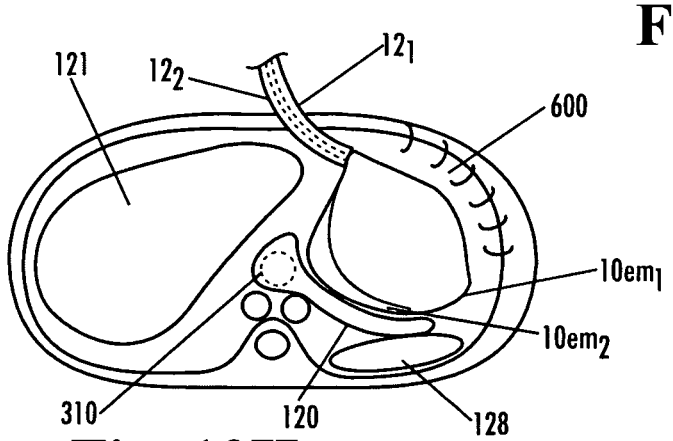
Figure 12I:
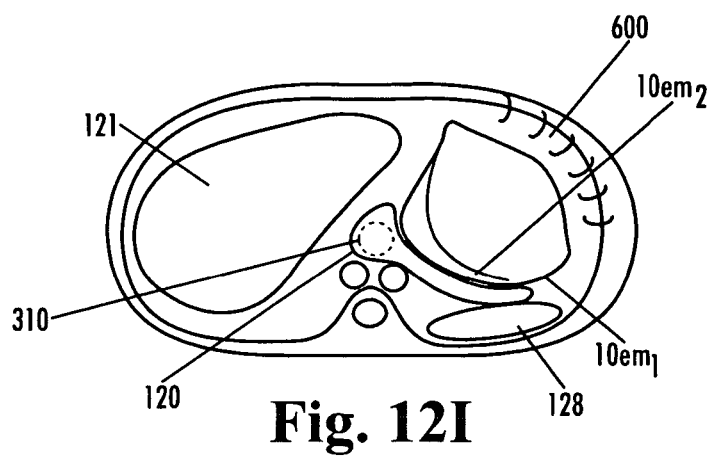

FIG. 12H illustrates expansion of a first expandable member $10em_1$ using pressurized gas, for example. At this time, an intra-gastric sizing device may optionally be already in position, and typically is placed and inflated to the desired size prior to expanding expandable member $10em_1$. For devices having only one expandable member 10em, expansion of this expandable member would then be performed to accomplish the desired amount of space restriction as indicated by feedback from intra-gastric sizing device 130, for example. In the example shown, where two expandable members are provided, expandable member $10em_1$ is typically inflated to a predetermined pressure where it has been determined that the expandable member has not expanded or stretched to a degree where the leakage rate of gas through the member is unacceptable. Typically, a maximum pressure will have been predetermined where the leakage rate is not excessive, and expandable member $10em_1$ will not be expanded by a pressure that is greater than this maximum pressure. If the resulting degree of expansion of expandable member $10em_1$ does not provide sufficient displacement, then the second expandable member is expanded, such as by inputting pressurized liquid into expandable member $10em_2$, to expand it until sufficient displacement has been achieved, such as confirmed by visualization and/or feedback from intra-gastric sizing device, for example, see FIG. 12I.

Figure 12J:
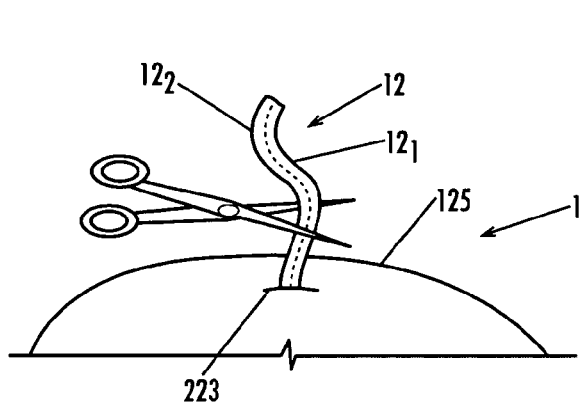
Figure 12K:
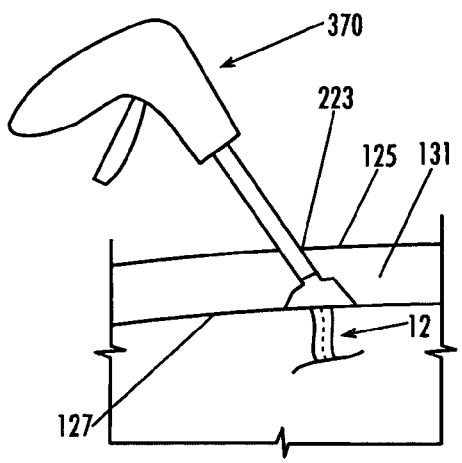
Figure 12L:
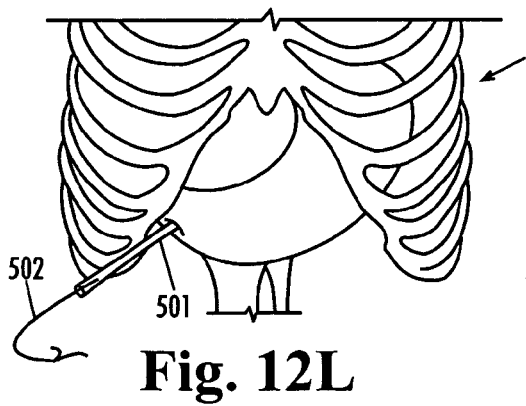
FIGS. 12L-12N illustrate variations of the method depicted in FIGS. 12A-12K.

At this time, conduits $12_1$, $12_2$ can be either clamped off to maintain the pressures within expandable members $10em_1$, $10em_2$, or the pressures can be released, thereby allowing expandable members $10em_1$, $10em_2$. It is easier procedurally to release the pressures and so this is typically done. However, the surgeon may choose to clamp off the conduits to maintain at least partial pressures in the expandable members to ensure that they maintain the observed positions. In any case, conduit (s) 12 are next trimmed to an appropriate length for connection with an adjustment member 80, as illustrated in FIG. 12J.

Conduit(s) 12 are then connected to a mating connector on adjustment member 80 or to a deployment tool 370 configured to mate conduit 12 with adjustment member 80, and, after connection of conduit 12 to adjustment member 80, adjustment member deployment tool 370 is then used to anchor adjustment member 80 to the patient. By advancing deployment tool 370 into the patient, the portion of conduit that had extended from the patient 1 is pushed back into the patient, until the adjustment member is positioned in the target location where it is intended to be anchored. This positioning can be verified using any of the previously described visualization techniques, or can be performed blindly, with feedback from palpitation, for example. In the example shown in FIG. 12K, adjustment member 80 is anchored subcutaneously, to the external surface of the abdominal wall 127. As has been disclosed previously, adjustment member 80 can alternatively be anchored subcutaneously, to an inner layer of the skin for example, or otherwise in the fat layer 131 without being anchored directly to the abdominal wall 127. Once adjustment member 80 has been anchored in the desired location, deployment tool 370 is withdrawn and the one or more expandable members are reinflated, if they had been previously deflated, or topped off, if the conduits 12 were clamped to maintain some pressure, to return the one or more expandable members to their desired sizes. In this way, the patient can begin to experience beneficial weight loss from the effects of device 10 on the stomach 120 beginning immediately after completion of the procedure, unlike current procedures, which typically require around six weeks before a return visit to "complete" the procedure to make it effective in helping weight loss. The same type or types of monitoring can be used here, as described above with regard to FIGS. 12H-12I, to provide feedback as to when the one or more expandable members have been expanded by the desired amount. Alternatively, one or more of the one or more expandable members may be left in an unexpanded configuration, with the patient being allowed to heal and then return to have the expandable members(s) inflated. Further alternatively, device 10 may be implanted in combination with a constricting band, such as the LapBand™ or similar implant to improve results from such constricting band, or to make weight loss efficacious where prior implantation of such a constricting band has not been efficacious. For example, a constricting band generally useful for restricting the amount of solid food ingested by the patient 1. However, a patient 1 may "cheat" the effectiveness of a constricting band approach by drinking high caloric liquids, for example. For example, a patient could drink a thirty-two ounce milkshake and this would pass right through the constriction established by the constricting band. However, with device 10 implanted and expanded as described, the stomach is preventing from expanding, even by high caloric liquids.

Once the surgeon is satisfied that the expandable member (s) have been expanded by the desired amount, or if the expandable members(s) are to be left in a contracted (unexpanded or partially expanded) state, the patient is closed, including, suturing the skin 125 at the site of the incision 223.

Figure 12M:
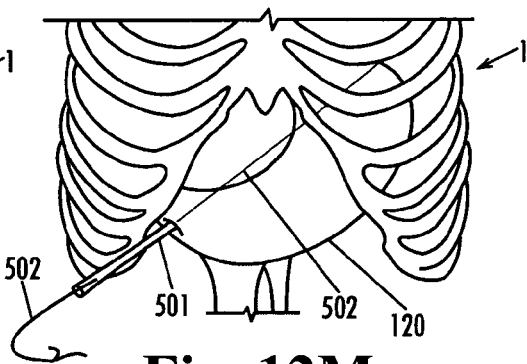
Figure 12N:
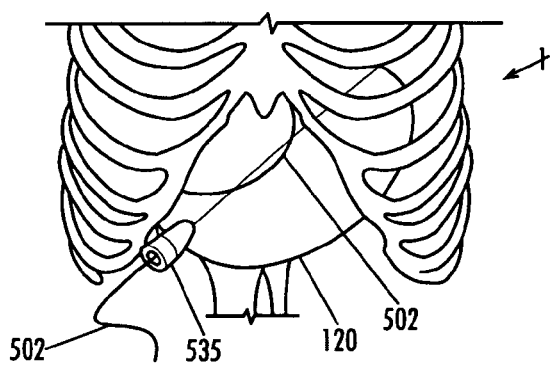

FIGS. 12L-12N illustrate variations in the percutaneous procedure described above that can be alternatively performed. As already noted above, FIG. 12L schematically illustrates percutaneous insertion of a guidewire through a needle 501, wherein the incision and sheath insertion steps of FIG. 12A-12B need not be carried out. FIG. 12M illustrates the insertion of guidewire 502 to follow the contour of the caudal surface of the diaphragm as it is pushed up and around the stomach 120, as far as the spleen, like described in FIG. 12C above. The distal end of guidewire 502 may be provided in a "J" shape or other bent shape to make it more atraumatic.

Once the guidewire 502 has been placed as desired, needle 501 is pulled off of guidewire 502 and removed. A port 535 (similar to a laparoscopic port or other access sheath or cannula 535 is then inserted through the opening made by needle 501, as illustrated in FIG. 12N. Installation of anchoring frame 600, device 10 and access member 80 may then be performed as described above with regard to FIGS. 12D-12K. In another variation regarding expanding expandable members 10em, for a device 10 having two expandable members, expandable member $10em_1$ may be expanded with gas after the access member 80 is installed/anchored, and expandable member $10em_2$ may be expanded with fluid, after completion of the procedure and some passage of time (e.g., during a follow-up visit).

Any of the variations of the procedure described above may be executed under fluoroscopic visualization, 3-dimensional navigation or other CT/MRI guidance. Further alternatively, any of these procedures may be performed as mini laparoscopic procedures (e.g., where the entire abdominal space is not insufflated, but only a small portion is and general anesthesia is not used; or where at least one of the steps involving insertion into the abdominal cavity is performed without direct visualization provided by an endoscope, for example. Anchoring of anchoring frame 600 may be performed as a separate step of the procedure, as shown and described above, or, alternatively, may be combined with the device 10 insertion and positioning part of the procedure, wherein the act of sliding the device 10 over the anchoring frame drives the anchoring of the anchoring frame 600 at the same time that device 10 is positioned (slid) thereon. All tools referenced in the above procedure may include lumens to permit insertion of other tools and/or devices therethrough, including, but not limited to: endoscopes, wires, etc. and/or to allow delivery of suction, irrigation, and/or other substances. Alternatively to mounting the adjustment member 80 to conduit 12 in any of the manners described above, adjustment member may be pre-attached or integral with conduit 12. As already noted previously, device 10 may include one or more chambers (expandable members) and may also contain fluids, gases, structural members, foams and/or other space occupying materials.

Figure 13A:
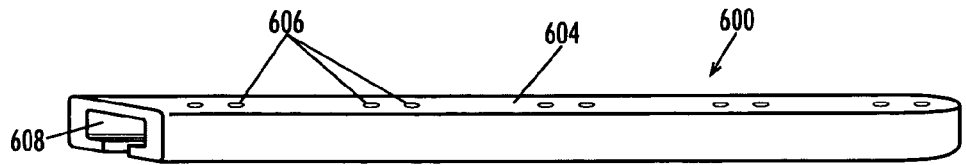
FIGS. 13A-13D illustrate an embodiment of an anchoring frame that can be used for anchoring a device in the abdominal space.

Referring to FIGS. 13A-13D, an embodiment of an anchoring frame 600 is illustrated that can be used for anchoring a device 10 in the abdominal space, such as, but not limited to the manner described above with regard to FIGS. 12A-12K, for example. FIG. 13A illustrates a perspective view of anchoring frame in an undeployed configuration, i.e., when anchors 102 have not been deployed to anchor the anchoring frame. In the undeployed configuration, anchoring frame 600 has a contact surface 604 that is configured, shaped and dimensioned to conform to a tissue surface in the abdominal cavity to which the anchoring frame 600 is to be anchored. Openings 606 are provided that extend from an inner surface of anchoring frame, through the wall on which the contact surface 604 is formed, and through the contact surface 604. Openings 606 are arranged for delivery of anchors 602 therethrough and are thus aligned with anchors 602 as will be described in greater detail below. Although shown as substantially straight, anchoring frame and contact surface 604 may have a curvature that is formed to follow the general contour of the structure in the abdominal cavity that it is to be anchored to. Thus, for example, for anchoring to the abdominal wall 127 in the procedure describe above, anchoring frame 600 and contact surface 604 are curved to conform to the contour of the abdominal wall 127 just below the diaphragm 116. Thus, the curvature (or straightness) of the anchoring frame 600 and contact surface 604 is dictated by the contour of the tissue surface that it is intended to be anchored to. Thus, anchoring frame 600 can be substantially rigid and shaped with a predefined curvature (or shape) of contact surface 604 to match that of the tissue surface that it is to be anchored to. Alternatively, and preferably, anchoring frame may be flexible, so that when compressive forces are applied to it, by applying a force distally to the proximal end of anchoring frame 600, such as with anchoring frame deployment tool 630, for example, while the distal end of anchoring frame is fixed, such as by being abutted up against a ball end of a guidewire, for example, the compressive force causes the frame 600 and contact surface 604 to bend and thereby abut against the surface of the tissue to be anchored to. Frame 600 and surface 604 may be structurally biased so as to be predisposed to bending in one direction away from the longitudinal axis of the frame 600, as opposed to bending in the opposite direction, to ensure that the contact surface bows out in the direction where it will contact the tissue structure to which it is to be anchored.

Within the channel 608 are positioned a series of anchors 610 such as staples, tacks, spikes or other sharpened mechanical member configured to be driven into the tissue and to maintain anchoring within the tissue after piercing it. The staples of other sharpened mechanical members are positioned in frame 600 in small channels and are completely retracted so as not to extend through surface 604 as frame 600 is being delivered into the abdominal cavity. A deployment member 612 is provided within anchoring frame 600 that is configured for deploying the anchors. Deployment member 612 includes an enlarged driver 613 located distally of anchors 10, and a cable or wire 614 that extends proximally from drive 613 and out the proximal end of anchoring frame 600. Cable/wire 614 has sufficient length so that when anchoring frame is placed in position on the target area in the abdominal cavity to which it is to be anchored, the proximal end portion of cable/wire 614 still extends out of the patient 1 (such as out of the incision 223 in the procedure described above, for example).

When frame 600 is positioned in the abdominal cavity at the target location where it is to be anchored, e.g., against the abdominal wall, frame 600 is held motionless against the target area while deployment member is retracted proximally. If frame 600 is a flexible frame, constant pressure is exerted in a distal direction against the frame to ensure that it remains buckled/bent against the target area, so that it conforms to and contacts the target surface (e.g., abdominal wall). By pulling on cable/wire 614 while holding frame 600 substantially motionless, deployment driver 613 is retracted proximally through channel 608, as illustrated in FIG. 13C. As it is retracted, driver 613 contacts anchors 610 driving them out through openings 606 and into the tissue, thereby anchoring frame 600 to the tissue as desired. Upon completely withdrawing deployment member 614/driver 613, and open channel 608 is then provided for guiding one or more keys provided on a device 10 that are slidable in channel and are configured to be prevented from pulling through the slot at the bottom of the channel 608.

To further enhance anchoring of frame 600, all of a portion of surface 604 may be covered with an ingrowth layer 616, such as a fabric layer (e.g., polyethylene terepthalate or other porous, biocompatible fabric) or other porous layer configured to encourage tissue ingrowth.

Figure 14A:
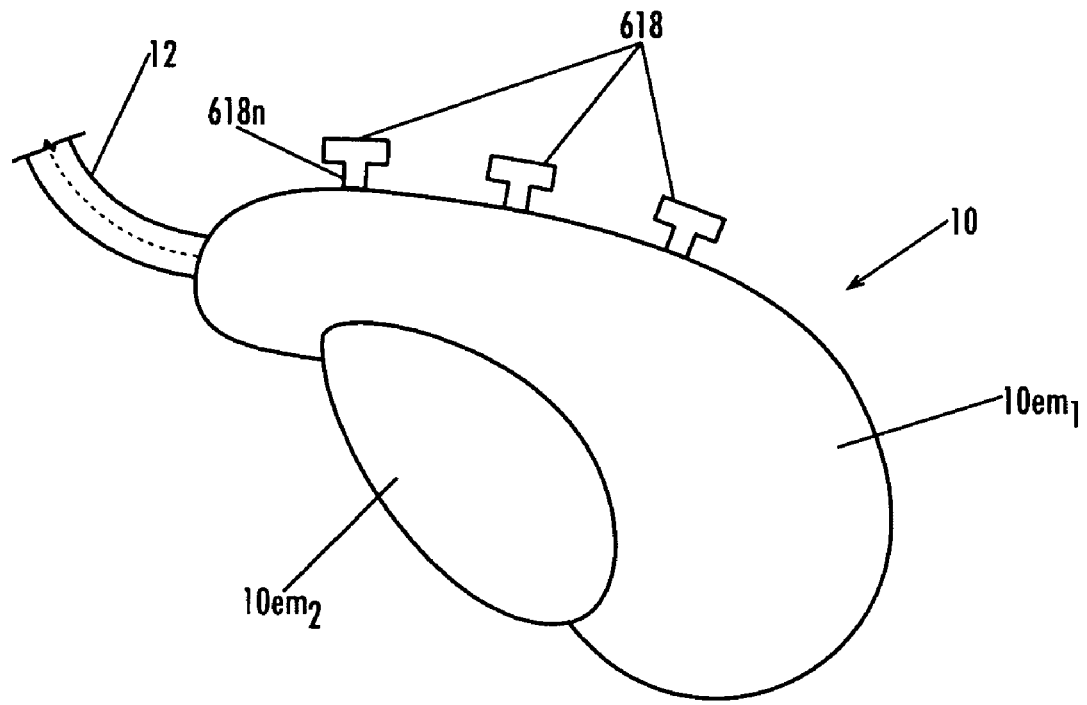
FIG. 14A illustrates an example of a device provided with keys configured to slide within a channel of an anchoring frame.
Figure 14B:
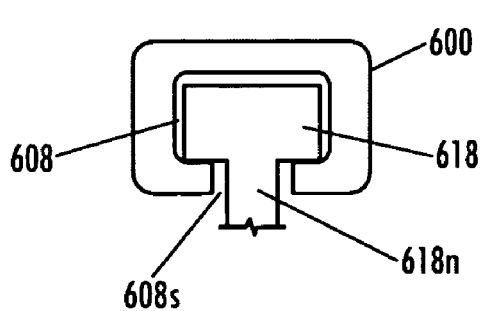
FIG. 14B shows an end view of a key inserted into a channel of an anchoring frame.
Figure 14C:
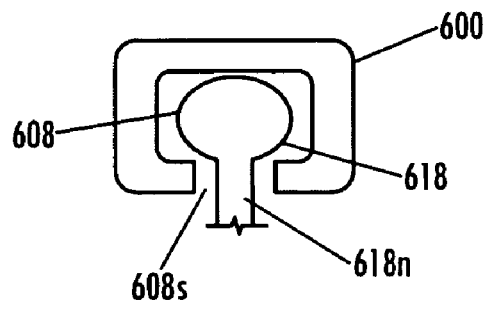
FIG. 14C shows an example of a key inserted into a channel of an anchoring frame, wherein the enlarged portion of the key is spherically shaped.

FIG. 14A illustrates an example of a device 10 provided with keys 618 configured to slide within channel 608 while being prevented from sliding out through slot 608s. Thus, keys 608 are generally matching to the cross-sectional configuration of channel 608, while each having a neck portion 618n of narrower dimension that is configured to slide within slot 608s. FIG. 14B shows an end view of key 618 inserted into channel 608 of frame 600. Alternatively, key 618 need not have a cross sectional shape that matches the cross-sectional shape of channel 608, as long as the enlarged portion of key 618 is too large to pass through slot 618s, yet small enough to slide within channel 608, and neck 618n is of small enough dimension to slight through slot 608s. FIG. 14C shows an example of a key 618 wherein the enlarged portion is spherically shaped. Keys 618 are not limited to the shapes described but can take on virtually any cross-sectional shape, as long as the requirements in size described above are met, relative to cooperating with channel 608 and slot 608s. Of course, some cross-sectional shapes are more advantageous than others with regard to functionality, such as minimizing resistance/friction between the keys 618 and channel 608 as device 10 is deployed over frame 600.

The number of keys 618 attached to device 10 is also variable and may vary from one up to several dozen. Lengths of the keys (relative to the longitudinal axis of frame 600) can also be a variety of sizes, up to and including, a continuous key that extends over the full length of channel 608. FIG. 14D illustrates the device 10 of FIG. 14A having been mounted on anchoring frame 600 of FIGS. 13A-13D. Of course, during the insertion of device 10 into the abdominal cavity target area, device 10 will typically be in a compact, collapsed configuration to minimize its size during the delivery and as it is mounted on anchoring frame 600. An exception may be in a situation where device 10 is implanted using an open procedure.

Figure 15A:
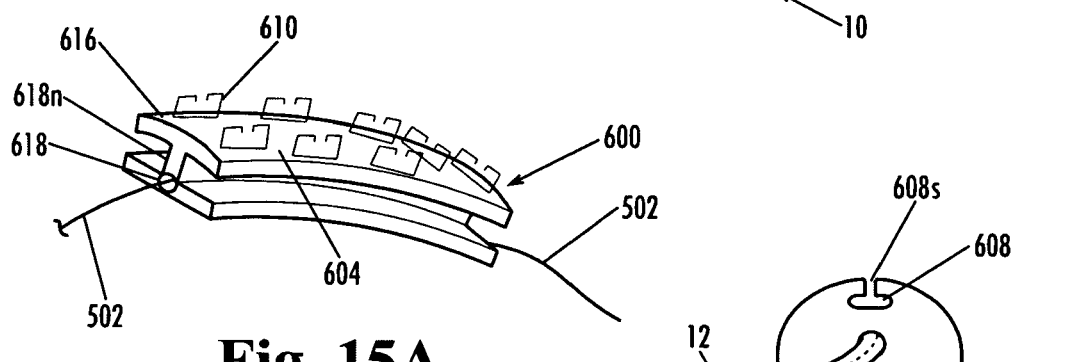
FIG. 15A illustrates another embodiment of an anchoring frame 600 that employs a rail configuration for receiving a device thereover.

FIG. 15A illustrates another embodiment of an anchoring frame 600 that employs a rail configuration for receiving a device thereover. Anchoring frame 600 is constructed similarly to any of the variations described above with regard to frame 600 in FIGS. 13A-13D, including the contact surface 604, optional ingrowth layer 616, anchors 610, and openings 606. Frame 600 is installable over a removable wire, such as guidewire 502, for example, with the wire being removable after completion of the procedure. In this arrangement, however, rather than having a channel 608 to slidably receive one or more keys 618, rail or beam 618 functions as a key with respect to a channel or groove 608 formed in device 10 that slides over rail or beam 618. As with the keys 618 on device 10, the rail or beam 618 need not be T-shaped in cross-section, as shown in FIG. 15A, as long as the enlarged portion of rail 618 is too large to pass through slot 608s in the channel 608 of device 10, yet small enough to slide within channel 608, and neck 618n is of small enough dimension to slide through slot 608s. Likewise channel 608 need not be T-shaped in cross section, but may have some other cross-section shape that forms an enlarged portion to slide within channel 608 and is impassable through slot 608s, and a neck portion 618n that is slidable within slot 608s.

Figure 13B:
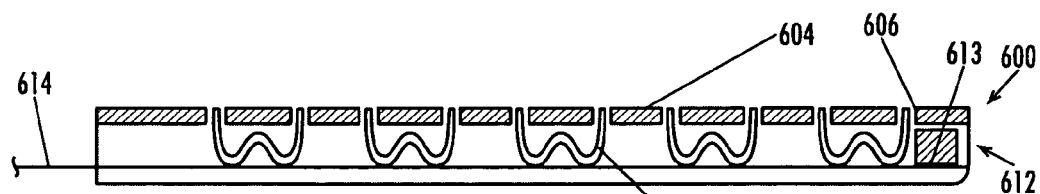
Figure 13C:
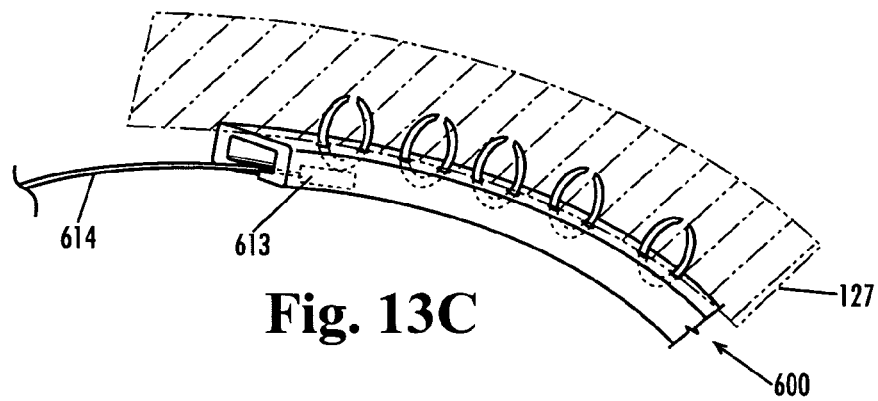
Figure 13D:
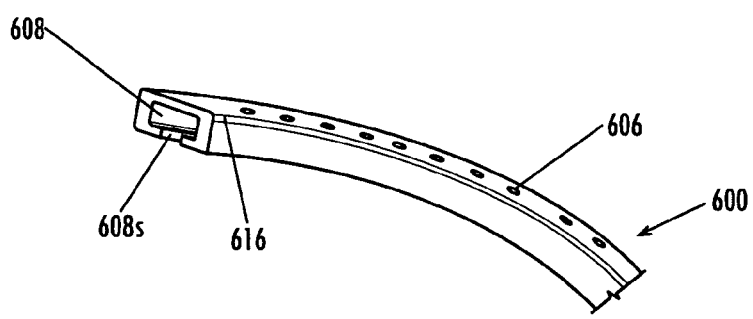
Figure 14D:
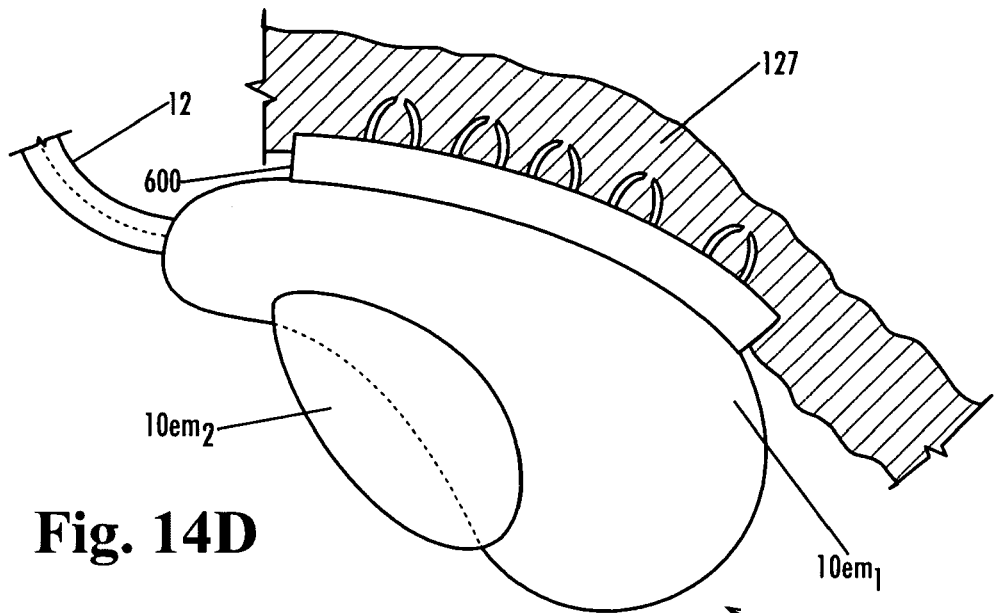
FIG. 14D illustrates the device of FIG. 14A having been mounted on an anchoring frame.
Figure 15C:
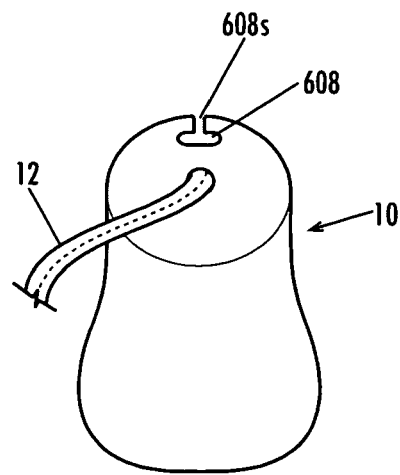
FIG. 15C shows an end view of a device having one configuration (T-shaped cross-section) of channel configured to slide over a rail of an anchoring frame.
Figure 15B:
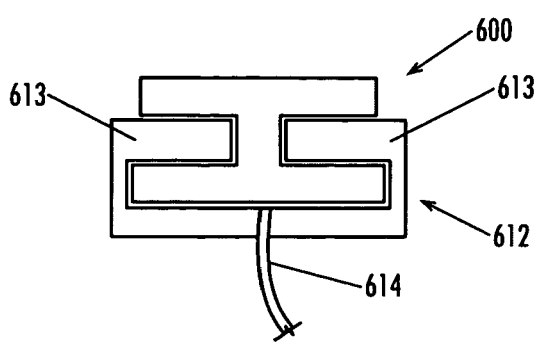
FIG. 15B is an end view of a deployment member configured to slide over a rail 618 of an anchoring frame.

In order to deploy anchors 610 into the tissue to anchor the anchoring frame 600 of FIG. 15A, deployment member 612 in this case is provided to slide over rail 618 as illustrated in the end view of FIG. 15B (anchors 610 are not shown, for simplicity of illustration, since the mechanism for driving the anchors 610 by driver 613 is the same as that described with regard to FIG. 13B above). Deployment member 612 includes an enlarged driver 613 that is located in the channels formed on both sides of neck 616n that is located distally of anchors 610, prior to deployment, and a cable or wire 614 that extends proximally from driver 613 and out the proximal end of anchoring frame 600. Cable/wire 614 has sufficient length so that when anchoring frame is placed in position on the target area in the abdominal cavity to which it is to be anchored, the proximal end portion of cable/wire 614 still extends out of the patient 1 (such as out of the incision 223 in the procedure described above, for example).

When frame 600 is positioned in the abdominal cavity at the target location where it is to be anchored, e.g., against the abdominal wall, frame 600 is held motionless against the target area while deployment member is retracted proximally. If frame 600 is a flexible frame, constant pressure is exerted in a distal direction against the frame to ensure that it remains buckled/bent against the target area, so that it conforms to and contacts the target surface (e.g., abdominal wall). By pulling on cable/wire 614 while holding frame 600 substantially motionless, deployment driver 613 is retracted proximally to slide along rail 618. As it is retracted, driver 613 contacts anchors 610 on both sides of neck 618n, thereby driving them out through openings 606 and into the tissue, thereby anchoring frame 600 to the tissue as desired. Upon completely withdrawing deployment member 614/driver 613, rail is then unobscured by driver 613, so that the channel 608 of device 10 can be slid thereover.

Figure 15D:
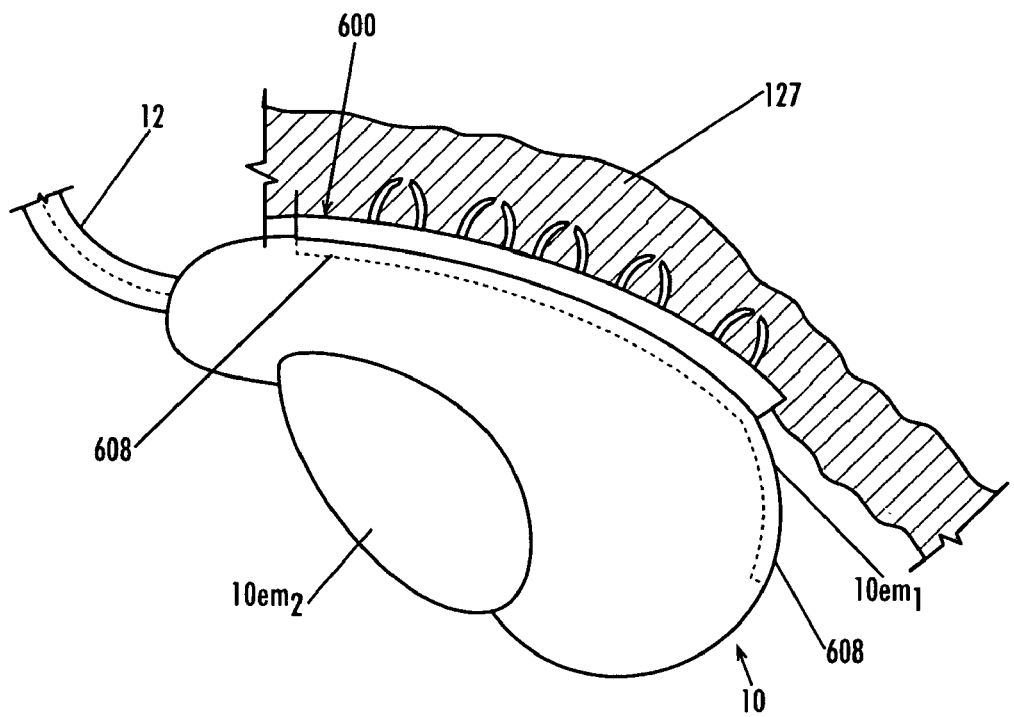
FIG. 15D shows the device of FIG. 15C having been mounted on an anchoring frame.

FIG. 15C shows an end view of device 10 having one configuration (T-shaped cross-section) of channel 608 configured to slide over rail 618 to secure device 10 to anchoring frame 600. FIG. 15D shows device 10 of FIG. 15C having been mounted on anchoring frame 600 of FIGS. 15A-15B. Note that channel 608 can extend over a length of device 10 that is much greater than the length of frame 600, to provide guidance of delivery of the distal end of the device, even though the distal end of device 10 is not engaged with frame 600 when device 10 has been installed in the intended position as shown in FIG. 15D.

Figure 15E:
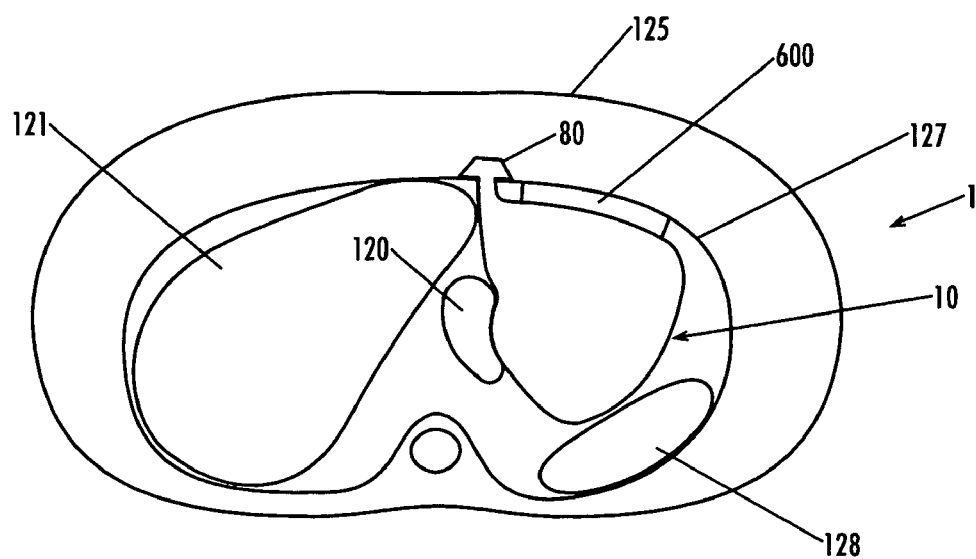
FIG. 15E is a schematic, sectional illustration (viewed from the foot of the patient with the patient lying on his back) of a device anchored to the abdominal wall via an anchoring frame.

FIG. 15E is a schematic, sectional illustration (viewed from the foot of the patient with the patient lying on his back) of device 10 anchored to the abdominal wall 127 via anchoring frame 600, with device 10 shown in an expanded configuration.

Figure 16A:
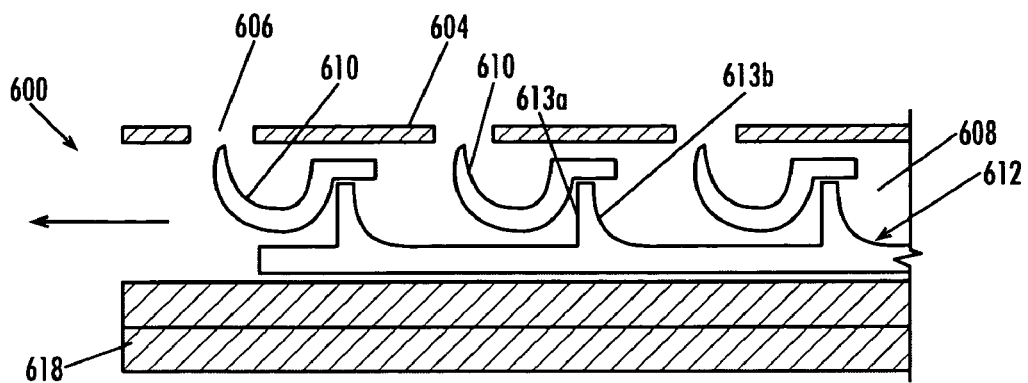
FIG. 16A illustrates an embodiment of an anchoring frame that includes an actuation mechanism that can be use to anchor the frame to tissue (deploy) as well as to release the frame from such anchoring.
Figure 16B:
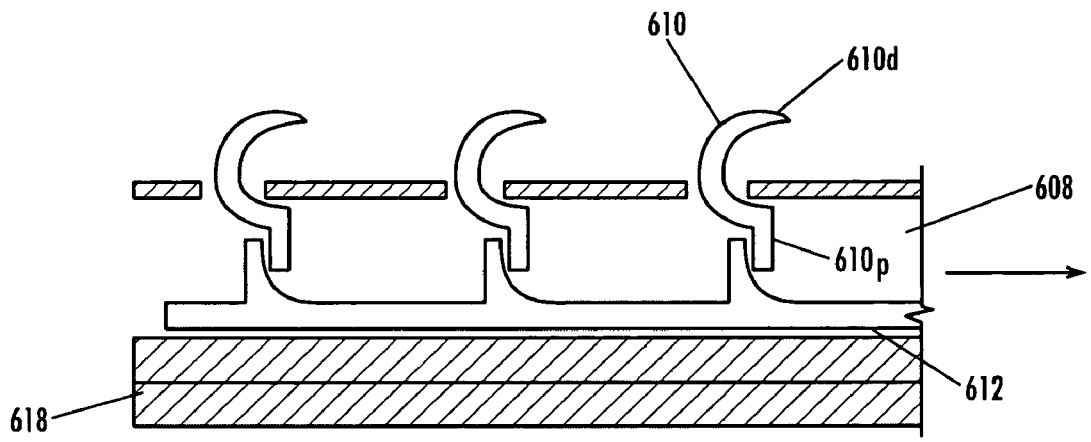
FIG. 16B illustrates the sharp (distal) ends of anchors deployed out through openings in the contact surface of the anchoring frame.

FIG. 16A illustrates an embodiment of an anchoring frame 600 that includes an actuation mechanism that can be use to anchor the frame 600 to tissue (deploy) as well as to release the frame 600 from such anchoring. In this case, deployment member 612 is provided in a channel 608 above a rail 618 that is configured to receive device 10 thereover, and deployment member 612 is configured to not only anchor the frame 600 to a tissue surface, but is also operable to reverse this anchoring, so as to allow removal or repositioning and re-anchoring of frame 600. Thus, the enlarged members or drivers 613 of deployment member 612 include deployment driver surfaces 613a and retraction driver surfaces 613b as illustrated in FIG. 16A. Upon sliding deployment member 612 relative to frame 600 in a direction to contact deployment driver surfaces 613a with anchors 610 (i.e., to the left, as shown in FIG. 16A) and continuing to slide deployment member 612 in that direction, deployment driver surfaces 613a drive anchors to rotate so as to extend the sharp (distal) ends of anchors out of openings 606, as illustrated in FIG. 16B. Deployment driver surfaces 613a are abrupt or steep and may even be formed as substantially perpendicular to the longitudinal axis of frame 600. Retraction driver surfaces 613b are ramped or cammed so as to allow the rotation of the opposite (proximal) ends down into channel 608 without contacting deployment member 612 during deployment of the distal ends.

Thus, FIG. 16B illustrates anchors 610 in the deployed configuration, wherein, when contact surface 604 is contacted to a tissue surface and anchors 610 are deployed in this manner, this anchors frame 600 to the tissue. Should the operator wish to remove anchoring frame 600, or reposition it, deployment member 612 is slid in the opposite direction relative to frame 600 (i.e., to the right in FIG. 16B). This causes retraction driver surfaces to contact the proximal ends 610p of anchors 610, and continued movement of deployment member 612 causes drivers 613p to reverse rotate anchors 610 to the positions shown in FIG. 16A. These deployment and retraction functions are repeatable. That is, after retracting the anchors 610 as described, anchoring frame can be repositioned on a tissue surface, and deployment member 612 can be actuated again to deploy anchors 610 and thereby anchor the frame 600 to the new location.

Figure 16C:
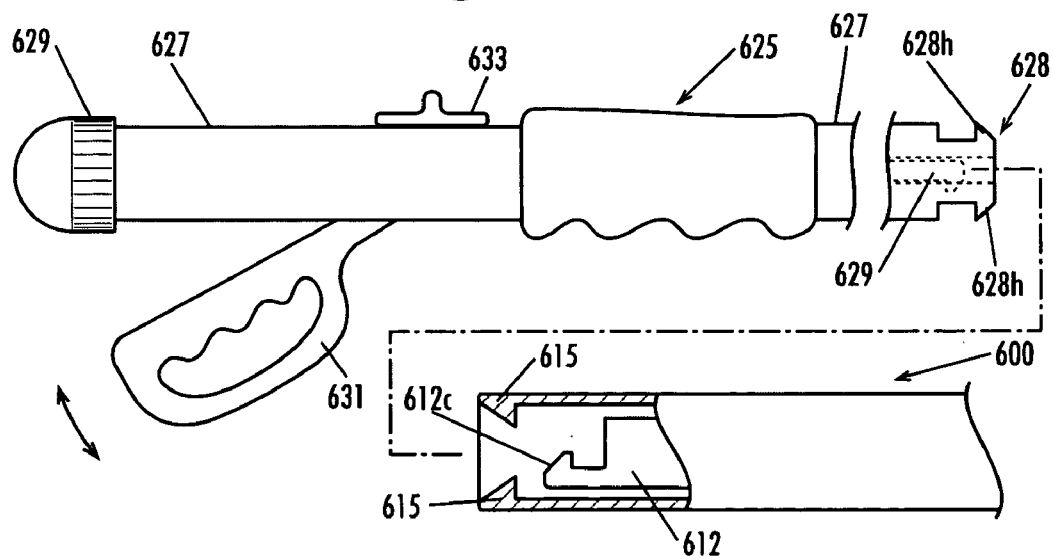
FIG. 16C illustrates a tool configured to engage with the deployment member and anchoring frame shown in FIGS. 16A-16B.

FIG. 16C illustrates a tool 625 configured to engage with deployment member 612 and anchoring frame 600 and, when engaged, can be used to move, orient and position anchoring frame, as well as operate deployment member 612 to deploy anchors 610 and/or retract anchors 610. Tool 625 includes an elongated shaft 627 having sufficient length so that when tool 625 is engaged with anchoring frame 600 and deployment member 612 in a manner as described hereafter, a proximal end portion of tool 625, including actuators to be manipulated by a surgeon or other user, extend out of the body of the patient 1, even when frame 600 has been inserted into the abdominal cavity as far as it needs to be advanced to anchor it at a desired location. The distal end of tool 625 includes a quick release mechanism 628 configured to engage with engagement features 615 on a proximal end portion of anchoring frame 600. For example, quick release mechanism 628 may include a plurality of hooks or teeth 628h that engage with engagement features 615 provided as mating or interengaging hooks to teeth. The hooks or teeth 628h can be drawn toward one another, radially inwardly, such as by rotation of quick release actuator 629, for example, so that they no longer engage with engagement members 615, but can be slid therepast, quickly releasing tool 625 from anchoring frame 600.

A cam driver 629 is formed at a distal end of a cam driver shaft 629d that is axially drivable with respect to shaft 627 by pivoting cam driver actuator 631 relative to shaft 627. A slidable safety lock 633 may be provided on shaft 627 that is slidable in a first direction to prevent pivoting of actuator 631 relative to shaft 627, thereby preventing inadvertent deployment or retraction of anchors 610 when cam driver 629 of tool 625 is engaged with deployment member 612, such as by engagement with cam driver engagement member 612c, for example. By sliding safety lock 633 in the opposite direction, this unlocks actuator 631 and the operator can then either pivot actuator 631 toward shaft 627 to drive deployment member 612 to deploy anchors 610, or pivot actuator 631 away from shaft 627 to retract anchors into anchoring frame 600. Upon quick release of tool 625 from frame 600 as described, cam driver 629 can be released from cam drive engagement member 612c by simply rotating tool 625 about its longitudinal axis so that cam driver 629 and engagement member 612c become misaligned.

Figure 17:
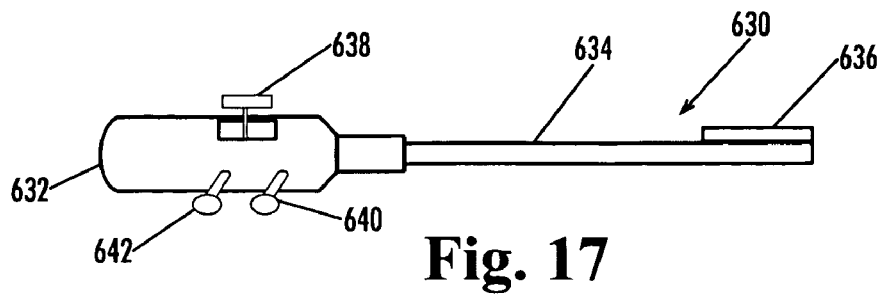
FIG. 17 illustrates an anchoring frame deployment tool that can be used for percutaneous delivery of an anchoring frame.

FIG. 17 illustrates an anchoring frame deployment tool 630 that can be used for percutaneous delivery of anchoring frame 600. Tool 630 includes a handle 632 for manual operation by a user (e.g., surgeon) and an elongated, rigid shaft 634 extending distally therefrom. An engagement feature 636 is provided on shaft 636 for engaging with anchoring frame and securing it during the delivery thereof. For example, engagement feature may be a rail, e.g., a t-shaped rail or other cross sectional configuration that slides within a channel in frame 600, somewhat like a tongue-and-groove fitting, or may include a channel that slides over a rail portion of frame 600, etc. An actuator 638 is provided on handle 632 that is actuatable to trigger staples or other mechanical members 610 to be driven through the openings in frame 600 to extend through the surface 604 and into the target internal abdominal structure (e.g., abdominal wall) to anchor frame 600 thereto. One or more lumens may be provided through shaft 634 for delivery of irrigating fluids (or other substances) and for application of suction to the distal end of shaft 634, via ports 640 and 642, respectively.

Figure 18A:
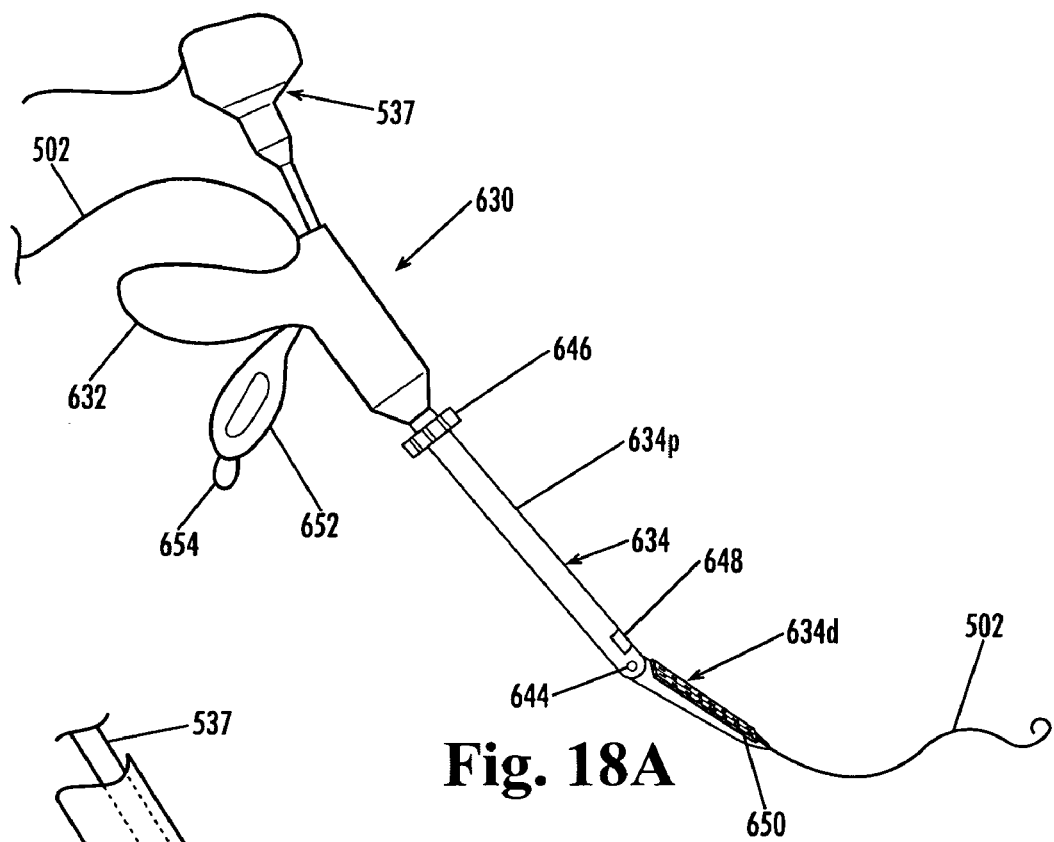
FIG. 18A illustrates another embodiment of an anchoring frame deployment tool.

FIG. 18A illustrates another embodiment of an anchoring frame deployment tool 630 that is configured to receive an endoscope 537 therein to facilitate viewing of the placement of anchoring frame 600. A video camera 538 may be provided on endoscope 537 so as to monitor the visualization on a screen, or, optionally, viewing may be performed directly through an ocular.

Shaft 634 articulates, via one or more articulating joints 644. An articulation actuator 646 is provided on or near handle 630 for operation by a user to control the articulation of a distal portion 634d of shaft 634 with respect to a proximal portion 634p of shaft 634. In the example shown, articulation actuator 646 is a rotatable wheel that is rotatable in a first direction to articulate distal portion 634d in a first angular direction about joint 644, while rotation of actuator 646 in the opposite direction articulates distal portion 634d in the opposite direction. Articulation actuator 646 and/or articulation joint 644 provide frictional resistance, so that when actuator 646 is not being rotated, distal portion 634d is maintained in its orientation relative to proximal portion 634p.

A window or opening 648 is provided proximally of articulating joint 644 to enable viewing through the distal end of endoscope 537 that is positioned in shaft 634 at the location of opening/window 648 when endoscope 537 is inserted into tool 630. Window/opening 648 may be an opening (e.g., cutout), or may be a window, e.g., a cutout that is sealed over with a transparent material.

Figure 18B:
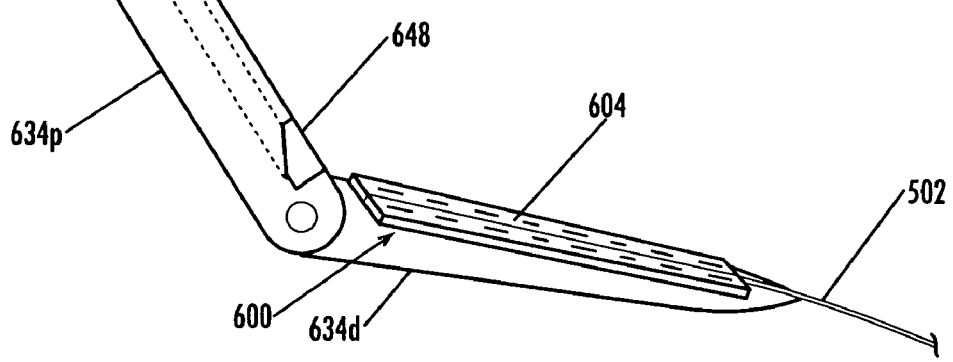
FIG. 18B is an enlarged partial illustration of the tool of FIG. 18a showing the distal end portion.

Distal portion 634d includes a recess or cavity 650 configured to receive anchoring frame 600 therein. Thus, recess or cavity 650 is shaped and dimensioned to receive anchoring frame 600 therein and to confine anchoring frame 600 from movements axially with respect to the longitudinal axis of distal portion 634d. Frame 600 may be received in recess, cavity or slot 650 by friction fit and/or a releasable clamping mechanism (not shown, see co-pending application Ser. No. 11/716,986, FIGS. 36A-36D and description thereof) may be optionally provided on opposite sides of slot, recess or cavity 650 for releasably clamping frame 600 wherein it is received therein, with clamping and releasing motions being controlled by a clamp actuator (not shown, see co-pending application Ser. No. 11/716,986, FIGS. 36A-36D and description thereof). application Ser. No. 11/716,986 is hereby incorporated herein, in its entirety, by reference thereto. FIG. 18B shows an enlarged partial view of shaft 634 with anchoring frame 600 mounted within distal end portion 634d, and showing the distal end of endoscope 537 within proximal end portion 634p.

In use, after insertion and placement of guidewire 502, such as in a percutaneous procedure as described above, deployment tool 630 is passed over guidewire 502, with the proximal end of guidewire first being inserted into the distal end of shaft 634, through shaft 634 and handle 632 and proximally out of handle 632, as illustrated in FIG. 18A. By insertion of tool 630 into the abdominal cavity, the abdominal wall (e.g., the anterior abdominal wall can be directly visualized by endoscope 537/camera 538 viewing through opening/window 648. This visualization is performed to ensure that that is no tissue located between the anchoring site (e.g., anterior abdominal wall 127) and anchoring frame 600 prior to anchoring the frame 600 to the anchoring site. Once it has been visually confirmed that there is no tissue intervening between frame 600 and the anchoring site, actuator 646 is manipulated to rotate distal portion 634d up against the anchoring site, thereby contacting surface 604 to the anchoring site. Anchors 610 are then deployed into the anchoring site, such as by a mechanism described above for example. In an alternative embodiment, needles and sutures may be substituted for anchors 610, such as described in application Ser. No. 11/716,986, FIG. 36C and description thereof). A deployment actuator 652, such as a trigger, lever or other equivalent mechanical actuator can be provided on handle 632 for operation by the user. Thus when actuator 652 (FIG. 18A) is actuated, this retracts enlarged member 613 to drive anchors 610 into the tissue, thereby anchoring the frame 600. Deployment actuator may be provided with a safety mechanism or lock 654 that can be locked up until the time that the operator is ready to deploy the anchors 610, to prevent inadvertent deployment of anchors 610 before the frame 600 has been properly positioned and is ready to be anchored.

Figure 19A:
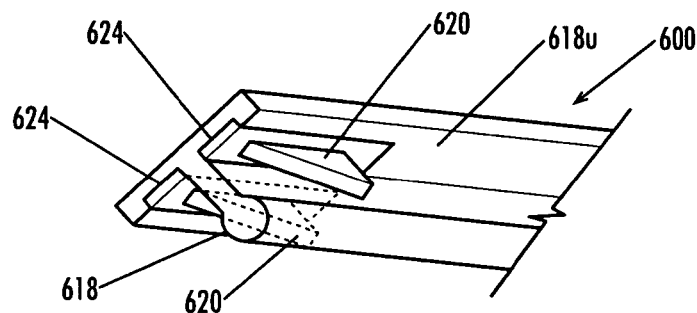
FIG. 19A illustrates locks on an end portion of an anchoring frame.
Figure 19B:
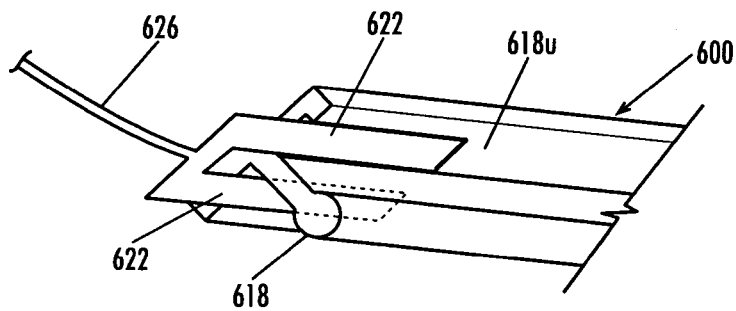
FIG. 19B illustrates tabs being inserted to depress the locks of FIG. 19A.

When device 10 has been fully inserted into its intended position relative to anchoring frame 600, device is locked into this position by automatic lock 620. FIGS. 19A-19B show one embodiment of an automatic lock 620 that may be provided on the proximal end of frame 600 on the underside of the top portion of track 618. FIGS. 19A and 19B show partial views of anchoring frame 600 with anchors 610 not being shown for simplicity of illustration. In FIG. 19A, locks 620 are shown deployed. Locks 220 may be spring steel or some other biased members that are biased toward the deployed configuration shown in FIG. 19A, while being deformable so as to lie substantially parallel or flush with the underside. Thus, when the channel 608 rides over the enlarged portion 618 at the bottom of the rail, in this case in a tongue and groove type of interfit, the top surfaces on opposite sides of slot 608 contact the undersurface 618u of the top portion of the frame 600 and are guide therealong. As the top surfaces ride over automatic locks 620, they depress them towards the undersurface so that the device is able to slide along the rail. Once the entire channel 608 of device 10 has passed locks 620 (distally thereof), locks resiliently spring back into the conformation shown in FIG. 19A, thereby preventing device 10 from being retracted proximally back off of frame 600. Detents and/or other stopping structure (not shown) are provided at the distal end portion of the frame 600 to prevent channel 608 from being slid too far distally with respect to anchoring frame 600/enlarged portion 618.

Prior to anchoring the frame 600 to the desired target tissue, automatic locks are held recessed (in an unlocked configuration) against the undersurface 618. This is necessary to allow the retraction of the enlarged member 613 of deployment member 612 during deployment of anchors 610. For example, lock prevention tabs 622 may be inserted in slots 624 to maintain a biasing force on locks 620 to keep them in the unlocked configuration. Tabs 622 may be integrated, such as to form a U-shaped member like shown in FIG. 19B and a wire or suture 626 extends proximally therefrom and has a length sufficient to extend out of the patient 1, even when frame 600 is located in its intended anchoring position. After enlarged member 613 has been retracted through frame 600 to drive anchors 610 into the target tissue, in a manner as already described above, and deployment member 612/enlarged member 613 has been removed from anchoring frame 600, the operator pulls on wire/suture 626, thereby sliding tabs 622 out of their respective positions and removing tabs 622 form anchoring frame 600. Upon this removal, locks 620 resiliently spring back into the locked configuration shown in FIG. 19A.

Figure 20A:
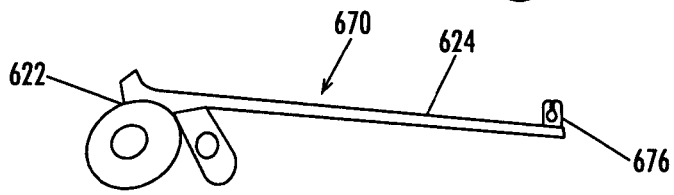
FIG. 20A shows an anchoring frame unlocking tool that can be used to unlock an anchoring frame to free a device that has been automatically locked into position along the anchoring frame.

FIG. 20A shows an anchoring frame unlocking tool 670, that can be used to unlock the anchoring frame to free device 10 that has been automatically locked into position along anchoring frame 600. For example, it may be difficult to remove frame 600 if tissue has ingrown into tissue ingrowth surfaces provided on surface 604, so this removal mechanism makes it much easier to remove the expandable member(s)

Figure 20B:
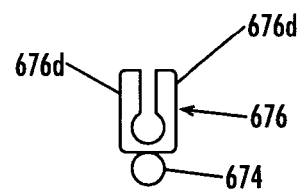
FIG. 20B illustrates an end view of the distal end of the tool of FIG. 20A.

10*em* for replacement, or withdrawal if no longer indicated. Tool 670 includes a handle 672, and elongated shaft 674 and a lock depressor 676 at the distal end of shaft 674. Lock depressor 676 is configured to be mounted and slide over rail 618 and includes depressor portions 676*d* that extend above the portion that fits over rail 618 and that press against automatic locks 620 to depress them to the unlocked configuration as depressor 676 is slid over the rail 618. FIG. 20B shows an end view of tool 670 that illustrates a configuration of a lock depressor 676 according to one embodiment. Optionally, an actuator 678 may be provided to actuate the depressor portions form a retracted configuration to the extended configuration shown in FIG. 20B.

Figure 20C:
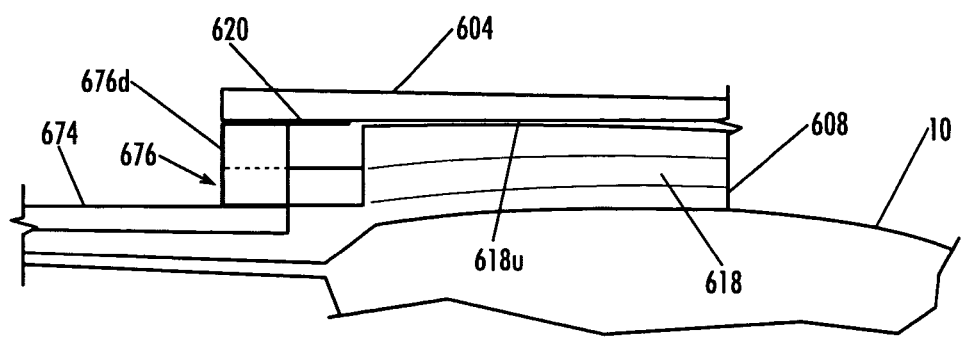
FIG. 20C schematically illustrates use of the tool of FIG. 20A to unlock a device from an anchoring frame so that the device can be removed from the site.

FIG. 20C schematically illustrates use of tool 670 to unlock device 10 from anchoring frame 600 so that device 10 can be removed from the site. Tool 670 is inserted (e.g., through incision 233 in the percutaneous procedures described above, or along any other approach provided by other procedures, such as mini-laparoscopic, laparoscopic, open, etc.) and lock depressor 676 is mounted over rail 618. Tool 670 is then distally advanced over rail 618. As lock depressor 676 advances distally, it depresses the automatic locks 620, as shown. Upon full depression of locks 620, or simply by distally advancing tool 670 until lock depressor 676 contacts the proximal end of channel 608 of the device 10, device 10 is now ready to be removed off of frame 600. By applying retraction force to conduit 12, channel 608 slides proximally over channel 618, thereby withdrawing device 10 and tool 670 together. Tool 670 may be operated to maintain contact with the proximal end of channel 608 to ensure that locks 620 remain unlocked as channel 608 is withdrawn thereover. In an alternate method, locks 620 may be formed with thin enough material so that an impulsive tug on conduit 12 is sufficient to bend locks 620 over backwards to allow channel 608 (and thus device 10) to be withdrawn off of frame 600.

Figure 21A:
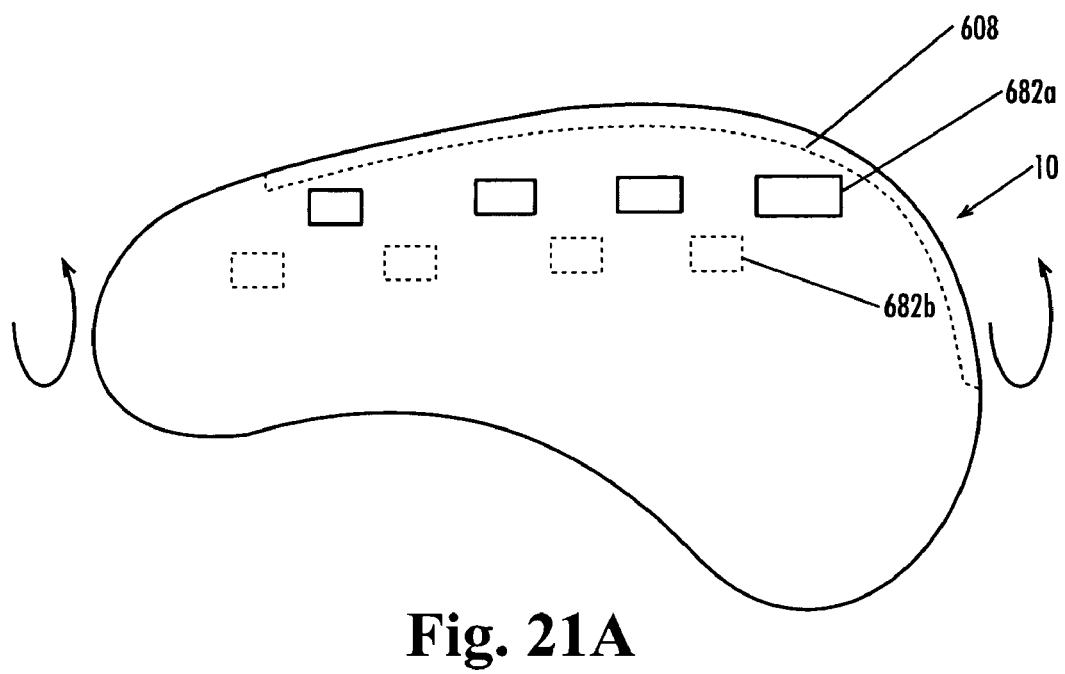
FIG. 21A illustrates an embodiment of a device provided with looped tabs.
Figure 21B:
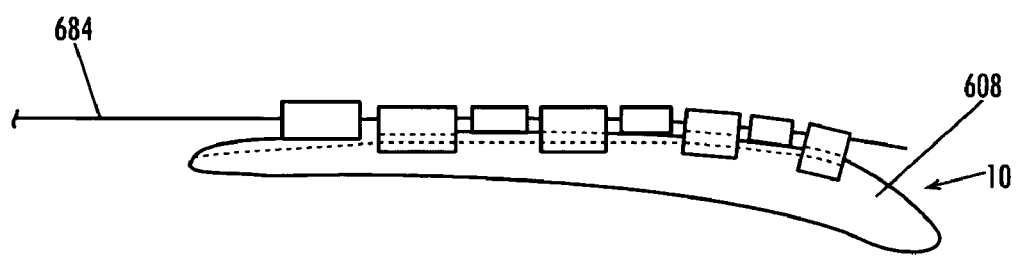
FIG. 21B illustrates the looped tabs of FIG. 21A aligned with each other, with a rod or wire inserted through the loops to maintain the device in a rolled up configuration.

As noted above, device 10 is provided in a compact (non-expanded) configuration during delivery, at least when delivering by a percutaneous, mini-laparoscopic or laparoscopic procedure. FIG. 21A illustrates an embodiment of device 10 provided with looped tabs 682, with one set 682*a* extending lengthwise (e.g. relatively aligned along channel 608) on one side of expandable member 10*em*, and an alternating set 608*b* on the opposite side of the expandable member 10*em*. With expandable member in a deflated configuration, expandable member can be rolled in the direction indicated by arrows in FIG. 21A about its longitudinal axis, so that the expandable member 10*em* is rolled up on itself to form a compact structure resembling a cylinder. Once rolled up into this configuration, looped tabs 682*a* and 682*b* align with each other and a rod or wire 684 can be inserted through the loops of looped tabs 682*a*,682*b* to maintain device 10 in the rolled up configuration, as shown in FIG. 21B. It is noted that channel 608 is still exposed on an external surface of the device even when in the rolled up condition, so that it can be mounted and slid over rail 618 during the delivery of device 10. Once device 10 has been positioned over frame 600/rail 618 in the desired location, wire 684, which has sufficient length to extend out of the patient even when device 10 is mounted in the intended position on frame 600, can be withdrawn by an operator, thereby freeing the expandable member. Upon inputting of gas and/or liquid to expandable member 10*em*, it unfurls and assumes its expanded configuration. Although devices that are attached by an anchoring frame 600 typically will not require further anchoring, it is noted that such procedures are not limited to anchoring using only the anchoring frame, as any of the other attachment or anchoring techniques and features may optionally be used in addition to anchoring with an anchoring frame 600. In this regard, it is noted that looped tabs 682 may be used as attachment areas, e.g., through which sutures, staples or tacks, etc. may be driven to further attach device 10 to the patient. Still further, whether or not used to attach device 10, looped tabs also provide convenient and safe areas for manipulation by the use of tools, such as graspers, etc. It is further noted that this type of compaction feature can be provided for devices that are not attached to an anchoring frame 600, but are attached by other means described herein, or are attached only by attaching tabs 682 to tissues within the patient.

Figure 21C:
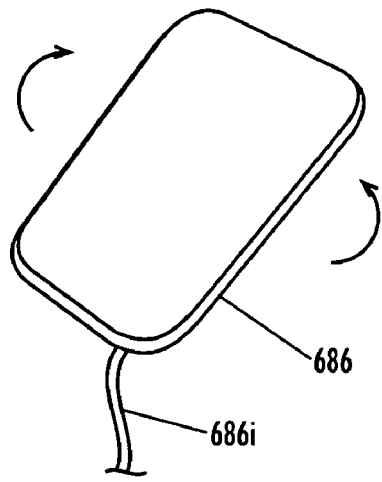
FIG. 21C illustrates an expandable compaction member that may be formed to roll up when inflated, but can be opened up or spread apart or held open in a relatively flattened out configuration in its non-expanded (deflated) state.
Figure 21D:
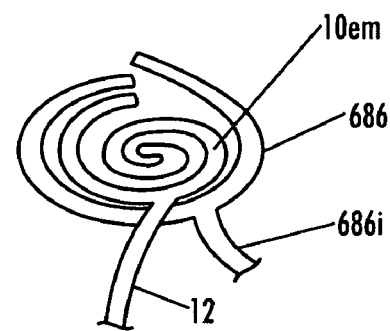
FIG. 21D shows the compaction member of FIG. 21C maintaining a device in a compacted or collapsed configuration.

Alternatively, an expandable compaction member 686 may be provided to surround and compact expandable member 10*em* for delivery thereof as illustrated in FIGS. 21C-21D. For example, expandable compaction member 686 may be a thermoformed balloon that is formed to roll up when inflated, but can be opened up or spread apart or held open in a relatively flattened out configuration in its non-expanded (deflated) state as illustrated in FIG. 21C. This open configuration allows a rolled up or otherwise compressed expandable member to be placed on expandable compaction member 686. Expandable compaction member 686 is then inflated/expanded via conduit 686*i*, whereupon it assumes its rolled-up configuration, thereby substantially surrounding the compacted expandable member 10*em* as illustrated in the end view of FIG. 21D. In this configuration, the expandable member 10*em* and compaction member 686 are deliverable into the abdominal cavity for location at the intended surgical target site.

Once in the intended surgical target site, i.e., in the location where it is desired to expand the expandable member 10*em*, compaction member 686 may then be deflated and then withdrawn from its encapsulation of expandable member 10*em* and from the abdominal cavity. Optionally, expandable member may first be attached to a rail or to some other fixation point to prevent it from being withdrawn as compaction member 686 is withdrawn. After removal of compaction member 686, expandable member 10*em* can be expanded in the course of a procedure as described with regard to any of the embodiments described herein or in any of the disclosures for which priority has been relied upon.

Figure 21E:
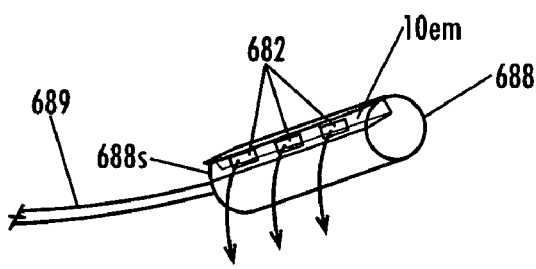
FIG. 21E illustrates a rigid exoskeleton provided to receive an expandable member and maintain it in a compressed or otherwise non-expanded configuration.

FIG. 21E illustrates another embodiment in which a rigid exoskeleton 688 is provided to receive expandable member 10*em* and maintain it in a compressed or otherwise non-expanded configuration for delivery into the surgical target area. For example, exoskeleton may be in the form of a rigid canister as illustrated in FIG. 21E, that functions similar to a film canister for 35 mm film. That is, expandable member 10*em* can be rolled up or otherwise inserted into canister 688 to be retained therein in a non-expanded state. Typically, at least an edge of the expandable member 10*em* will be left slightly protruding from the opening or slot 688*s* provided in exoskeleton 688. In the example shown in FIG. 21E, the edge of expandable member 10*em* protruding from opening 688*s* includes tabs 682, looped tabs 682*a* or other features for engaging with a rail or other anchored structure in the abdominal cavity 682. In the case of looped tabs 682, of other feature for engaging a rail or other fixed structure, these features can be looped over or otherwise engage with the fixed structure in the abdominal cavity when the exoskeleton containing the compressed or otherwise non-expanded expandable member is inserted into the surgical target location in the abdominal cavity. Upon fixing the looped tabs 682*a* or other feature to the rail or other fixed structure, expandable member 10*em* can then be extracted from exoskeleton 688 by rotating exoskeleton 688 in a rotational direction opposite to the direction of the arrows shown in FIG. 21E. This causes extraction of the expandable member 10em out of the exoskeleton 688 as illustrated by the directional arrows shown in FIG. 21E. Rotation can be effected by a rod or wire 689 that is fixed to a proximal end portion of exoskeleton 688 and which may be rigid or flexible, but is torsionally rigid in either case. Alternatively, rigid exoskeleton 688 can be retracted in a linear direction opposite the directional arrows shown in FIG. 21E. This motion, applied against the force provided by the fixation of expandable member 10em relative to at least one fixed structure in the abdominal cavity, cause extraction of expandable member 10em out of rigid exoskeleton 688 as rigid exoskeleton 688 moves away from the fixed/anchored portion of expandable member 10em.

If tabs 682 are provided on the edge of expandable member 10em, one or more of tabs 682 may be temporarily or permanently anchored to a structure in the abdominal cavity, e.g., by suturing, stapling, tacking and/or adhesives or other alternative fixing members or substances, and then an unrolling motion like that described above can be carried out to extract the expandable member 10em. Alternatively, or if no additional features are present on the edge of the expandable member 10em, one or more tabs 682 or the edge of the expandable member 10em can be grasped, by graspers, or other long slender tool and then exoskeleton 688 can be rotated as described. In any of the procedures described above, once expandable member 10em has been completely extracted from exoskeleton 688, exoskeleton 688 is withdrawn out of the patient to provide working space for continuing procedures to implant device 10.

Figure 21F:
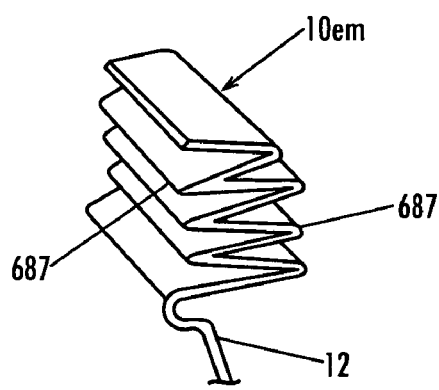
FIG. 21F shows an alternative configuration for placing an expandable member in a compacted or collapsed configuration.

FIG. 21F shows still another alternative configuration for placing expandable member 10em in a compacted or collapsed configuration for delivery into the abdominal cavity to the surgical target area. In this example, expandable member is folded into an accordion-fold configuration so that the expandable member is folded over on itself along folds 687, similar to the way that a bicycle tube is packaged for sale. In this folded configuration, expandable member 10em can be received in an exoskeleton 688 such as described above, or can be delivered via a sheath, for example. Additionally or alternatively, expandable member 10em can be temporarily retained in the folded configuration by attaching the adjacent pleats or folds together using weak adhesive bonds that are broken when expandable member 10em is expanded, by the force of the inflation fluid pressure, for example.

Figure 21G:
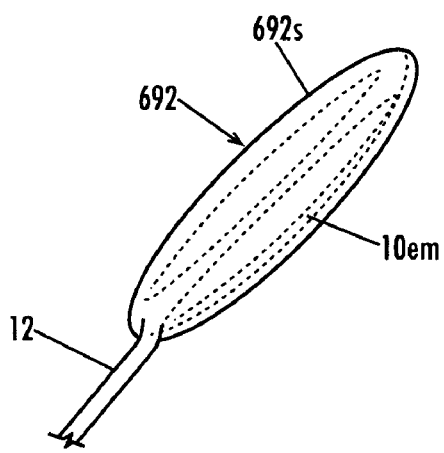
FIG. 21G shows an expandable member compressed in a capsule that is formed of a water soluble gel or skin.

In another embodiment, expandable member 10em may be compressed in a capsule 692 that is formed of a water soluble gel or skin 692s as illustrated in FIG. 21G. In this case, the compressed expandable member 10em is inserted into the abdominal cavity and to the surgical target area location while soluble skin 692s maintains expandable member 10em compacted. As capsule 692 enters the aqueous environment of the abdominal cavity, skin 692s begins to dissolve. After a predetermined amount of time in the aqueous environment of the abdominal cavity, skin 692 has dissolved by a sufficient amount such that the input of expansion media into expandable member 10em causes expandable member 10em to expand with sufficient force to rupture capsule 692 if is has not dissolved to the extent where it has ruptured simply by dissolution. In either case, capsule 692 can be retracted out of the patient, using graspers, for example, but need not be, as it will completely dissolve with the passage of additional time.

Figure 21H:
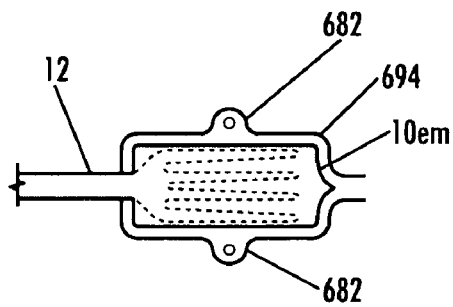
FIG. 21H illustrates an embodiment having a flexible, expandable exoskeleton.

FIG. 21H illustrates an embodiment having a flexible, expandable exoskeleton 694. In this example, expandable member 10em is surrounded by expandable exoskeleton 694, which may be a pleated silicone capsule (or balloon), for example, or partially slitted silicone capsule or balloon, or may have either of these structures and be formed from polyurethane or other biocompatible elastomer, for example. Exoskeleton 694 is formed so that it maintains the compacted configuration shown in FIG. 21H as long as expandable member 10em does not contain an expansion medium or fluid. After placement of the exoskeleton 694 containing expandable member 10em at the desired surgical target site, exoskeleton 694 is inflated by inputting expansion medium (e.g., gas or liquid) through a lumen in conduit 12, and expansion medium is inputted through another lumen in conduit 12 causing expansion of expandable member 10em. Alternatively, expansion medium inputted through conduit 12 to expandable member 10em can expand both expandable member 10em and exoskeleton 694 simultaneously, with the pleats or slits assisting the expansion. Exoskeleton 694 may be provided with one or more tabs 682 that can be used to anchor the exoskeleton 694 in the expanded configuration, and this may also help to maintain expandable member 10em in the desired expanded volume, as exoskeleton 694 supports some of the load applied to device 10 caused by expansion of the device against the structures in the abdominal cavity.

Figure 21I:
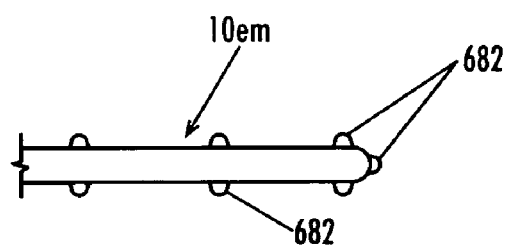
FIGS. 21I-21J illustrate an expandable member that is formed in an elongated tube configuration.
Figure 21J:
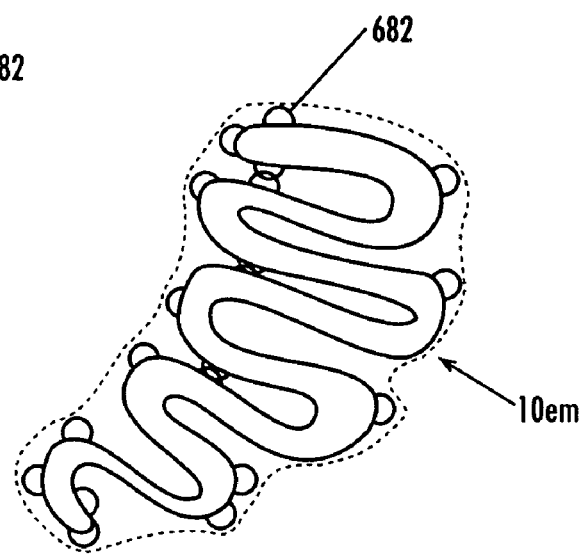

FIGS. 21I-21J illustrate an expandable member 10em that is formed in an elongated tube configuration. This tube formation allows expandable member 10em to be linearly deployed through a small opening in a patient (or alternatively, may be used in an open surgical procedure). Tabs 682 are provided at spaced locations along the elongated tube, and act as fixation or anchoring points along the expandable member 10em. Thus, portions of the expandable member 10em can be anchored as they are inserted into and arrive at the surgical target area, such as by stapling, suturing, tacking, etc., tabs 682 to fixed structures within the abdominal cavity. In this way, elongated member can be laid out and fixed at the surgical target array in an almost infinite number of different configurations that are customizable according to the way that the user bends and fixes the portions of the expandable member. In the example shown in FIG. 21J, expandable member has been fixed in a serpentine configuration, but this embodiment in is in no way limited to this configuration, as a coiled configuration could be provided, or groups or bunches of portions could be configured, or many other customizable configuration can be fixed, including a more or less random distribution of the portions fixed to structures in the abdominal cavity.

Figure 21K:
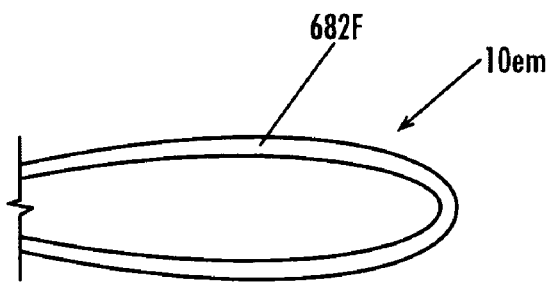
FIG. 21K illustrates an alternative to the use of tabs in the embodiment of FIGS. 21I-21J.

FIG. 21K illustrates an alternative to the use of tabs 682 in the embodiment of FIGS. 21I-21J. In this case, a flange 682F is provided along one or more continuous lengths of expandable member 10em, up to the full length of the expandable member 10em, to increase the flexibility of the choice of fixation points, since stapling, tacking or suturing can be performed anywhere along the one or more flanges 682F. It is noted that this alternative feature is not limited to the elongated tubular form of an expandable member, as one or more flanges 682 may be provided along any of the expandable members 10em described herein.

Figure 22A:
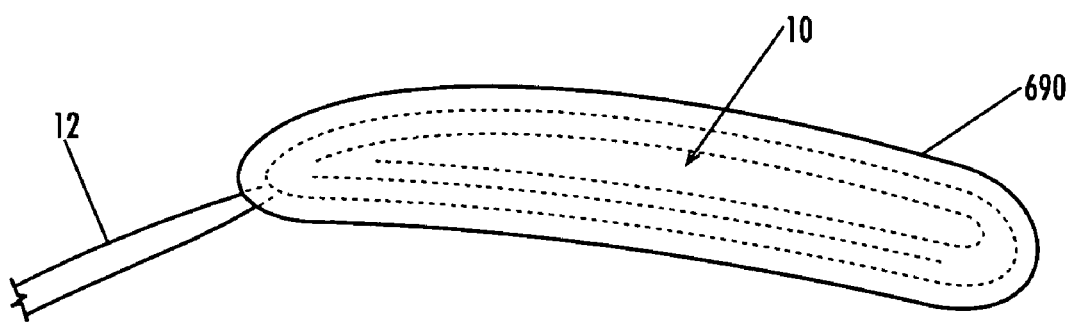
FIG. 22A illustrates a device maintained in a compact configuration by insertion within a sheath.

In another embodiment, device 10 is compacted and maintained in a compact configuration by insertion within a sheath 690 as illustrated in FIG. 22A. Sheath 690 does not completely encircle expandable member 10em, but includes a slit through which a rail or channel connected to expandable member 10em, and which is to be connected to frame 600, is exposed. Device 10 can be compacted into a compressed form using any of a variety of techniques, including, but not limited to: rolling (like described above, but wherein looped tabs 682 are not required), accordion folding (like a bicycle inner tube when it is first purchased), tongue rolled (described in further detail below), randomly compressed by drawing and maintaining a vacuum on expandable member(s) 10*em*, or other folding and compressing.

FIG. 22B illustrates an expandable member 10*em* of device 10 being deployed via an introducer 696 having a splittable introducer housing at a distal end portion thereof. In the example shown, the distal end portion of introducer is split into two portions or jaws 696J that are pivotably mounted for rotation with respect to the remainder of the introducer 696, for example, via pivot joint 696P. However, it is noted that the distal end portion may be splittable into three or more component jaws 696P, as this embodiment is not limited to splitting using only two jaws 696P. It is further noted that jaws 696J do not have to form equal portions of the distal end of introducer 696 as shown. FIG. 22B shows expandable member 10*em* in a substantially flattened, non-expanded configuration, prior to further compacting it by rolling, accordion-folding, or otherwise further compacting the expandable member 10*em*/device 10 to be received in the splittable jaws 696J of introducer 696, that form a housing for the compacted expandable member 10*em* for delivery into the abdominal cavity. A structure referred to as a "doghouse" surrounds the conduit 12 where it connects to expandable member 10*em* and may form a socket into which conduit 12 is received. In any case, the doghouse strengthens the joint between conduit 12 and expandable member 10*em*, to minimize risk of failure at the joint. The doghouse may be made from the same material as conduit 12 and/or expandable member 10*em*. Conduit 12 extends trough the tube of the introducer 696 and out of a proximal end portion thereof when device 10 is loaded in the introducer 696.

FIG. 22C illustrates the compacted device 10 (including expandable member 10*em*) having been received in the introducer 696, with the splittable jaws 696J having been closed around the compacted expandable member 10*em* to maintain it in a compact configuration as it is delivered through opening 223 and through an opening formed in the abdominal muscle 127 for a percutaneous implantation procedure.

Figure 22D:
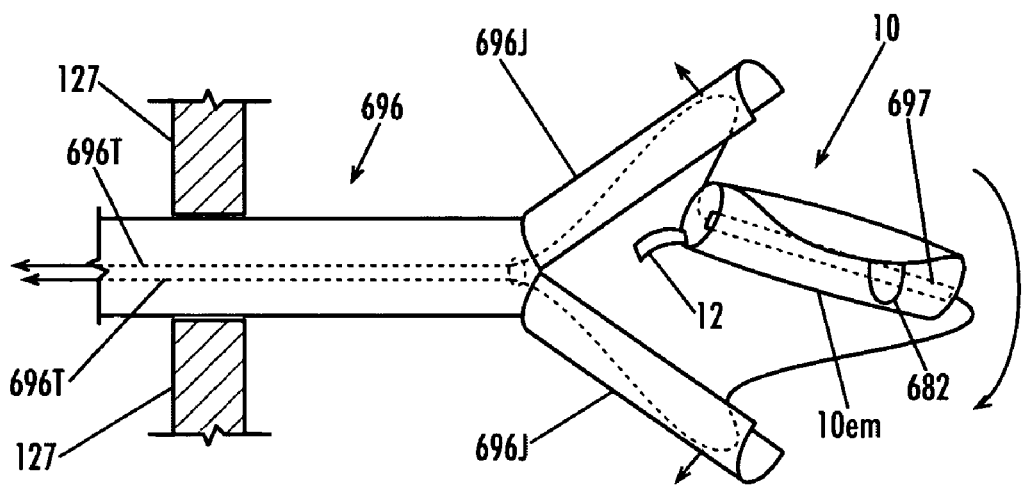
FIG. 22D illustrates rotation of the compacted expandable member by manipulation of tethers.

Once jaws 696J have completely passed through the opening in the abdominal muscle 127 and have been placed in the abdominal cavity in the vicinity of the desired location for placement of expandable member 10*em*, jaws 696J are opened by manipulation of tethers 696T extending through introducer 696 and out of a proximal end thereof for manipulation by a user. Tethers 696T, although provided as a pair of tethers at the proximal end of the introducer 696 and connected at the distal ends to a rod or roller 697 around which expandable member 10*em* has been rolled up in this example. Alternatively, tethers 696T can be formed as one continuous tether 696T having two proximal ends extending out of the proximal end portion of introducer 696 and around which expandable member 10*em* is rolled or folded at a distal end portion thereof. Upon applying tension to tethers 696T when the operator/user pulls on the proximal end portions of tethers 696T extending proximally from introducer 696 while maintaining the introducer 696 in a fixed position relative to the abdominal muscle 696, this rotates the compacted expandable member 10*em* (and roller 697, when present) as illustrated in FIG. 22D, thereby also opening jaws 696J. Alternatively, jaws 696J may operate like laparoscopic graspers to open and close and are therefore opened first before applying tension on tethers 696T to extract device 10 in a manner described above.

Figure 22E:
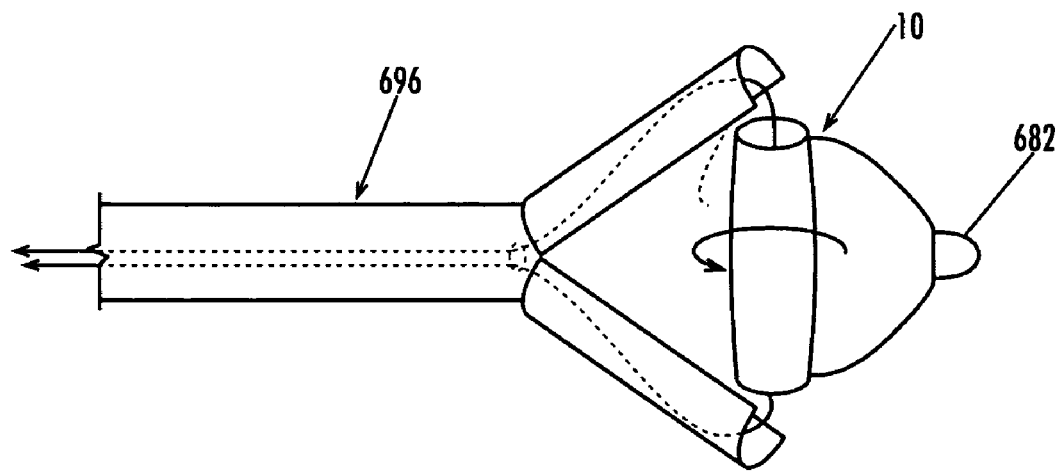
FIG. 22E illustrates the beginning of extraction of the expandable member.

When device 10 has been properly oriented with respect to introducer 696, as illustrated in FIG. 22E, one or more tabs 682 may be fixed to a structure in the abdominal cavity, and expandable member 10*em* can then be extracted from its compact configuration, such as by unrolling (in the embodiment shown) unfolding, or otherwise extracting the expandable member from the compact state it assumed to be received in the introducer 696, by withdrawing the introducer 696 as the distal end of expandable member is retained by the fixation. Alternatively, graspers or other instrument may be used to grasp a distal most tab or a distal portion of expandable member 10*em* to hold it relatively motionless as introducer 696 is retracted and thus drawn away from device 10, thereby extracting expandable member 10*em*, as the proximal ends of jaws 696 are retracted back into the opening through the abdominal muscle, this closes the jaws, allowing them to be completely removed from the abdominal cavity, taking tethers 696T (and optionally roller 697, if present) along with it. It should be noted that although device 10 is shown positioned substantially perpendicular to the longitudinal axis of introducer 696 as the desired orientation of the device 10 for extracting expandable member 10*em*, that this embodiment is not limited to this orientation. For example, a rolled up expandable member, as shown, may be oriented at an acute angle (in either direction) to the perpendicular to the longitudinal axis of introducer 696, depending upon various factors, such as the available working space, desired final orientation of the expandable member 10*em*, etc. Also, tabs 682, flange 682F or other attachment features can be anchored to structures within the abdominal cavity in an incremental fashion, as expandable member 10*em* can be incrementally extracted, a portion at a time, with anchoring being performed between incremental extraction steps.

FIGS. 22F-22H illustrate operation of another delivery tool for use in delivering and facilitation of anchoring of device 10 in the abdominal cavity. This tool also advantageously provides the ability to deliver device 10 by a percutaneous procedure or laparoscopic procedure. Of course, this tool can also be used in open procedures. The tool includes an inner sheath/delivery shaft 696*i* about which expandable member 10*em* can be rolled. In the example illustrated in FIG. 22G, expandable member 10*em* has been folded over and then rolled up around the distal end portion of inner sheath/delivery shaft 696*i*. A portion of delivery shaft/inner sheath 696*i* proximal of the portion about which expandable member 10*em* is rolled, may be formed in a bend 696*b* as shown in FIG. 22G. Inner sheath/delivery shaft 696*i* may be formed to have the bend 696*b* as shown in FIG. 22G, when in an unbiased configuration, but is flexible so that inner sheath/delivery shaft 696*i* can be biased into a substantially straight configuration. Alternatively, bend 696*b* may be formed as a pivoted or hinged joint, which can be operated upon retraction of outer sheath 696*o* therefrom.

As shown in FIG. 22F, an outer sheath 696*o* is provided that slides freely over inner sheath 696*i*. After compacting expandable member 10*em*, such as by rolling it around the distal end portion of inner sheath 696*i*, the distal end portion of inner sheath 696*i* is biased to substantially straighten inner sheath 696*i*, and outer sheath 696*o* is slid distally over inner sheath 696*l* to cover the expandable member 10*em* and maintain it in a compact or compressed configuration as shown in FIG. 22F. The tool and device 10 as shown in FIG. 22F are then ready for use. The distal end containing device 10/expandable member 10*em* is inserted into the abdominal cavity, such as by delivery though a percutaneous or laparoscopic opening, for example. One in the vicinity of the intended implantation site (surgical target location), outer sheath 696*o* can be retracted relative to inner sheath 696*i*. As outer sheath 696*o* is retracted to the extent that bend 696*b* is no longer covered, inner sheath 696*i* returns to its unbiased, bent configuration, as illustrated in FIG. 22G. At this time, the distal end portion of expandable member 10*em*, and typically at least one attachment tab 682 (or attachment flange 682F, as shown in FIG. 22G) are presented and the distal end portion of expandable member 10*em* can be sutured, stapled, tacked, etc. to an internal structure in the abdominal cavity. By incrementally retracting inner sheath 696*i*, incremental portions of expandable member 10*em* can be extracted (e.g., unrolled and/or unfolded) with fixation of these portions being accomplished between the incremental extraction steps. Alternatively, expandable member 10*em* can be nearly fully extracted or fully extracted after just the first fixation of the distal end portion has been accomplished, or even without any anchoring of tabs 682/682F if the surgeon desired to just grasp the distal end portion of expandable member 10*em* with graspers or other temporary fixation tool as inner sheath 696*i* is retracted. FIG. 22H illustrates the expandable member when is has been almost completely extracted.

FIGS. 22I-22K illustrate operation of another delivery tool for use in delivering and facilitation of anchoring of device 10 in the abdominal cavity. This tool also advantageously provides the ability to deliver device 10 by a percutaneous procedure or laparoscopic procedure. Of course, this tool can also be used in open procedures. The tool in this embodiment includes an introducer that comprises a rigid, closed-ended (at the proximal end) sheath or tube 696 that houses the expandable member 10*em* during delivery thereof, as illustrated in FIG. 22K. An attachment tab 682 or other distal portion of expandable member 10*em* may be left extending distally from sheath 696 after expandable member 10*em* is loaded into sheath 696 for delivery thereof, as shown in FIG. 22K. This facilitates grasping of the distal portion and/or anchoring thereof to a structure in the abdominal cavity, as described below.

Expandable member 10*em*, in a non-expanded or deflated state is substantially flattened and then rolled from both side edges (FIG. 22I) toward a central axis, to form what is referred to as a "tongue-roll" configuration, as illustrated in FIG. 22J. By rolling up expandable member 10*em* from both side edges, this avoid twisting of lumen 12 which is located substantially in alignment with the central axis of expandable member 10*em* in this case. The tongue-rolled expandable member 10*em* is then inserted into the open distal end of introducer 696 and slid into the sheath 696 of the introducer until configured as shown in FIG. 22K. In the example shown, lumen 12 is short and does not extend much (if at all) past the edge of expandable member 10*em*. In cases where lumen 12 is longer, lumen 12 can extend alongside the tongue-rolled expandable member 10*em* to extend out of the distal end opening of sheath 696 and then bend back to run along the length of introducer sheath 696 so that a proximal end of lumen 12 extends out of the body with the proximal end of sheath 696 as expandable member is placed in the abdominal cavity.

Since the introducer comprises a rigid sheath 696, it can be used to perform blunt dissection while delivering expandable member 10*em* to the intended surgical target location in the abdominal cavity. Once the distal end portion of the introducer/sheath 696 that contains expandable member 10*em* has been located in the vicinity of the surgical target location, the attachment tab 682 (or flange 682F) that extends distally of the distal end of sheath 696 can be sutured, stapled, tacked, etc. to an internal structure in the abdominal cavity. By incrementally retracting sheath 696, incremental portions of expandable member 10*em* can be extracted (e.g., and unrolled) with fixation of these portions being accomplished between the incremental extraction steps. Alternatively, expandable member 10*em* can be nearly fully extracted or fully extracted after just the first fixation of the distal end portion has been accomplished, or even without any anchoring of tabs 682/682F if the surgeon desires to just grasp the distal end portion of expandable member 10*em* with graspers or other temporary fixation tool as sheath 696 is retracted.

Figure 22L:
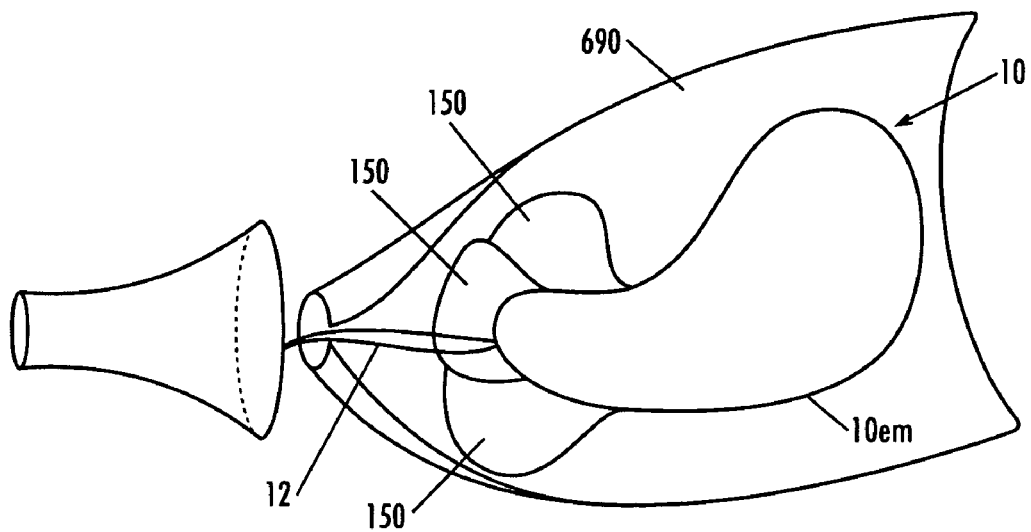
FIGS. 22L-22M illustrate another variation of an arrangement for compacting a device and maintaining it the compact configuration for delivery into the abdominal cavity.
Figure 22M:
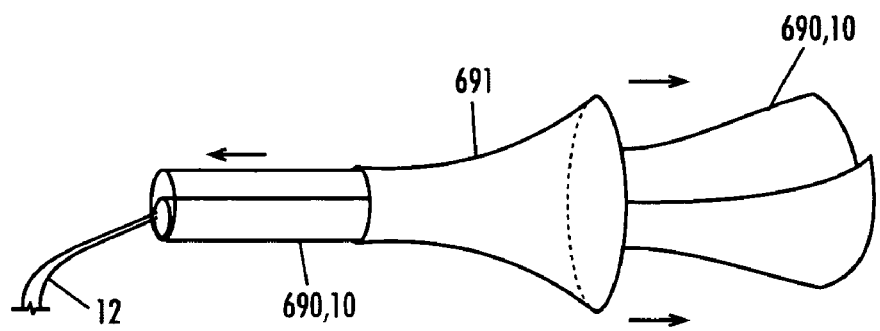

FIGS. 22L-22M illustrate another variation of an arrangement for compacting device 10 and maintaining it the compact configuration for delivery into the abdominal cavity. In another embodiment, device 10 is compacted and maintained in a compact configuration by insertion within a sheath 690 as illustrated in FIG. 22A. Sheath 690 does not completely encircle expandable member 10*em*, but includes a slit through which a rail or channel connected to expandable member 10*em*, and which is to be connected to frame 600, is exposed. Device 10 can be compacted into the compressed configuration by rolling it in flexible sheath 690. In this case, sheath 690 can completely surround device 10 when the device is to be anchored using tabs 150. Once rolled up, such as by tongue-rolling or other rolling technique, the sheath 690 and device 10 assembly can be further compacted/compressed by drawing it through a funnel compactor 691 as illustrated in FIG. 22M, by pushing and/or pulling assembly 690,10 to the left in FIG. 22M and/or pushing or pulling compactor funnel 691 to the right in FIG. 22M. The small opening of the funnel compactor 691 can be made to have an inside diameter of a maximum, predetermined size acceptable for delivery of the assembly through a small opening and into the abdominal cavity.

Figure 22N:
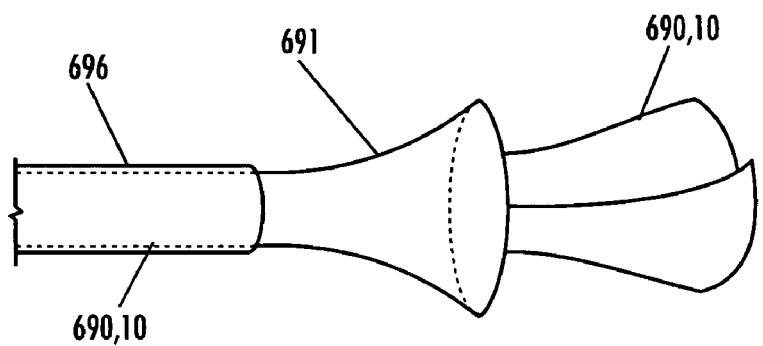
FIG. 22N illustrates an optional use of a sheath with the arrangement previously shown in FIGS. 22L-22M.

Further optionally, an additional sheath or inserter 696 can be mounted over the small end of compactor funnel 691, as illustrated in FIG. 22N, so that the further compressed assembly 690,10 is loaded into this additional sheath or inserter 696. The introducer or sheath 696 can then be inserted through a small opening in the skin of the patient and into the abdominal cavity, where assembly 690,10 can be extracted according to any of the techniques described above. Further alternatively, sheath 696 may be open ended at both ends, and a pusher rod can be pushed through the proximal end opening of sheath or introducer 696 to drive the assembly 690,10 out of the distal end opening. In any of these arrangements, once the assembly 690,10 has been extracted, it can be unrolled, and device 10 can be positioned and anchored according to any of the techniques described herein. Sheath 690 is removed from the abdominal cavity and from the patient.

FIG. 22O shows a further alternative arrangement, in which sheath 690 and device 10 after rolling and compressing according to the techniques described above with regard to FIGS. 22L-22M, is back-loaded on a steerable, flexible endoscope 356. Alternatively, sheath 690 and device 10 can be wrapped and compressed around steerable, flexible endoscope 356 to backload the assembly 690,10 thereon, without the use of compactor funnel 691. According to either of these techniques, after making a small incision 223 in the patient, the endoscope 356 is advanced through the opening and into the abdominal cavity. The endoscope 356 can be steered during this process to advance the distal tip 790 thereof to a desired location in the abdominal cavity where it is desired to place device 10. Also, full insufflation of the abdominal cavity is not needed in order to deliver device 10 by this technique. Once the distal tip 796 of endoscope 356 has been steered and advanced to a desired location in the abdominal cavity, assembly 690,10 can then be delivered over the shaft of endoscope 356 and ejected off of the distal end of endoscope. Device 10 may be delivered over an anchoring frame 600 using this technique, and/or ejected into the abdominal cavity for subsequent positioning and anchoring by tabs 150.

Optionally, as the endoscope 356 assembly is being advanced, impulse puffs of pressurized gas can be intermittently applied through the distal end of endoscope 356 (or with an additional conduit that delivers these impulses to the location of (or just distal to) the distal end of endoscope 356 to help open a pathway along which it is desired to steer the endoscope 356. Further alternatively, device 10 can be compacted and back-loaded around endoscope 356 without sheath 690.

Further alternatively and optionally, endoscope 356 may be provided with an expandable distal tip/lens 790e that is expandable distally away from and around the distal end 790 of endoscope through which viewing is performed, as illustrated in FIGS. 22P-22Q. This expandable tip 790 can be expanded to displace tissue away from viewing end 790 to provide a clear view so the that operator can more easily steer the distal end to a desired location. This arrangement does not require the use of "puffs" or impulses of pressurized insufflation gas, or any insufflation whatsoever. FIG. 22Q illustrates expandable tip/lens as an inflatable balloon which is shown in an inflated/expanded configuration. FIG. 22R shows a variant of the tip/lens 790e in an expanded configuration, in which balloon 790 is further reinforced by deployable wires 791 that can be extended distally (as shown) and retracted proximally of the distal end 790 when it is desired to have the tip 790 in a non-expanded (undeployed) configuration. Wires 791 can be biased toward the expanded configuration shown, so that they expand the balloon 790e without the need to inflation gas or liquid into the balloon 790e. Alternatively, balloon 70e can be expanded by both gas or liquid (typically liquid) and the mechanical forces applied by expanding wires 791.

FIG. 22S illustrates an alternative to use of a flexible, steerable endoscope 356 inserted and used as a guide rail for delivery of device 10 (as well as, optionally, other devices or instruments) thereover and into the abdominal cavity, as described above with regard to FIG. 22O. In FIG. 22S, a flexible wire 502e that is similar in construction to guidewire 502, only slightly larger in cross-sectional diameter, includes one or more optical fibers extending the length thereof to facilitate viewing through the distal end portion 502de of wire 502e. Accordingly, wire 502e can be inserted in the same manner as guidewire 502 and used for the same purposes. However, visualization can be performed as the flexible wire 502e is being inserted and advanced, for visual verification that the distal end portion is being delivered to an intended location in the abdominal cavity.

Optionally, wire 502e may include an expandable tip, such as an inflatable balloon, like 70e describe above with regard to FIG. 22Q. This balloon can be expanded to provided an enlarged visual field. By foregoing the steering mechanism of a steerable endoscope 356 and guiding the wire 502e, assisted by visualization, into the abdominal cavity in a manner as described with regard to insertion of guidewire 502, this allows 502e to have a significantly smaller cross sectional area than a steerable endoscope 356.

Figure 23:
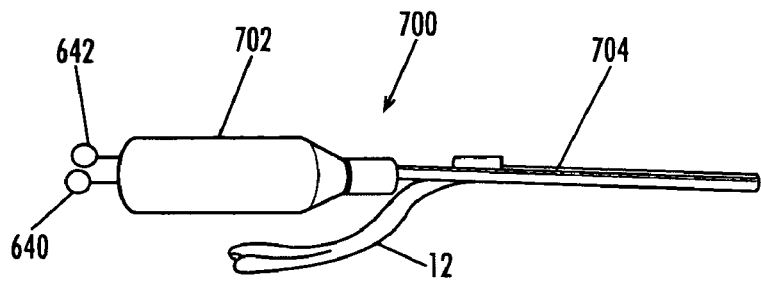
FIG. 23 illustrates a device deployment tool that can be used to deploy a device lover an anchoring frame.

FIG. 23 illustrates a device deployment tool 700 that can be used to deploy device 10 over anchoring frame 600. Tool 700 includes a handle 702 for manual operation by a user (e.g., surgeon) and an elongated shaft 704 extending distally therefrom. Shaft 704 in included a groove or rail that substantially matches a groove or rail of frame 600 over which device 10 is to be mounted. Accordingly, device 10 slides over the groove or rail of tool 700 and can be delivered over guidewire or rod 502 into alignment with the groove or rail of frame 600 where device 10 can then be pushed off of shaft (rail or groove) 704 and over the rail or groove of frame 600 to anchor the expandable member 10em of the device 10 to frame 600. One or more lumens may be provided through shaft 704 for delivery of irrigating fluids (or other substances) and for application of suction to the distal end of shaft 704, via ports 640 and 642, respectively.

Figure 24A:
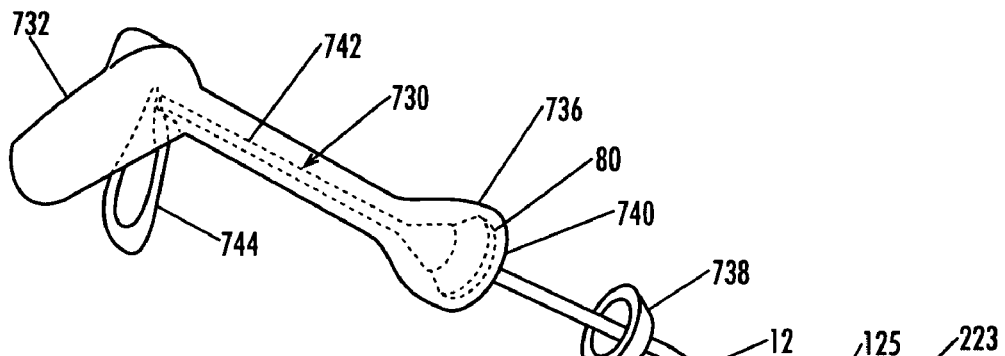
FIGS. 24A-24C illustrate an access member attachment tool and use of the tool for rapid attachment of an access member to a patient.
Figure 24B:
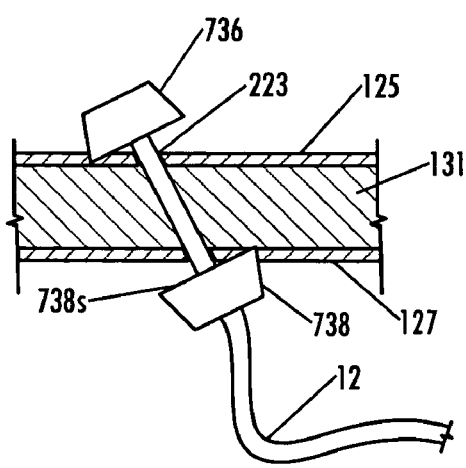
Figure 24C:
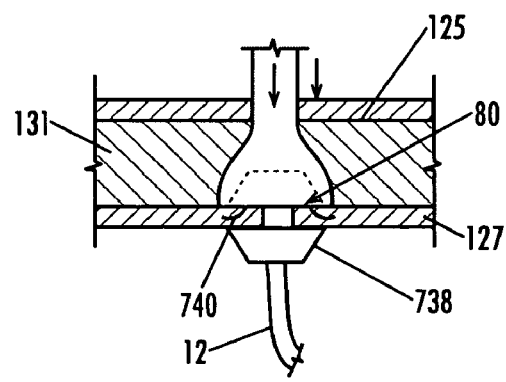

FIGS. 24A-24C illustrate an access member attachment tool 730 and use of tool 730 for rapid attachment of access member 80 to the patient 1. Access member attachment tool 730 includes a handle 732 for handling and control by a user, and a working end 736 at a distal end portion thereof. According to this approach, an anvil 738 is slid over conduit(s) 12 prior to connecting access member 80 to the distal end(s) of conduit(s) 12. Working end 736 is configured to received access member 80 therein, e.g., working end may include a socket shaped and dimensioned to receive access member 80 therein and to maintain the orientation of access member so as to control it during attachment to the patient.

Anvil 738 is first delivered by manipulating (e.g., twisting and pushing) it through opening 223 and through the opening in the abdominal muscle 127, as illustrated in FIG. 24B. Distal end 736 of tool 730 may be inserted into the fat layer 131 either before or after manipulating anvil 738 into the desired orientation for use. Once anvil has been inserted through the opening in the abdominal muscle and manipulated to orient the anvil surface 738s in contact with the abdominal muscle wall 127, tool 730 is used to drive access member 80 against anvil surface 738s as illustrated in FIG. 24C. An inner shaft of tool 730 clamps or otherwise engages tubing 12 and/or anvil 738 and draws them toward portion 736 when actuator 744 is actuated. Access member 80 includes penetrating members 740 that extend distally from the contact surface of access member that contacts the abdominal muscle 127 as access member is driven against anvil 738. As access member 80 is driven against anvil surface 738s, penetrating members 740 are driven against the anvil surface 738s and thereby bent over, as illustrated in FIG. 24C, thereby anchoring access member to the abdominal muscle wall. Driving of access member 80 against anvil 738 may be performed by simply pushing with handle 732. Additionally, or alternatively, and further optionally, actuator 744 may be operably configured to deploy penetrating members distally from the contact surface of access member 80 upon actuation of the actuator.

Alternative mechanisms may be used for attachment of access member 80 to the patient 1. For example, FIG. 25A shows use of hook and loop type fasteners 746a, 746b or other interlocking mechanism used for a quick connect mechanism to attach access member 80 to the abdominal muscle 127 of the patient 1. In the example shown, a ring 747 that contains or is made of one of either hook or loop material (746a or 746b, respectively) is stapled or sutured to the abdominal muscle layer 127 to surround the opening in the abdominal muscle and conduit(s) 12. The contact surface of access member is provided with the other of either the hook or loop material, respectively, such that when access member is pushed against ring 747, the interlocking mechanism 746 (in this example, hook and loop materials) interlock, thereby attaching access member 80 to the patient.

In FIG. 25B, ring 747 is provided with one or more magnets 748b having polarity on the surface facing access member 80 that is opposite the polarity of the surfaces of magnets 748a facing ring 747. Ring 747 may be provided with anchors 749 and/or may be sutured, or adhered to abdominal muscle layer 127. By pressing access member 80 against the anchored ring 747, connection mechanism 748 connects access member 80 to the patient 1 via the attraction forces of magnets 748a, 748b.

FIGS. 25C and 25D illustrate undeployed and deployed configurations, respectively, of an access member having deployable anchors 750. Anchors 750 are extendable, for example, by collapsing external tubing using compression force. By retracting the inner tubing or shaft that is axially positioned inside anchors 750 with a distal end connected thereto, this drives anchors 750 into the extended configuration shown in FIG. 25D. That is, the functionality is like a moly-bolt. Anchors 750 include arms that are hingedly connected and which bend to expand outwardly, as they are compressed by retracting the internal tube.

FIGS. 25E and 25F illustrate undeployed and deployed configurations, respectively, of an access member having a spring member 752 that functions to anchor access member 80 to the patient 1. In the undeployed configuration of FIG. 25E, spring member 752 is wound to as to assume a relatively small outside diameter. This wound configuration can be maintained by a safety lock 754 provided in access member that is actuatable between a locked and an unlocked position. After inserting access member 80 into position with respect to the abdominal muscle wall 127, so that spring member 752 passes through the opening in the abdominal muscle and is located inside the abdominal muscle wall 127 as illustrated in FIG. 25E, safety lock 754 is released, so that spring member 752 unwinds to its deployed configuration, where it has a much larger outside diameter that is too large to pass back through the opening in the abdominal muscle 127, see FIG. 25F.

Figure 25G:
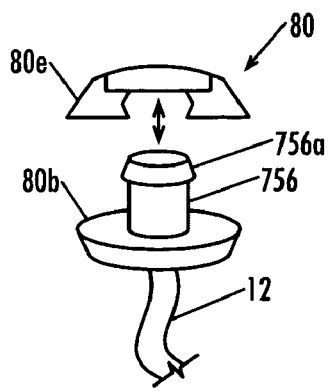
FIGS. 25G-25H show an embodiment of an access member that is connectable via a snap fit that provides a clamping action between a base and an external portion.
Figure 25H:
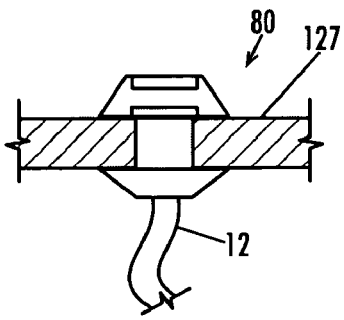

FIGS. 25G-25H show an embodiment of access member that is connectable via a snap fit that provides a clamping action between base 80b and external portion 80e. Base 80b is provided with a spacer 756 having a length about the same as the thickness of the abdominal muscle 127. The top portion of tubular spacer is provided with a lip 756a that has a outside diameter slightly greater than the inside diameter or the opening 758a to socket 758. Base 80b inserted through the opening in the abdominal muscle and oriented so that contact surface 80sb aligns with the inner wall of abdominal muscle 127 and spacer 756 extends out through the opening in the abdominal wall 127. External portion 80e is then pressed against base 80b with tubular spacer 756 aligned with socket 758, so that lip 756a snaps through opening 758a and is retained within socket 758, thereby connecting access member 80 to the abdominal wall 127.

Figure 25J:
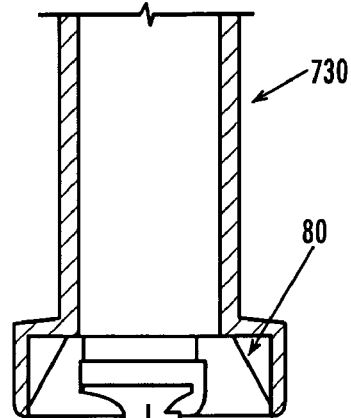
FIG. 25J illustrates a tool for deploying an engagement member into the interlock of FIG. 25I.
Figure 25I:
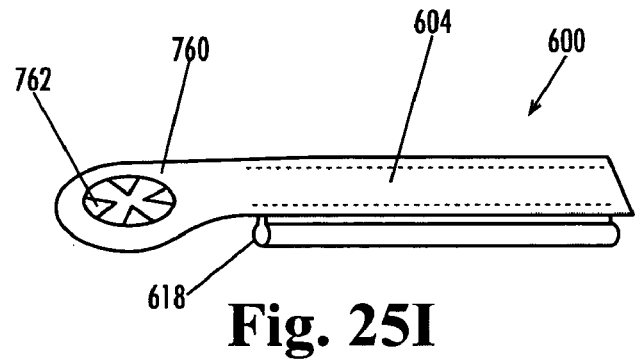
FIG. 25I illustrates an anchoring frame provided with an interlock on a proximal end portion thereof.

Anchoring frame 600 may be provided with an interlock 760 on a proximal end portion thereof, as shown in FIG. 25I. In this case, anchoring frame 600 is provided with sufficient length to extend to the location against the abdominal wall 127 where it is desired to attach access member 80. Interlock 760 may be provided with resiliently deflectable teeth 762 that deform as engagement members 764 (FIG. 25J) located on access member 80 are inserted therethrough. Engagement members may have threading or be otherwise formed to have alternating large and small diameter portions, so that the large diameter portions deflect teeth 762, while the small diameter portions allow teeth 762 to rebound thereagainst to form a lock relative to the adjacent large diameter portions.

Figure 25K:
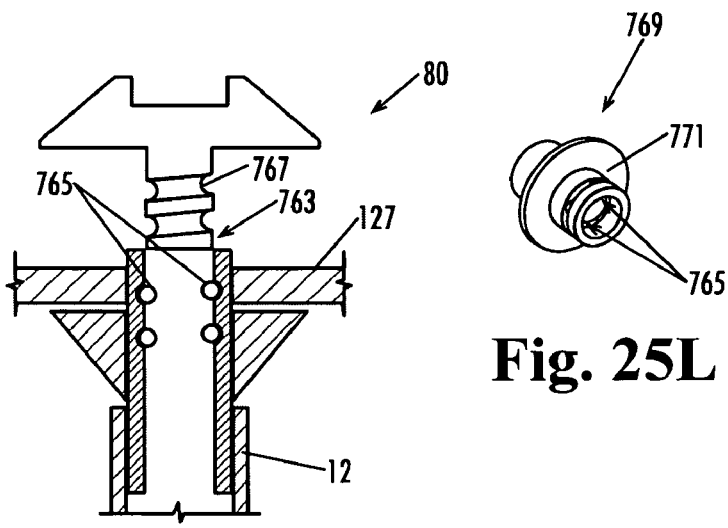
FIG. 25K shows an embodiment of access member that is connectable via an automatic engagement mechanism that functions like a chuck for a pneumatic tool.

FIG. 25K shows an embodiment of access member 80 that is connectable via an automatic engagement mechanism 763 that functions like a chuck for a pneumatic tool. That is, the base portion that is inserted intra-abdominally includes a socket portion having one or more sets of spring-loaded bearings or detents 765, and the external portion includes a tubular shaft to be inserted into the socket portion and which has one or more annular recesses 767 configured to mate with detents 765. Thus, when the tubular shaft of the external portion is inserted into the socket portion, the outer wall of the tubular shaft depresses detents 765 allowing the tubular shaft to be further inserted. When aligned with annular recesses 767, detents resiliently return to their orientations shown in FIG. 25K and are received in recess(es) 767, thereby locking the two components of access member 80 together on opposite sides of the abdominal muscle 127.

Figure 25L:
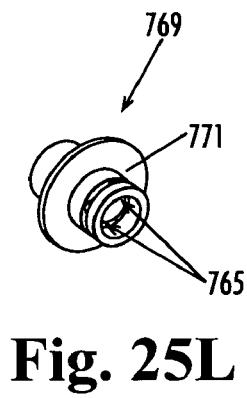
FIG. 25L-25M show another variation of an air hose-like type of quick connector.
Figure 25M:
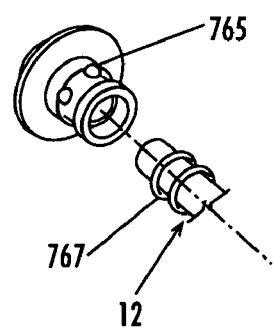

FIGS. 25L-25M show another variation of an air hose type of quick connector. In either this embodiment or the embodiment of FIG. 25K, the male and female connector parts can be reversed relative to the positions shown. In this embodiment, connector 769 may be provided either as a part of access member 80, or simply as a connector for anchoring device 10 to the abdominal wall 127 and/or to provide a connection to conduit 12 that extends externally of the abdominal wall. Balls 765 and groove 767 function in the same way as described above with regard to FIG. 25K. However, in this instance, connector 769 includes a locking sleeve 771 that slides over balls 765 to maintain them in the locked configuration (FIG. 25L). Locking sleeve 771 is retractable, as shown in FIG. 25M to allow balls 765 to deflect radially outwardly to allow insertion of the male portion of the connector 769 into the female portion and then slide sleeve 771 back over balls 765 to lock them in position in groove 767. Sleeve 771 may be spring biased toward the closed/locked position, wherein it can be manually retracted to the unlocked position.

As already noted, device 10 may be implanted by a variety of different methods, including percutaneous methods (examples of which have been described in detail above and which typically do not require pressurized insufflation of the entire abdominal cavity, or generalized anesthesia, and one or more steps may be performed without direct visualization), laparoscopic methods (which typically include pressurized insufflation of the entire abdominal cavity and the patient 1 under general anesthesia), min-laparoscopic methods and open methods. In addition to anchoring device 10 via anchoring frame 600, or alternative thereto, other anchoring features and/or techniques may be employed. Any of the various features and/or techniques described herein may be used together, or separately, unless it use of one feature or technique would clearly preclude use of another specifically disclosed feature and technique and they would therefore not be useable together.

Figure 26A:
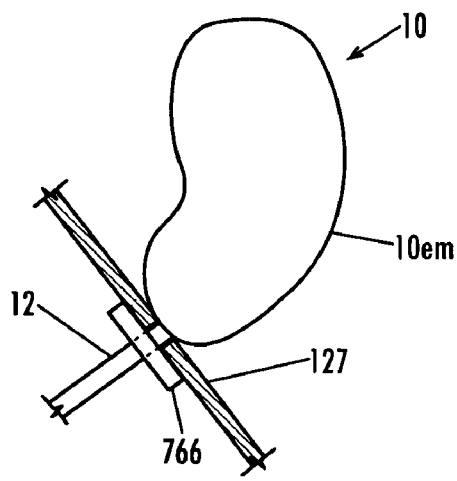
FIG. 26A illustrated a device being anchored wherein a conduit is actively employed in the anchoring.

One such method of anchoring involves anchoring device 10 to the abdominal wall 127 via tubing extending from device 10 and through the abdominal wall. For example, conduit 12 may be used to accomplish such anchoring, as illustrated in FIG. 26A. In examples where device 10 is implanted an expanded in the space along the diaphragm 116 as described above, it has been experienced, that, once expanded, expandable member 10em maintains its position quite well in superior-inferior directions with tendency to move being more likely laterally. By anchoring device 10e to the abdominal wall using tubing 12, this secures expandable member 10em from such lateral movements. Because device 10 is less likely to move superiorly or inferiorly, this type of anchoring may be sufficient in itself for implantation of device 10. An advantage of anchoring only by this technique is that no suturing or stapling inside the abdominal cavity is required. In FIG. 26A, a lock nut 766 is threaded over tubing 12 to secure expandable member 10em in contact with the inner abdominal wall 127. Lock nut 766 may include a contact surface covered with tissue ingrowth material such as Dacron, polyester, or other porous material designed to encourage tissue ingrowth or may be formed entirely of a tissue ingrowth material. Further optionally, access member 80 may be configured to function as an anchor to replace the lock nut, wherein access member 80 can be fixed by any of the features described herein. This method of anchoring assists in positioning device 10 and stabilizing it in its intended position.

Figure 26B:
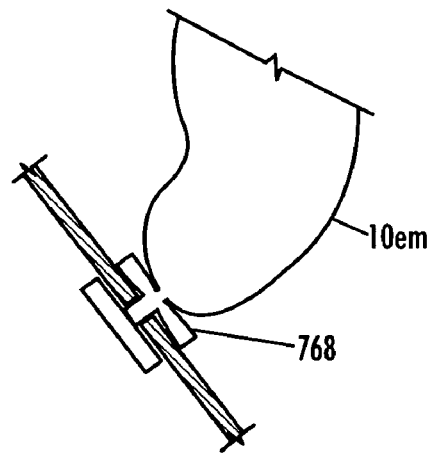
FIG. 26B illustrates tissue ingrowth-enhancing material provided at an interface between the expandable member and the inner wall of the abdominal muscle.

In addition or alternative to providing tissue ingrowth enhancing material on the external side of the abdominal muscle wall 127, tissue ingrowth enhancing material 768 may be provided at the interface between expandable member 10em and the inner wall of the abdominal muscle 127, as illustrated in FIG. 26B. For example, a disk of tissue ingrowth enhancing material 768 may be slid over conduit 12. Alternatively, one or more attachment tabs including tissue ingrowth enhancing material 768 may be fixed to device 10, such as expandable member 10em, as described in more detail below. Examples of tissue ingrowth-enhancing materials include, but are not limited to, expanded polytetrafluoroethylene (having an internodal distance typical of those materials used for vascular grafts); mesh materials made of polyester, polypropylene, or the like, typically with pores in the range of about 0.7 mm to about 1.5 mm or about 0.5 mm to about 1.2 mm; polyester having a maximum water permeability of about 1800 to about 4000 ml/cm$^2$/min; or felts made of expanded polytetrafluoroethylene or polyester having a maximum water permeability in the range of about 550 to about 3050 ml/cm$^2$/min.

Figure 26C:
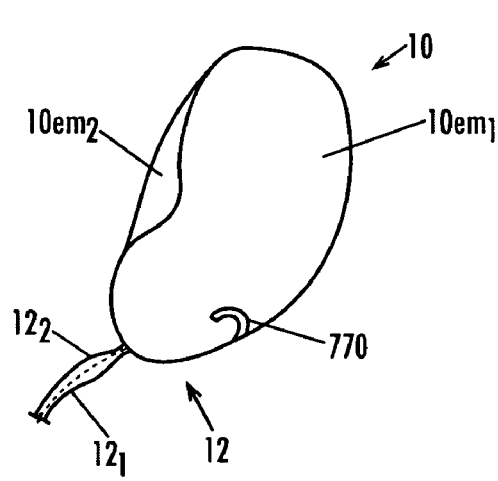
FIG. 26C illustrates an example of a device including a loop (similar to a belt loop).
Figure 26D:
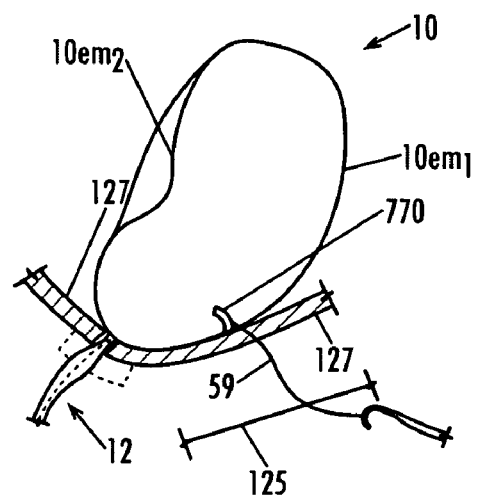
FIG. 26D illustrates positioning of a device by applying a traction force to the loop shown in FIG. 26C.
Figure 26E:
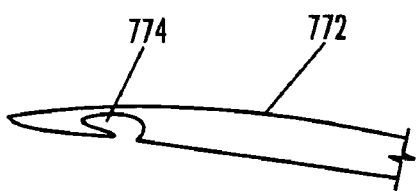
FIG. 26E illustrates a distal end portion of an elongated needle having a hooked slot.

In addition or alternative to anchoring device 10 against an intra-abdominal structure (e.g., abdominal muscle wall or other structure) using conduit 12, device 10 may be provided with a positioning member 770 that can be used to further position or relocate device 10 and assist in anchoring device 10 in such position or location. FIG. 26C illustrates an example of a device 10 including a loop (similar to a belt loop, and which may be made of Dacron-reinforced tubing, for example) shaped positioning member 270. When used in a laparoscopic procedure or other procedure using multiple ports through the patient's skin and into the abdominal cavity, device 10 can be inserted through a first port. A suture or tether 59 can be looped through positioning member 770 and tied off to form a looped suture or tether 59. Then a surgeon or assistant can access the suture or tether 59 via an incision adjacent the port through which the device 10 was inserted, to hook, grasp or otherwise capture suture or tether 59 and pull it out through the incision where access was made (FIG. 26D). For example, graspers, an elongated instrument having a hook at a distal end thereof, or other endoscopic instrument may be used to capture suture or tether 59 and pull it out of the opening though the patient's skin. This tension exerted on suture or tether 59 and pulling of the suture or tether 59 out of the patient draws device 10 toward the opening through which suture or tether is drawn, thereby drawing an inferior surface of expandable member 10em1 up against the abdominal wall 127 in this example. Alternatively, tension may be applied to the suture or tether 59 as it extends from the opening through which the device 10 was inserted, to draw attachment tab(s) 150 up against the abdominal wall for attaching tab(s) 150 thereto. For a percutaneous procedure where only a single port is provided for delivery and implantation of device 10 an additional puncture can be performed through the patient's skin and into the abdominal cavity, at a location where it is desired to draw suture or tether 59 through and to draw device 10 against an intra-abdominal structure. For example, an elongated needle 772 (FIG. 26E) having a hooked slot 774 may be used to pierce the patient's skin, access the abdominal cavity, and capture suture or tether 59 in hooked slot 774. Needle 772 can then be retracted out of the patient 1 to draw suture or tether 59 out of the patient to draw device 10 against a structure in the abdominal cavity to anchor it there.

Figure 26F:
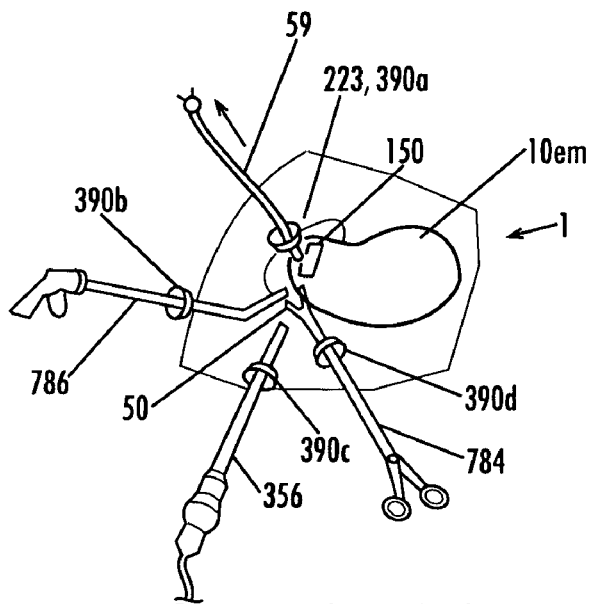
FIG. 26F illustrates a step of attaching an attachment tab to the abdominal wall, according to one embodiment using a laparoscopic procedure.

FIG. 26F illustrates a step of attaching attachment tab 150 to the abdominal wall 127, according to one embodiment using a laparoscopic procedure. In this case, tension is applied to tether/suture 59 as it extends through the opening 223/port 390a that was used to insert device 10 into the abdominal cavity. As tension is applied graspers 784 having been inserted through port 390d are used to manipulate attachment tab 150 to approximate it to the abdominal wall 150 for attachment thereto. Thus, tension may also be applied via the graspers 784. A laparoscopic stapler 786, inserted through port 390b is used to staple attachment tab(s) to the abdominal wall 127. Visualization of all operations can be provided via endoscope 356 inserted through port 390c. It is noted that invention is not limited to the locations and number of ports shown, as the locations and numbers may vary. For example, an additional opening may be provided to insert a liver retractor for retraction of the liver during the procedure, such as was described in application Ser. No. 11/407,701 with regard to FIG. 67. Also, the arrangement of the instruments shown may vary depending on need for the steps being performed. As one non-limiting example, stapler 786 may be inserted through port 390c while endoscope 356 is inserted through port 390b. Further alternatively, suture/tether may be drawn through another port, as already noted above. This attachment process can be carried out in addition to fixing device 10 to an anchoring frame 600 according to any of the techniques described above, or alternative to it, where a frame 600 is not used.

Figure 26G:
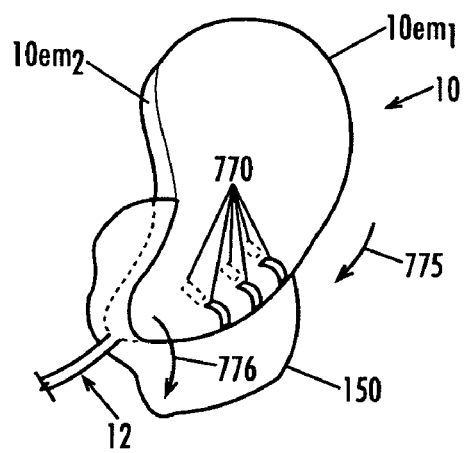
FIG. 26G shows an example of a device having three positioning loops longitudinally spaced along an expandable member.

Further optionally, device 10 may be provided with a plurality of positioning members 770 such as positioning loops, for example, spaced longitudinally along device 10. Two, three, four or more such members 770 may be provided along expandable member 10em, for example. FIG. 26G shows an example of device 10 having three positioning loops 770 longitudinally spaced along expandable member 10em$_1$. By providing multiple positioning members 770 that are longitudinally spaced, the same device can be used for patients having different anatomies that may have different positioning requirements for the expanded device 10 and or may have different volume requirements of a spaced to be filled by device 10. Depending upon the loop 770 selected by the surgeon to be used to position and anchor device 10, device 10 can be anchored, for example to the abdominal wall 127, with more or less of the surface of expandable member 10em$_1$ drawn up against the abdominal wall 127. This in turn varies the angulation and positioning of device 10 in the abdominal cavity. Typically, the surgeon will have an idea of which positioning member 770 is to be used for the particular patient that device 10 is being implanted in, for example, after studying the anatomy of the patient's abdominal cavity and structures therein, as provided by prior MRI or CT scanning for example. In such case, only one positioning member 770 will have a suture or tether 59 looped there around to be used as described above. Alternatively, more than one, up to all of the positioning members 770 may have a suture or tether 59 looped there around so that the surgeon can try alternative positioning with more that one positioning member, using one at a time successively and observing (such as by fluoroscopy, for example) the relative positions of device 10 resulting from each use of a different positing member 770. The "best fit" can then be selected and used to complete the anchoring of the device. Prior to that however, the tethers or sutures 59 that are not chosen for final use in positioning are cut and removed through the opening that will be used to draw the selected tether or suture therethrough for positioning. Thus, these cut, non-selected tethers or sutures 59 are removed from the surgical site prior to use of the selected suture or tether 59 to perform attachment/anchoring of device 10.

Figure 26H:
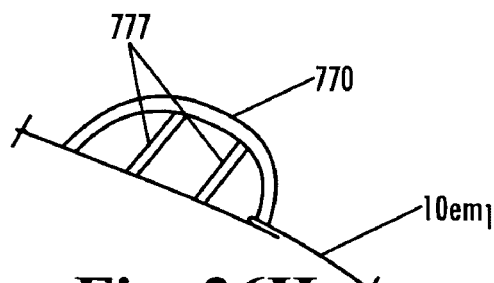
FIG. 26H illustrates a segmented positioning member having multiple positioning features or channels within a loop.

Still further, positioning members 770 may be segmented 777 to provide multiple positioning features or channels 778 within a loop 770 (as illustrated in FIG. 26H) or multiple positioning members 770 may be spaced in a direction perpendicular to the longitudinal spacing (as indicated in phantom lines in FIG. 26G) to provide further positioning control choices for orienting device 10 angularly about a longitudinal axis, as indicated by the direction of orientation adjustment 776 in FIG. 26G. The choice of positioning member 770 among the longitudinally spaced members 770 varies the positioning about a transverse axis of device 10 (i.e., axis passing into the page and through the middle of expandable member $10em_1$.

To facilitate anchoring of device 10 after positioning by positioning members, device 10 may be provided with one or more attachment tabs 150. FIG. 26F illustrates a single continuous attachment tab 150 that extends from expandable member $10em_1$ about a circumferentially extending portion of the surface of the inferior portion of expandable member $10em_1$. Attachment tab 150 may be bonded to the surface of expandable $10em_1$, such as with silicone dip layer, for example, or using room temperature vulcanizing silicone adhesive. Alternatively, unvulcanized silicone sheeting can be placed between tab 150 and expandable member 10em and these layers can be vulcanized together using a heated press. Further alternatively, if the materials are made of polyurethane, a solvent bond can be made using a slurry mixture of polyurethane to bond a polyurethane tab 150 to a polyurethane expandable member 10em.

Alternatively, multiple attachment tabs 150 can be placed at locations around expandable member 10em to extend from and substantially cover areas covered by a larger single attachment tab 150. FIG. 27A illustrates one such example of a device 10 with multiple attachment tabs 150, in this case, having three attachment tabs 150. By providing multiple attachment tabs, the tabs are more easily able to conform to the structure that they are being attached to, particularly if there is some curvature or other surface shape other than planar in the structure. That is, tabs 150 can be overlapped to reduce the overall coverage of the structure to be attached to and this increases the convexity of the attachment surfaces formed by tabs 150 to better conform to a concave shape of an internal surface of the structure to be attached to (e.g., abdominal wall), or otherwise change to a surface shape to be conformed to, or spread apart to increase the convexity of the attachment surfaces formed by tabs 150, or otherwise change to a surface shape to be conformed to. The overlapping prevents folds or wrinkles that would otherwise occur with a single tab 150 such as like that in FIG. 26F, and the spreading would just not be possible with a single tab like that shown in FIG. 26F. The use of attachment tab(s) 150 also gives the surgeon the option to not use access member 80 and/or conduit 12 to perform an anchoring function. This allows access member 80 to be placed further away from the ribs, potentially offering the patient less discomfort, and also allows conduit 12 to be placed so that it is not under tension to perform an anchoring function, thereby lessening the mechanical requirements for conduit 12.

Figure 26I:
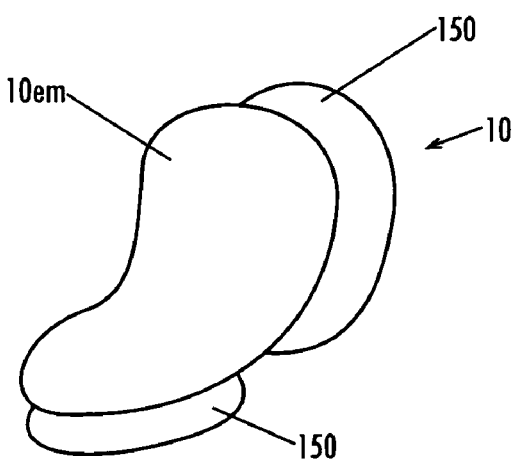
FIG. 26I shows a device having an attachment tab extending from a superior portion of an expandable member and another attachment tab extending from an inferior portion of the expandable member.

Attachment tabs 150, although typically located to extend from the inferior portion of expandable member 10em, need not be so located, but can be placed to extend from any locations on device 10 or expandable member 10em. As one example, FIG. 26I shows a device 10 having an attachment tab 150 extending from a superior portion of expandable member 10em and another attachment tab 150 extending from an inferior portion of expandable member 10em. Tab 150 will typically be provided with a tissue ingrowth material, such as any of the examples described above. In at least one embodiment, polyester-reinforced silicone sheeting forms the base structure of tab 150 and this is the material that is bonded onto a silicone expandable member 10em. The tissue ingrowth-enhancing members or patches 152 are then separately bonded onto the base structure. In at least one alternative embodiment, the base structure is made of polyester-reinforced polyurethane sheet, while the tissue ingrowth-enhancing member s or patches 152 can be made of any of the same materials already described above. Tabs 150 can withstand a tensile force of at least about three to five pounds, on a suture looped therethrough, without tearing of the base structure or the suture ripping out of the base structure.

Tabs can be attached to an intra-abdominal structure by stapling, tacking, suturing or the like. FIG. 28 illustrates one configuration of attachment tab 150, wherein the main body portion 150a includes a tissue ingrowth-enhancing material. However, a margin portion 150b is provided that connects to expandable member 10em that is not tissue ingrowth promoting. Accordingly, after anchoring device 10 via attachment tab 150 to a tissue structure within the abdominal cavity, the anchoring may be further fortified after a healing period by the ingrowth of tissue into main body 150a. However, since no tissue ingrowth occurs at margin 150b, device 10 can be more easily removed, if necessary, by cutting through the margin material 150b, thereby releasing device 10 from the anchored main body portion 150a. Further advantageously, margin portion 150b can be made of clear material so as to also function as a "window" so that the surgeon can view through it while performing the attachment of main body 150a to ensure that no bowel or other tissue not meant to be anchored to, exists between attachment tab 150 and the tissue intended to be anchored to, at the time of anchoring. For example, margin portion 150b may be made of silicone or other transparent material that is biocompatible and has sufficient mechanical strength to maintain the attachment/anchoring function.

FIG. 27B illustrates an example of a device having three attachment tabs 150 extending from the inferior portion of expandable member 10em, but where the tabs 150 are interjoined by margin portions at the side of the main bodies 150. The margin portions are separate to allow tabs 150 to be overlapped. Additionally, margins 150b completely surround the main body portions 150a in this embodiment. Potential suturing (or stapling, tacking, or the like) locations are indicated by the circles 150s shown on each of the main body portions 150a. The circular structure shown centrally located between the tabs 150 is another tab that may include tissue ingrowth enhancing material and/or the base structure material of tabs 150. A positioning loop may be attached to the center of the circle or pass therethrough and be bonded beneath the circle, and used in a manner as described in application Ser. No. 11/716,986, e.g., see FIGS. 22 and 23 and descriptions thereof). Alternatively or additionally, this circular structure may be a grasping feature for the surgeon to manipulate the expandable member 10em during the implantation process. In this case, the circular patch is bonded to the expandable member only over a central portion thereof, with a free edge or border that is not bonded, so that it can be grasped by graspers or other instrumentation. Backing structure 10ds may be made, for example, of a reinforced silicone sheet to help distribute the forces generated on attachment tabs anchored to the intra-abdominal structure, over a large area of the expandable member 10em. The backing structure 10*ds* may be made of multiple layers of reinforced silicone with non-reinforced silicone sheeting at the margins to provide an interface with expandable member 10*em* that substantially avoids generation of stress concentrations. The backing structure 10*ds* also provides structural support to expandable member 10*em* (e.g., to help prevent kinking) and helps define and maintain the expanded shape of expandable member 10*em* in the expanded configuration. The substantially oval-shaped patch above the circular one is also a grasping feature.

FIG. 27C schematically illustrates various features that may be provided for attachment of device 10 within the abdominal cavity, any of which may be used individually, or in any combination with any of the other features disclosed. Any individual use or combination of these features may also be used in addition to anchoring with anchoring frame 600. "Active attachment" features or methods includes those that involve mechanical or chemical attachment of a portion of the device to the patient, including, but not limited to, sutures, tacks, staples, adhesives, etc. "Passive attachment" features or method refer to configuring a surface to enhance tissue ingrowth therein or to encourage encapsulation, for example. Thus, all or a portion of expandable member 10*em* (and/or other component of device 10) may be provided with a roughened or "bumpy" surface 788, as such surfaces have been shown to encourage encapsulation of an implant. Also, porous surfaces 782 may be provided on any portion of device 10 that is desired to be anchored, to encourage tissue ingrowth. Thus, for example, attachment tab 150 can be used solely as a passive attachment feature when it is not actively stapled, tacked or sutured to the abdominal wall, but is merely placed in apposition thereto, and includes a porous portion 782 that allows tissue to grow into it. Alternatively, attachment tab could be completely nonporous, such as made of silicone, and attached only actively, such as by stapling. Further alternatively, attachment tab 150 may function for both active and passive attachment when it is stapled, tacked, sutured or adhered to an intra-abdominal structure and also includes a porous portion that encourages tissue ingrowth. Further, any of the other components may include a tissue ingrowth surface on a part or all of such component to provide passive attachment. For passive attachment, a period of about three to about six weeks is generally sufficient to anchor a tissue ingrowth surface of the type described herein, with ingrown tissue. In one experiment a one square inch surface of such material, after three weeks implanted in a dog was found to hold eight pounds of force. The omentum may also be actively attached to device 10 as serve as a buffer between device 10 and other organs in the abdomen to reduce irritation.

Optionally, in order to assist the surgeon in properly orienting attachment tab(s) 150 for attachment to the intended intra-abdominal structure, attachment tab(s) may be provided with one or more structural members 152 (FIG. 29A) that are deformable, so that attachment tabs 150 can be compacted to a compact configuration for delivery of device percutaneously or laparoscopically, but which resiliently return to their non-compacted shapes when a compacting force is no longer applied to attachment tabs 150. For example, structural member 152 may be a rib or sheet of shape memory material, such as nickel-titanium alloy or shape memory plastic, or may be made of spring steel (e.g., stainless steel). Alternatively, attachment tabs 150 may be inflatable, so that they can be expanded to a preshaped and predetermined orientation to facilitate the surgeon's placement of the attachment tabs against the tissue to be anchored to, and anchoring the tabs 150 to the tissue. Inflatable tabs 150 can have attachment features such as flanges at the borders thereof that are not inflatable so that sutures, staples, tacks, etc, can be passed therethrough to anchor the tabs 150 without deflating them. These inflatable tabs 150 may also include tissue ingrowth enhancing materials on portions thereof to encourage long term, permanent attachment of the tabs when tissue grows into this material. If multiple attachment tabs 150 are provided, as in FIG. 29B, a single conduit 153 may be provided to inflate/expand the attachment tabs 150, or multiple conduits may be provided. For example, a conduit 153 may be provided for the inferiorly located tabs 150, another conduit may feed the intermediately located tabs 153 and a third conduit may connect to the superiorly placed tab 150. Further alternatively, each attachment tab 150 may be provided with a dedicated conduit 153 in fluid communication therewith.

Figure 29E:
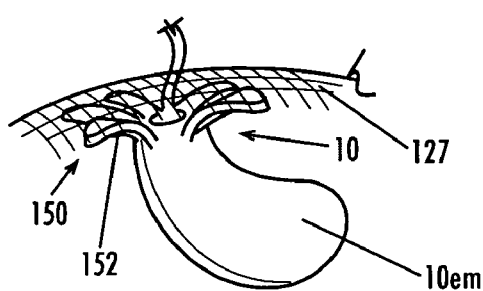

FIGS. 29C-29E illustrate another variation of a self-expanding attachment tab 150. In this case, structural member 152 is a self-expanding wire frame configured to conform the attachment tab(s) to the intra-abdominal structure that attachment tab(s) 150 is/are intended to be anchored to. FIG. 29C illustrates attachment tab 150 in the self-expanded configuration, wherein wire-frame 152 is biased toward this configuration. Wire frame 152 may be made of spring steel (e.g., stainless steel), nickel-titanium alloy, or shape-memory polymer, for example. The self-expanding wire frame 152 may be sandwiched between layers of, or embedded in the material of the attachment tab(s), for example Dacron-reinforced silicone.

FIG. 29D illustrates attachment tab 150 in a compressed configuration in preparation for loading into a sheath and/or insertion of device through a small opening in the patient 1. Wire frame 152 collapses into the shape shown under compressive forces applied radially inwardly on tab 150. FIG. 29E illustrates device 10 having been inserted into the abdominal cavity, whereupon attachment tab 150 expands via the self expansion of wire frame 152 thereby orienting attachment tab 150 in approximation with the abdominal wall 127 and to conform to the curvature thereof for attachment thereto. Expandable member 10*em* is illustrated in an expanded configuration.

Figure 29F:
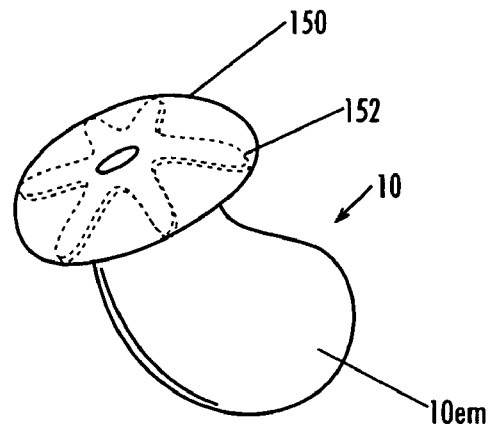
FIGS. 29F-29G show a device provided with a self expanding attachment tab.
Figure 29G:
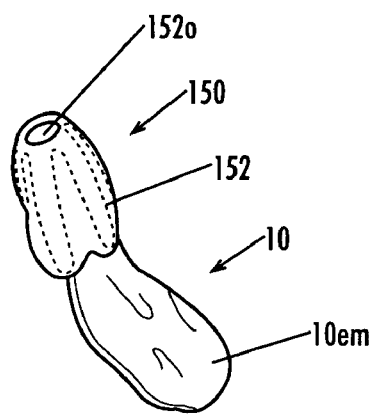

FIGS. 29F-29G show another example of device 10 provided with a self expanding attachment tab 150. In this case, self-expanding member 152 includes bands of resilient, self-expanding material such as any of those discussed above with regard to wire frame 152. Self-expanding member may be sandwiched, or embedded in tab 150 in a manner as also described previously. FIG. 29F shows tab 150 fully expanded and expandable member 10*em* also in an expanded configuration. FIG. 31G illustrates expandable member in a contracted or deflated configuration. Self expanding member 152 in this embodiment is compressed by folding over the bands of the member toward expandable member 10*em* as shown. Conduit 12 (not shown) may pass through a central opening 152*o* of self expanding member 152 and tab 150.

Figure 29H:
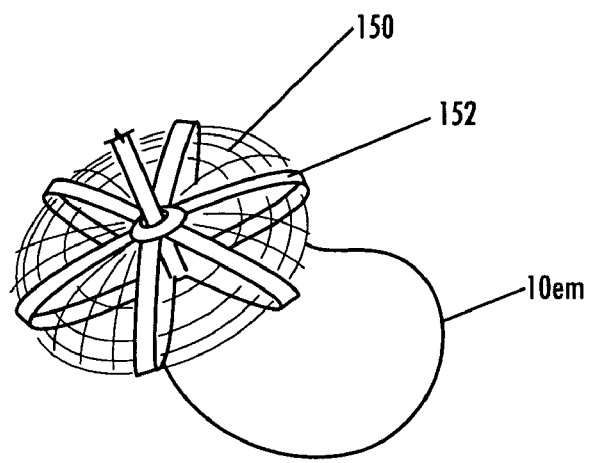
FIGS. 29H-29I illustrate another example of a device provided with a self expanding attachment tab.
Figure 29I:
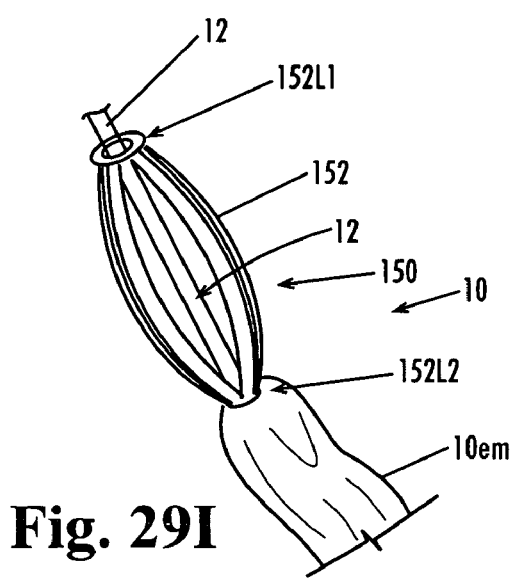

FIGS. 29H-29I illustrate another example of device 10 provided with a self expanding attachment tab 150. In this case, self-expanding member 152 includes folded bands or bows of resilient, self-expanding material, such as any of the previously mentioned materials. Bows are biased toward the folded-over configuration shown in FIG. 29H, where they provide an enlarged radius that prevents tab 150 from passing back through the opening through which device was delivered into the patient and expand attachment tab 150 to conform to the abdominal wall 127 for attachment thereto. FIG. 29I shows expandable member 10*em* in a compressed configuration and self-expanding member also in a compressed configuration, in preparation for delivery of device 10 through a small opening in a patient and into the abdominal cavity. In this embodiment, self expanding member 152 is compressed by applying tension to the proximal end thereof while holding the distal end relatively motionless, whereby it is pulled in the proximal direction to lengthen the self-expanding member, while straightening the bows and thus greatly reducing the radius of self expanding member 152/ attachment tab 150. Self-expanding member may be sandwiched, or embedded in tab 150 in a manner as also described previously.

Figure 29J:
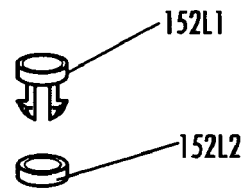
FIG. 29J illustrates one example of connectors, whereby one of the connectors includes resiliently deformable tangs, which are received and locked in the other of the connectors upon joining.

Further alternatively, the embodiment shown in FIGS. 29H-29I may be made from straight bands of spring steel or other material described previously and thus be biased toward the smaller radius, collapsed configuration illustrated in FIG. 29I. In this case, the proximal and distal end rings of structural member 152 are provided with mating interlocking connectors 152L1 and 152L2, respectively. Thus, after insertion of device 10 in the collapsed configuration shown in FIG. 29I, the proximal end connector 152L1 is pushed toward the distal end connector 152L2 while applying a pulling or tension force to the distal end connector 152L2 (for example, by applying tension to conduit 12). When connectors 152L1, 152L2 meet, they interlock, thereby maintaining structural member in the expanded configuration shown in FIG. 29H. FIG. 29J illustrates one example of connectors 152L1, 152L2, whereby one of the connectors includes resiliently deformable tangs, which are received and locked in the other of the connectors upon joining. Connectors 152L1, 152L2 are not limited to the type shown in FIG. 29J, but could be alternative types of mechanical connectors, such as arrangements designed to produce a snap fit, as would be readily apparent to those of ordinary skill in the art.

A portion of expandable member 10em may be customized to provide a surface shape that is tailored to better conform to an intra-abdominal structure to be anchored to. For example, for attachment to the inner surface of the anterior abdominal muscle wall 127, the portion 10ema of the expandable member 10em that contacts the abdominal wall 127 is provided to have a more flattened surface shape, relative to the contour of the remainder of expandable member 10em. FIG. 30A illustrates the orientation of expandable member 10em of device 10 when implanted in a patient according to one embodiment of the present invention, wherein the hatched portion 10ema of expandable member 10em indicates the portion that contacts the abdominal wall 127. Expandable member 10em is placed anteriorly of the stomach and is oriented from an inferior and anterior portion against the anterior abdominal wall 127 towards the spine in a posterior direction, and towards the head in the superior direction. FIG. 30B illustrates the more flattened surface conformation of portion 10ema relative to the curvature of the remainder of expandable member 10em. Locations of optional attachment tab(s) 150 are indicated in phantom lines. Portion 10ema is provided with a matching contour to the contour of the abdominal wall 127 in the location where it contacts the abdominal wall 127. This matching contour not only facilitates attachment of attachment tab(s) 150, but also facilitates proper orientation of expandable member 10em, even when attachment tab(s) are not used to anchor at this location.

Alternatively, the portion 10ema that provides the surface for conforming to the abdominal structure to be anchored to (e.g., abdominal wall) may be provided on an inflatable member 10$em_3$ that is expandable independently of expandable member 10em (or 10$em_1$ or 10$em_2$) as illustrated in FIGS. 31A-31D. FIG. 31A shows inflatable member 10$em_3$ in an expanded (inflated) configuration while expandable member 10em is in a non-expanded or compressed configuration. FIG. 31B shows inflatable member 10$em_3$ in an expanded (inflated) configuration and expandable member 10em in an expanded configuration. Separate access members 80 may be provided for inputting compressed liquid through conduits 12 and 12$_3$ to expandable members 10em and 10$em_3$, respectively, as shown in FIG. 31A. Alternatively, conduits 12 and 12$_3$ may both be connected to a multi-channel access member 80. With both expandable members 10em and 10$em_3$ deflated, the members can be substantially flattened as illustrated in FIG. 31C. Expandable members 10em and 10$em_3$ can then be tightly rolled about the longitudinal axis of device 10, in the direction of the arrow shown in FIG. 31C or direction opposite thereto, to form a compact, rolled device ready for delivery into a patient, see FIG. 31D. Device 10 can be inserted in the arrangement shown, or, optionally, may be encased in a sheath (not shown) for delivery thereof.

After insertion of device 10 though an opening in the patient and into the abdominal cavity, expandable member 10$em_3$ can be expanded as shown in FIG. 31A (either before or after securement of the one or more access members 80 to the patient) whereupon surface 10ema closely approximates the inner anterior abdominal wall 127. Surface 10ema can then be attached to the abdominal wall by suturing, stapling, tacking, etc. one or more attachment tabs 150 to the abdominal wall. Expandable member 10em can next be expanded to fill the space for restricting expansion of the stomach (and optionally, compressing the stomach), or the patient 1 can be closed up and allowed a healing period prior to returning for expansion of expandable member 10em.

Figure 32A:
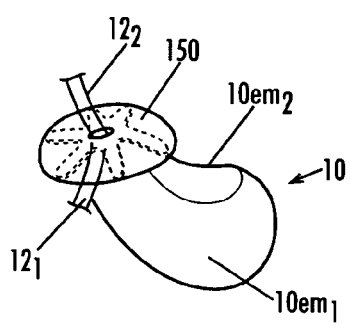
FIG. 32A shows an example of a device having two expandable members wherein a conduit connecting to at least one of the expandable members extends proximally from the expandable members, such as through an opening in an attachment tab.

To assist in orienting attachment tab(s) and device 10 into an intended location and orientation to be implanted in, conduit 12 may be integrated with, or attached to attachment tab 150 to extend radially outward along the attachment tab. Since conduit 12 extends out of the body even after device 10 has been inserted into the abdominal cavity, manipulation and positioning of attachment tab 150 can be performed by pulling and/or pushing on conduit 12 from a location outside the body. FIG. 32A shows an example of a device 10 having two expandable members 10$em_1$, 10$em_2$, wherein a conduit 12 (12$_1$ or 12$_2$, 12$_2$ in the example shown) for one of the expandable members 10$em_1$, 10$em_2$, respectively) extends proximally from expandable members 10$em_1$, 10$em_2$, such as through an opening in attachment tab 150, and a conduit fluidly connected to the other of the expandable members 10$em_1$, 10$em_2$ extends radially outward from the expandable member that it connects with, along attachment tab 150.

Figure 32B:
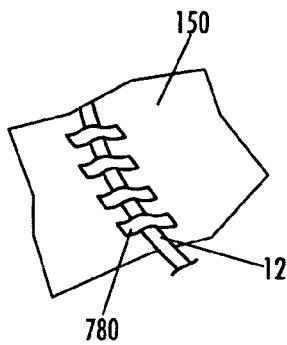
FIG. 32B illustrates overlaying banding strips and adhering the ends of the banding strips on opposite sides of a conduit to an attachment tab.
Figure 32C:
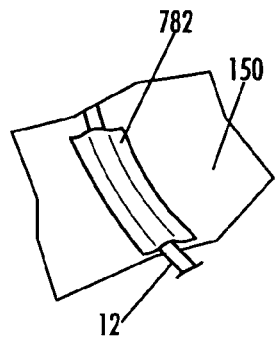
FIG. 32C illustrates a banding sleeve that extends over a majority of the length of the radius (or distance from where attachment tab connects to expandable member to the free edge perimeter) of the attachment tab.

Conduit 12 may be sandwiched between layers of attachment member 150 or may be fixed to the surface of attachment member 150 for example, by overlaying banding strips 780 and adhering the ends of the banding strips on opposite sides of conduit 12 to attachment tab 150, as illustrated in FIG. 32B. For example, banding strips 780 may be made of silicone or reinforced silicone (e.g., Dacron reinforced silicone) and may be adhered to attachment tab 150 using RTV (room temperature vulcanizing) silicone adhesive. As an alternative to the use of banding strips 780, a banding sleeve 782 may be provided that extends over a majority of the length of the radius (or distance from where attachment tab connects to expandable member 10em to the free edge perimeter) of attachment tab 150, as illustrated in FIG. 32C. Banding sleeve 782 may be made of any of the same materials as banding strips 780 and may be adhered in the same way.

Figure 32D:
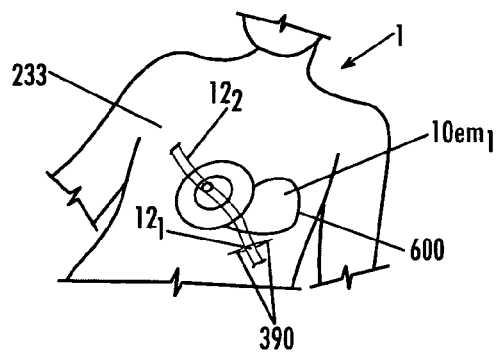
FIG. 32D illustrates manipulation of one or more conduits to move and position attachment tab(s) into a desired location against the anterior abdominal wall.

In use, device 10 may be inserted through a small percutaneous opening 223, as described above, or through a port in a laparoscopic procedure, with both conduits 121, 122 extending out of the insertion opening. In the case of a laparoscopic procedure, a tool, such as a grasper or other tool designed for laparoscopic use can be inserted through a second opening or port 390 to capture one of the conduits (e.g., conduit $12_1$ as shown in FIG. 32D) and draw it out of the second opening 390. Conduits $12_2$ and $12_1$ can then be manipulated to move and position attachment tab(s) 150 into a desired location against the anterior abdominal wall 127. In the case of a percutaneous procedure, a small puncture can be made at 390, using a tool 772 such as described with regard to FIG. 26E, for example, or other tool or combination of tool configured to perform a puncture and to capture a conduit 12, and the conduit can then be capture and withdrawn through the opening 390. Laparoscopic ports 390 may have a diameter of about ten to about twelve millimeters, up to about eighteen millimeters and as small as about five millimeters, although the typical size is about eight to twelve millimeters. Percutaneous opening 223 may be formed by an incision less than about seven cm, typically less than about five cm.

Figure 32E:
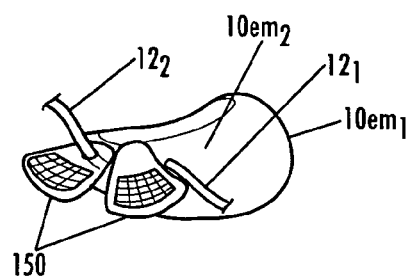
FIG. 32E illustrates a device having separate attachment tabs.
Figure 32F:
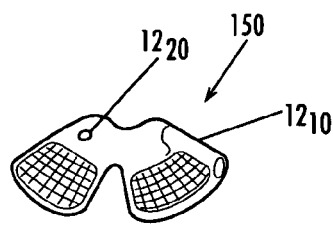
FIG. 32F illustrates a device having a segmented attachment tab.

Alternatively, conduits $12_1$ and $12_2$ may pass through separate attachment tabs 150, as shown in FIG. 34E. By providing separate or segmented attachment features 150, this allows more flexibility in placement of the attachment tabs 150 as to anchoring location, and also may help in conforming to the tissues to be anchored to, but still provides the control of positioning and orientation of the inferior portion of device 10 and attachment tab 150 that was described with regard to FIG. 32D above. Attachment tabs 150 may be separate, as shown in FIG. 32E, or this flexibility may also be provided by a segmented attachment tab 150 as illustrated in FIG. 32F, where $12_{2o}$ shows an opening through which conduit $12_2$ passes and $12_{1o}$ shows a tunnel or lumen through which conduit $12_1$ passes. If the outermost layer of expandable member 10em is made of silicone, RTV silicone adhesive can be used to adhere attachment tab(s) 150 to the expandable member. One or more of the attachment tabs 150 may extend along expandable member 10em, or may join with backing support 10ds to provide a larger surface area for force distribution. These extensions and/or backing support 10ds may optionally also be provided with one or more patches of tissue ingrowth-enhancing material. Further, the a portion or all of a side of expandable member, such as the anterior facing surface, as illustrated in FIG. 27B may be coated with a layer or otherwise structurally reinforced so as not to expand, or at least not expand as much as the remainder of expandable member 10em, to prevent or at least reduce expansion of expandable member in the anterior direction, and thereby reduce any visible bulging on the external abdomen of the patient (i.e., skin appearance/shape outside the abdominal cavity), while expandable member 10em is allowed to preferentially expand posteriorly and medially to effect filling of the space intended to be filled.

In an alternative attachment procedure, tube $12_1$ and $12_2$ can be routed through different openings in a patient, similar to any of the ways described above with regard to FIG. 32D. However, in this alternative approach, attachment tabs 150 are not attached (at least not stapled, tacked or sutured to the abdominal wall, but they may be maintained to encourage tissue ingrowth, or a more conforming tissue ingrowth layer can be provided over an inferior portion of expandable member 10em, or neither) to the abdominal wall. Rather, tubes $12_1$ and $12_2$ are used to position and orient device 10 as desired and device 10 is anchored via tube $12_1$ and $12_2$, using nuts, sutures, access members, or any of the other features/techniques described previously. Thus, no suturing or stapling to the abdominal wall (at least to the abdominal wall inside the abdominal cavity) is required.

In any of the procedures described herein, it may be advantageous to orient the patient on his back, with the table angled from about fifteen to about forty-five degrees, typically about thirty degrees, to elevate the head of the patient 1. This causes the organs in the abdominal cavity to shift in and inferior direction thereby providing more space in the superior portion of the abdominal cavity and adjacent the diaphragm 116 to facilitate the insertion procedures.

Figure 33:
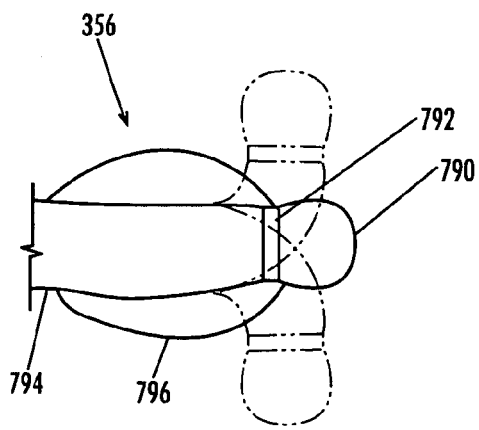
FIG. 33 illustrates a distal end portion of a flexible endoscope that may be used in a procedure to assist visualization of the placement of a device during an implantation procedure.

FIG. 33 illustrates a distal end portion of a flexible, endoscope 356 that may be used in a mini-laparoscopic or laparoscopic procedure to assist visualization of the placement of device 10 during an implantation procedure. Endoscope 356 may be used with our without additional fluoroscopic visualization. For example, in an office setting, use of endoscope 356 without any fluoroscopic visualization may be sufficient for a minimally invasive procedure such as described herein. Endoscope 356 includes an atraumatic lens 790 at a distal end portion thereof, with a camera or other visualization means 792 (e.g., optical fibers extending up to the lens 790 or a CCD camera placed just proximally of lens 790) to provide an image that is delivered to the proximal end of endoscope 356 outside of the body of the patient. The shaft 794 of endoscope 356 is flexible, may be constructed according to existing flexible catheter technology and typically has an outside diameter of five mm or less, preferably about four mm or less, more preferably about three mm or less. The diameter of endoscope shaft 794/lens 790 is in the range of about two to about ten mm, typically about five mm. The distal end portion of endoscope 356 is steerable, as illustrated by the phantom lines in FIG. 33, and endoscope 356 may be maneuvered or steered into a surgical site to provide a desired view, as well as steered, once in a desired site, to provide panning of a location in the abdomen. Steering may be controlled by wires that run along the length of viewing fibers within shaft 794 up to the tip 790. The wires that the proximal end portion are connected to a steering mechanism that tensions the wires and causes deflections at the tip of the scope 356. For a more detailed description, see Breedveld et al., "A New, Easily Miniaturized Steerable Endoscope", IEEE Engineering in Medicine and Biology, November/December 2005, pp. 40-47, which is hereby incorporated herein, in its entirety, by reference thereto. Alternatively, endoscope 356 may be inserted through a guide catheter for delivery of the distal end portion to a desired location.

Once the distal end of endoscope 356 has been maneuvered into a desired viewing location, a balloon 796, that is mounted annularly around shaft 794 just proximal of lens 790, can be inflated to lift adjacent tissues to improve the visualization through lens 790.

Figure 34:
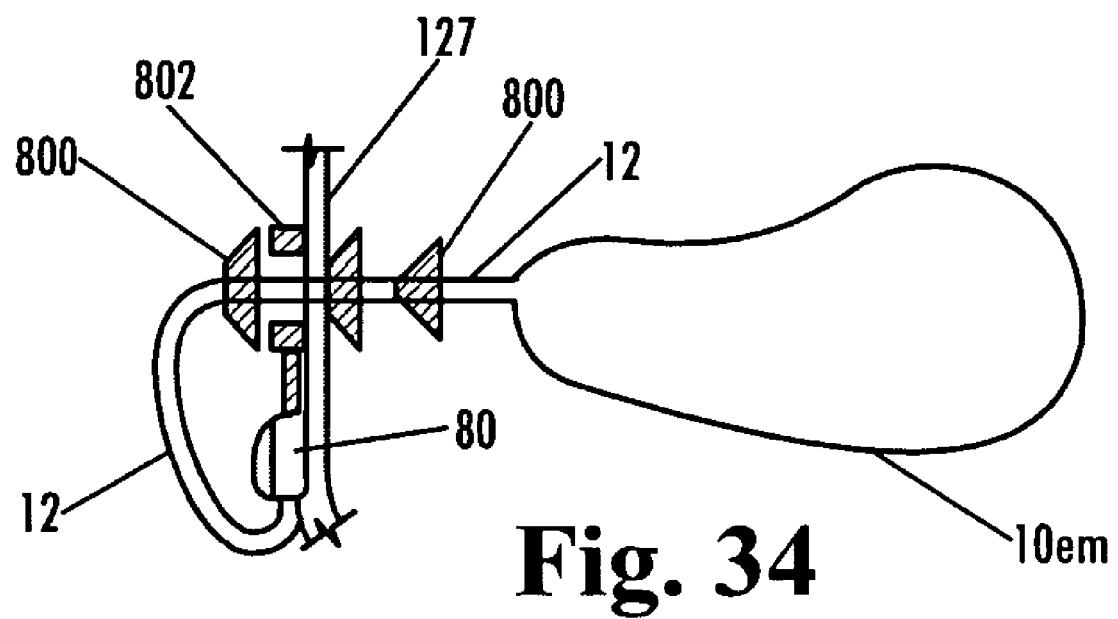
FIG. 34 illustrates anchoring of an expandable member using a feature including ratcheted teeth.

Another feature for anchoring expandable member 10em of device 10 is illustrated in FIG. 34. This feature includes ratcheted teeth (e.g., spaced teeth 800 and a collar 802. The teeth 800 are spaced along conduit 12 and annularly surround the conduit wall to radially extend outward therefrom. Teeth 800 have an outside diameter at a distal portion thereof that is larger than the inside diameter of collar 802, and the proximal end portions of teeth 800 have an outside diameter that is less than the inside diameter of collar 802. Further, teeth 800 are deformable, and tapered to allow them to be pulled through collar 802. As a tooth 800 passes through collar 800 it deforms to allow the passage, and then re-expands to its original configuration. Since the distal ends of teeth 800 are not tapered or beveled, teeth 800 are prevented from passing back through collar 802 in the distal direction. Thus, upon insertion, initial placement and expansion of expandable member 10em, the surgeon can next place collar 892 up against the external surface of the abdominal wall 127, as shown in FIG. 34, and pull conduit 12 proximally therethrough to pull one or more of teeth 800 through collar 802, thereby anchoring expandable member 10em to the abdominal wall. The surgeon can adjust the positioning of expandable member 10*em*, according to the number of teeth 800 that are pulled through collar 802, wherein the teeth 800 and collar 802 function like a ratchet. The conduit 12 extending proximally of collar 802 is connected to access member 80 which can also be attached to the abdominal wall at another location. This arrangement also relieves stress from access member 80 and the connection of conduit 12 with access member 80.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of treating a patient, said method comprising:
    passing a device including an expandable member through the skin of the patient, through the abdominal wall of the patient and into the abdominal cavity of the patient;
    expanding the expandable member in a space in the abdominal cavity to perform at least one of: prevention of expansion of the stomach of the patient into the space; and compression of a portion of the stomach;
    providing a layer of material that enhances tissue ingrowth between the expandable member and the inner surface of the abdominal wall and
    anchoring the expanded expandable member against the abdominal wall of the patient.

2. The method of claim 1, further comprising anchoring at least a portion of the expandable member, relative to at least one structure in the abdominal cavity, without piercing the stomach.

3. The method of claim 1, wherein said anchoring against the abdominal wall comprises threading a lock nut against an external surface of the abdominal wall and over a conduit extending out of the abdominal wall that is in fluid communication with said expandable member.

4. The method of claim 3, further comprising providing a layer of material that enhances tissue ingrowth between the lock nut and the external surface of the abdominal wall.

5. The method of claim 3, wherein said anchoring comprises:
    drawing at least one ratcheted tooth through a small opening in the abdominal wall, wherein a plurality of said ratcheted teeth are attached to a conduit at locations internal of the abdominal wall and wherein said conduit extends out of the abdominal wall and is in fluid communication with said expandable member, wherein said ratcheted teeth are configured to be retractable out of the abdominal cavity but are prevented from passing back into the abdominal cavity.

6. A method of treating a patient, said method comprising:
    passing a device including an expandable member through the skin of the patient, through the abdominal wall of the patient and into the abdominal cavity of the patient;
    expanding the expandable member in a space in the abdominal cavity to perform at least one of: prevention of expansion of the stomach of the patient into the space; and compression of a portion of the stomach;
    providing a layer of material that enhances tissue ingrowth between the expandable member and a surface of a structure other than the stomach in the abdominal cavity; and
    anchoring the expanded expandable member against the structure.

* * * * *